(12) United States Patent
Utsumi et al.

(10) Patent No.: US 8,765,352 B2
(45) Date of Patent: Jul. 1, 2014

(54) RESIST COMPOSITION, METHOD OF FORMING RESIST PATTERN, NOVEL COMPOUND, AND ACID GENERATOR

(75) Inventors: Yoshiyuki Utsumi, Kawasaki (JP); Takehiro Seshimo, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 115 days.

(21) Appl. No.: 13/223,595

(22) Filed: Sep. 1, 2011

(65) Prior Publication Data

US 2012/0058430 A1    Mar. 8, 2012

(30) Foreign Application Priority Data

Sep. 2, 2010    (JP) ................ P2010-196761

(51) Int. Cl.
| | | |
|---|---|---|
| G03F 7/004 | (2006.01) | |
| G03F 7/029 | (2006.01) | |
| G03F 7/039 | (2006.01) | |
| C07C 381/12 | (2006.01) | |
| C07C 309/06 | (2006.01) | |
| C07C 309/07 | (2006.01) | |

(52) U.S. Cl.
USPC ........ 430/270.1; 430/326; 430/921; 430/922; 430/925; 568/22; 568/24; 568/27; 568/28; 560/129; 560/165; 560/167

(58) Field of Classification Search
USPC .............. 430/270.1, 325, 326, 921, 922, 925; 549/305, 311; 560/129, 165, 167; 568/22, 24, 27, 28
See application file for complete search history.

(56) References Cited

U.S. PATENT DOCUMENTS

| | | |
|---|---|---|
| 5,945,517 A | 8/1999 | Nitta et al. |
| 6,153,733 A | 11/2000 | Yukawa et al. |
| 6,444,397 B2 | 9/2002 | Hada et al. |
| 6,949,325 B2 | 9/2005 | Li et al. |
| 7,074,543 B2 | 7/2006 | Iwai et al. |
| 7,527,913 B2 | 5/2009 | Yun et al. |
| 2008/0182203 A1 | 7/2008 | Yun et al. |
| 2009/0291390 A1* | 11/2009 | Jung et al. .................. 430/270.1 |
| 2010/0035185 A1* | 2/2010 | Hagiwara et al. .......... 430/286.1 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2009-007327 | 1/2009 |
| JP | A-2013-520458 | 6/2013 |
| WO | WO 2004/074242 | 9/2004 |
| WO | WO 2011/104127 | 9/2011 |

OTHER PUBLICATIONS

Notice of Allowance mailed May 7, 2014 in Japanese Application No. 2010-196761.

* cited by examiner

*Primary Examiner* — Anca Eoff
(74) *Attorney, Agent, or Firm* — Knobbe, Martens, Olson & Bear, LLP

(57) ABSTRACT

A positive resist composition including a base component (A) which exhibits changed solubility in an alkali developing solution under the action of acid and an acid-generator component (B) which generates acid upon exposure, wherein the acid-generator component (B) includes an acid generator (B1) containing a compound represented by general formula (b1-1) shown below (wherein $Z^+$ represents an organic cation).

[Chemical Formula 1]

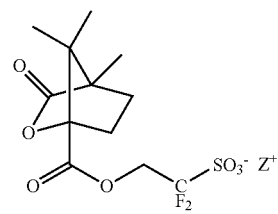

(b1-1)

9 Claims, No Drawings

RESIST COMPOSITION, METHOD OF FORMING RESIST PATTERN, NOVEL COMPOUND, AND ACID GENERATOR

TECHNICAL FIELD

The present invention relates to a resist composition, a method of forming a resist pattern using the resist composition, a novel compound that is useful as an acid generator for the resist composition, and an acid generator.

Priority is claimed on Japanese Patent Application No. 2010-196761, filed Sep. 2, 2010, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (and increasing the energy) of the exposure light source. Conventionally, ultraviolet radiation typified by g-line and i-line radiation has been used, but nowadays KrF excimer lasers and ArF excimer lasers are starting to be introduced in the mass production of semiconductor elements. Furthermore, research is also being conducted into lithography techniques that use an exposure light source having a shorter wavelength (and a higher energy level) than these excimer lasers, such as electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base component which exhibits changed solubility in an alkali developing solution under the action of acid and an acid generator that generates acid upon exposure.

For example, a positive-type chemically amplified resist composition typically contains a resin component (base resin) which exhibits increased solubility in an alkali developing solution under the action of acid, and an acid generator component. If the resist film formed using this resist composition is selectively exposed during formation of a resist pattern, then within the exposed portions, acid is generated from the acid generator, and the action of this acid causes an increase in the solubility of the resin component in an alkali developing solution, making the exposed portions soluble in the alkali developing solution.

Currently, resins that contain structural units derived from (meth)acrylate esters within the main chain (acrylic resins) are widely used as base resins for resist compositions that use ArF excimer laser lithography or the like, as they exhibit excellent transparency in the vicinity of 193 nm (for example, see Patent Document 1).

As acid generators usable in chemically amplified resist compositions, various types have been proposed including, for example, onium salt acid generators such as iodonium salts and sulfonium salts, oxime sulfonate acid generators, diazomethane acid generators, nitrobenzylsulfonate acid generators, iminosulfonate acid generators, and disulfone acid generators.

Among these, onium salt acid generators having an onium ion such as triphenylsulfonium as the cation moiety are widely used as acid generators. The anion moiety of these onium salt acid generators is typically an alkylsulfonate ion or a fluorinated alkylsulfonate ion in which some or all of the hydrogen atoms of the alkyl group have been substituted with fluorine atoms.

Further, resist compositions containing a fluorine-containing sulfonate onium salt represented by formula (1) shown below or an onium salt having an anion represented by formula (2) shown below as the acid generator have also been disclosed (see Patent Documents 2 and 3).

[Chemical Formula 1]

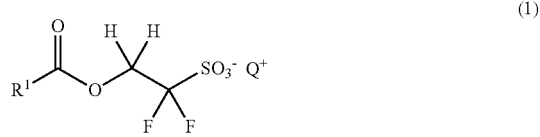

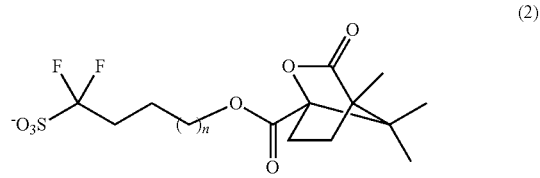

In formula (1), $R^1$ represents a monovalent organic group, and $Q^+$ represents a sulfonium cation or an iodonium cation. In formula (2), n represents an integer of 1 to 3.

PRIOR ART DOCUMENTS

Patent Documents

[Patent Document 1]
Japanese Unexamined Patent Application, First Publication No. 2003-241385
[Patent Document 2]
Japanese Unexamined Patent Application, First Publication No. 2009-7327
[Patent Document 3]
U.S. Pat. No. 7,527,913

DISCLOSURE OF INVENTION

Problems to be Solved by the Invention

Among the onium salt acid generators mentioned above, onium salt acid generators having a perfluoroalkylsulfonate ion as the anion moiety are currently the most commonly used.

In recent years, with progress in the miniaturization of resist patterns, there are growing demands for further improvements in the resist pattern shape and a variety of other lithography properties for conventional chemically amplified resist compositions containing an onium salt acid generator having a perfluoroalkylsulfonate ion as the anion moiety.

However, Patent Documents 2 and 3 have not disclosed a resist composition and acid generator that adequately satisfy the demands for improvements in properties such as the roughness, mask reproducibility, exposure margin, and rectangularity of the resist pattern shape upon resist pattern formation.

In this regard, there are strong demands for a compound that is more useful than conventional compounds as the acid generator for a resist composition.

The present invention takes the above circumstances into consideration, with an object of providing a compound that is useful as an acid generator for a resist composition, an acid generator including the compound, a resist composition containing the acid generator, and a method of forming a resist pattern using the resist composition.

Means to Solve the Problems

In order to achieve the above object, the present invention employs the aspects described below.

Specifically, a first aspect of the present invention is a resist composition including a base component (A) which exhibits changed solubility in an alkali developing solution under the action of acid and an acid-generator component (B) which generates acid upon exposure, the acid-generator component (B) including an acid generator (B1) containing a compound represented by general formula (b1-1) shown below.

[Chemical Formula 2]

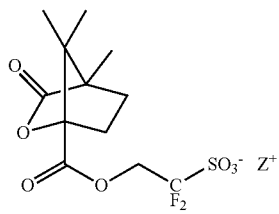

(b1-1)

In the formula, $Z^+$ represents an organic cation.

A second aspect of the present invention is a method of forming a resist pattern, the method including: forming a resist film on a substrate using a resist composition according to the first aspect, subjecting the resist film to exposure, and subjecting the resist film to alkali developing to form a resist pattern.

A third aspect of the present invention is a compound represented by general formula (b1-1) shown below.

[Chemical Formula 3]

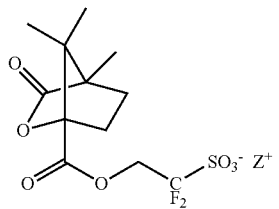

(b1-1)

In the formula, $Z^+$ represents an organic cation.

A fourth aspect of the present invention is an acid generator including the compound of the third aspect.

In the present description and claims, an "alkyl group" includes linear, branched and cyclic, monovalent saturated hydrocarbon groups, unless otherwise specified.

The term "alkylene group" includes linear, branched and cyclic divalent saturated hydrocarbon groups, unless otherwise specified.

A "lower alkyl group" is an alkyl group of 1 to 5 carbon atoms.

A "halogenated alkyl group" is a group in which some or all of the hydrogen atoms of an alkyl group are each substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

The term "(meth)acrylic acid" is a generic term that includes either or both of acrylic acid having a hydrogen atom bonded to the α-position and methacrylic acid having a methyl group bonded to the α-position.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

Effect of the Invention

According to the present invention, there are provided a compound that is useful as an acid generator for a resist composition, an acid generator including the compound, a resist composition containing the acid generator, and a method of forming a resist pattern using the resist composition.

The resist composition and the method of forming a resist pattern according to the present invention enable the formation of a resist pattern having excellent lithography properties such as roughness, mask reproducibility and exposure margin, as well as a favorable shape with a high degree of rectangularity.

DETAILED DESCRIPTION OF THE INVENTION

Resist Composition

The resist composition according to the first aspect of the present invention includes a base component (A) which exhibits changed solubility in a developing solution under the action of acid (hereinafter referred to as "component (A)"), and an acid generator component (B) which generates acid upon exposure (hereinafter referred to as "component (B)").

When the resist film that is formed using the resist composition is subjected to selective exposure during resist pattern formation, acid is generated from the component (B), and the generated acid acts on the component (A) to change the solubility of the component (A) in an alkali developing solution. As a result, the solubility of the exposed portions of the resist film in an alkali developing solution is changed, whereas the solubility of the unexposed portions in an alkali developing solution remains unchanged, and therefore subsequent alkali developing can be used to form a resist pattern, by dissolving and removing either the exposed portions in the case of a positive resist composition, or the unexposed portions in the case of a negative resist composition.

The resist composition of the present invention may be either a negative resist composition or a positive resist composition.

<Component (A)>

As the component (A), a single organic compound typically used as a base component for a chemically amplified resist composition may be used alone, or two or more of such organic compounds may be mixed together.

Here, the term "base component" refers to an organic compound capable of forming a film, and is preferably an organic compound having a molecular weight of 500 or more. Ensuring that the organic compound has a molecular weight of 500 or more improves the film-forming ability, and facilitates the formation of nano level resist patterns.

The "organic compounds having a molecular weight of 500 or more" that can be used as the base component may be broadly classified into non-polymers and polymers.

In general, compounds which have a molecular weight of at least 500 but less than 4,000 may be used as non-polymers. Hereinafter, a non-polymer having a molecular weight of at least 500 but less than 4,000 is referred to as a "low molecular weight compound".

In terms of the polymers, compounds which have a molecular weight of 1,000 or more may be used. Hereinafter, a polymer having a molecular weight of 1,000 or more is referred to as a "polymeric compound". In the case of a polymeric compound, the "molecular weight" refers to the polystyrene-equivalent weight-average molecular weight determined by gel permeation chromatography (GPC). Hereinafter, a polymeric compound is frequently referred to as simply a "resin".

Either a resin component that exhibits changed solubility in an alkali developing solution under the action of acid, or a low molecular weight compound that exhibits changed solubility in an alkali developing solution under the action of acid may be used as the component (A).

When the resist composition of the present invention is a negative resist composition, a base component that is soluble in an alkali developing solution is used as the component (A), and the resist composition also includes a cross-linking agent.

In the negative resist composition, when acid is generated from the component (B) upon exposure, the action of the generated acid causes cross-linking between the base component and the cross-linking agent, and the cross-linked portions become insoluble in an alkali developing solution. Accordingly, during resist pattern formation, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, a resin that is soluble in an alkali developing solution (hereinafter referred to as an "alkali-soluble resin") is used as the component (A) for a negative resist composition.

As the alkali-soluble resin, it is preferable to use a resin having a structural unit derived from at least one of an α-(hydroxyalkyl)acrylic acid, and an alkyl ester (and preferably an alkyl ester of 1 to 5 carbon atoms) of an α-(hydroxyalkyl) acrylic acid, as disclosed in Japanese Unexamined Patent Application, First Publication No. 2000-206694; a (meth) acrylic resin or polycycloolefin resin having a sulfonamide group, as disclosed in U.S. Pat. No. 6,949,325; a (meth) acrylic resin containing a fluorinated alcohol, as disclosed in U.S. Pat. No. 6,949,325, Japanese Unexamined Patent Application, First Publication No. 2005-336452 and Japanese Unexamined Patent Application, First Publication No. 2006-317803; or a polycycloolefin resin having a fluorinated alcohol as disclosed in Japanese Unexamined Patent Application, First Publication No. 2006-259582, as such resins enable the formation of a satisfactory resist pattern with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (and preferably a hydroxyalkyl group of 1 to 5 carbon atoms) is bonded to the carbon atom on the α-position.

As the cross-linking agent, at least one compound selected from the group consisting of melamine-based cross-linking agents, urea-based cross-linking agents, alkylene urea-based cross-linking agents, glycoluril-based cross-linking agents and epoxy-based cross-linking agents is preferred. For example, usually, a glycoluril-based cross-linking agent having a methylol group or alkoxymethyl group or a melamine-based cross-linking agent is preferable, as it enables formation of a resist pattern with minimal swelling. The amount added of the cross-linking agent is preferably within a range from 1 to 50 parts by weight, relative to 100 parts by weight of the alkali-soluble resin.

When the resist composition of the present invention is a positive resist composition, as the component (A), a base component (A0) which exhibits increased solubility in an alkali developing solution under the action of acid (hereinafter referred to as "component (A0)") is used.

The component (A0) is insoluble in an alkali developing solution prior to exposure, but when acid is generated from the component (B) upon exposure, the solubility of the component (A0) in an alkali developing solution increases as a result of the action of the acid. Accordingly, during resist pattern formation, by conducting selective exposure of a resist film formed by applying the positive resist composition onto a substrate, the exposed portions change from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component (A0) which exhibits increased solubility in an alkali developing solution under the action of acid. That is, the resist composition of the present invention is preferably a positive resist composition.

The component (A0) may be a resin component (A1) that exhibits increased solubility in an alkali developing solution under the action of acid (hereinafter frequently referred to as "component (A1)"), a low molecular weight material (A2) that exhibits increased solubility in an alkali developing solution under the action of acid (hereinafter frequently referred to as "component (A2)"), or a mixture thereof.

[Component (A1)]

As the component (A1), a single resin component (base resin) typically used as a base component for a chemically amplified resist may be used alone, or two or more of such resin components may be mixed together.

In the present invention, the component (A1) preferably includes a structural unit derived from an acrylate ester, or a structural unit derived from an acrylate ester having an atom other than a hydrogen atom or a substituent bonded to the carbon atom on the α-position.

In the present descriptions and claims, the expression "structural unit derived from an acrylate ester" refers to a structural unit which is formed by the cleavage of the ethylenic double bond of an acrylate ester The term "acrylate ester" refers to acrylate esters having a hydrogen atom bonded to the carbon atom on the α-position.

In an "acrylate ester having an atom other than a hydrogen atom or a substituent bonded to the carbon atom on the α-position", examples of the atom other than a hydrogen atom include halogen atoms, whereas examples of the substituent include alkyl groups of 1 to 5 carbon atoms and halogenated alkyl groups of 1 to 5 carbon atoms. Examples of the halogen atom include a fluorine atom, chlorine atom, bromine atom or iodine atom.

The α-position (carbon atom on the α-position) of a structural unit derived from an acrylate ester refers to the carbon atom bonded to the carbonyl group, unless specified otherwise.

In the acrylate ester, specific examples of the alkyl groups of 1 to 5 carbon atoms for the substituent at the α-position include linear or branched lower alkyl groups such as a methyl group, ethyl group, propyl group, isopropyl group, n-butyl group, isobutyl group, tert-butyl group, pentyl group, isopentyl group or neopentyl group.

Specific examples of the halogenated alkyl group of 1 to 5 carbon atoms include groups in which some or all of the hydrogen atoms of an aforementioned "alkyl group of 1 to 5 carbon atoms for the substituent at the α-position" are substituted with halogen atoms. Examples of the halogen atom include a fluorine atom, chlorine atom, bromine atom or iodine atom, and a fluorine atom is particularly desirable.

In the present invention, it is preferable that a hydrogen atom, an alkyl group of 1 to 5 carbon atoms or a halogenated alkyl group of 1 to 5 carbon atoms is bonded to the α-position of the acrylate ester. Of these, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

In the resist composition of the present invention, the component (A1) preferably includes a structural unit (a1), which is derived from an acrylate ester that may have an atom other than a hydrogen atom or a substituent bonded to the carbon atom on the α-position, and contains an acid-dissociable, dissolution-inhibiting group.

Further, in addition to the structural unit (a1), the component (A1) preferably also includes a structural unit (a2), which is derived from an acrylate ester that may have an atom other than a hydrogen atom or a substituent bonded to the carbon atom on the α-position, and contains a lactone-containing cyclic group.

Further, in addition to the structural unit (a1), the component (A1) preferably also includes a structural unit (a3), which is derived from an acrylate ester that may have an atom other than a hydrogen atom or a substituent bonded to the carbon atom on the α-position, and contains a polar group-containing aliphatic hydrocarbon group.

Furthermore, in addition to the structural unit (a1), the component (A1) preferably also includes a structural unit (a0), which is derived from an acrylate ester that may have an atom other than a hydrogen atom or a substituent bonded to the carbon atom on the α-position, and contains an —$SO_2$-containing cyclic group.

Moreover, in the present invention, the component (A1) may also include other structural units besides the structural units (a1) to (a3) and (a0) described above.

(Structural Unit (a1))

The structural unit (a1) is a structural unit which is derived from an acrylate ester that may have an atom other than a hydrogen atom or a substituent bonded to the carbon atom on the α-position, and contains an acid-dissociable, dissolution-inhibiting group.

As the acid-dissociable, dissolution-inhibiting group in the structural unit (a1), any of the groups that have been proposed as acid-dissociable, dissolution-inhibiting groups for the base resins of chemically amplified resists can be used, provided the group has an alkali dissolution-inhibiting effect that renders the entire component (A1) insoluble in an alkali developing solution prior to dissociation, and then following dissociation under the action of acid, increases the solubility of the entire component (A1) in the alkali developing solution. Generally, groups that form either a cyclic or chain-like tertiary alkyl ester with the carboxyl group of the (meth)acrylic acid, and acetal-type acid-dissociable, dissolution-inhibiting groups such as alkoxyalkyl groups are the most widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom.

The chain-like or cyclic alkyl group may have a substituent.

Hereinafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of tertiary alkyl ester-type acid-dissociable, dissolution-inhibiting groups include aliphatic branched, acid-dissociable, dissolution-inhibiting groups and aliphatic cyclic group-containing acid-dissociable, dissolution-inhibiting groups.

In the present description and claims the term "aliphatic branched" refers to a branched structure having no aromaticity.

The structure of the "aliphatic branched acid-dissociable group" is not limited to groups constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of preferred aliphatic branched acid-dissociable, dissolution-inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, a fluorine atom, a fluorinated lower alkyl groups of 1 to 5 carbon atoms, and an oxygen atom (=O).

The basic ring structure of the "aliphatic cyclic group" excluding substituents is not limited to structures constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

Examples of such aliphatic cyclic groups include groups in which one or more hydrogen atoms have been removed from a monocycloalkane or a polycycloalkane such as a bicycloalkane, tricycloalkane or tetracycloalkane, which may or may not be substituted with a lower alkyl group, a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

Examples of the aliphatic cyclic group-containing acid-dissociable, dissolution-inhibiting group include groups having a tertiary carbon atom within the ring structure of a cyclic alkyl group. Specific examples include a 2-methyl-2-adamantyl group and a 2-ethyl-2-adamantyl group. Alternatively, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, such as the groups bonded to the oxygen atom of the carbonyloxy group (—C(O)—O—) in the structural units represented by general formulas (a1"-1) to (a1"-6) shown below, may also be used.

[Chemical Formula 4]

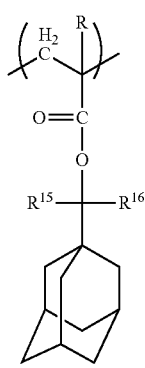

(a1"-1)

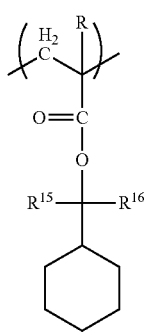

(a1"-2)

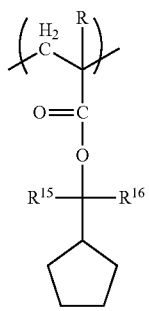

(a1"-3)

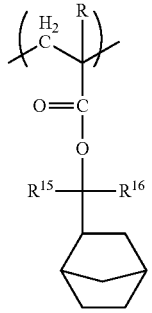

(a1"-4)

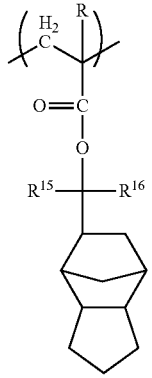

(a1"-5)

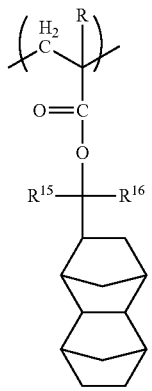

(a1"-6)

In the above formulas, each R independently represents a hydrogen atom, a lower alkyl group or a halogenated lower alkyl group, and $R^{15}$ and $R^{16}$ each represents an alkyl group (which may be linear or branched, and preferably has 1 to 5 carbon atoms).

In general formulas (a1"-1) to (a1"-6), the lower alkyl group or halogenated lower alkyl group for R is the same as defined for the alkyl group of 1 to 5 carbon atoms or halogenated alkyl group of 1 to 5 carbon atoms that may be bonded to the α-position of an aforementioned acrylate ester.

An "acetal-type acid-dissociable, dissolution-inhibiting group" generally substitutes a hydrogen atom at the terminal of an alkali-soluble group such as a carboxyl group or hydroxyl group, so as to be bonded with an oxygen atom. When acid is generated upon exposure, the generated acid acts to break the bond between the acetal-type acid-dissociable, dissolution-inhibiting group and the oxygen atom to which the acetal-type, acid-dissociable, dissolution-inhibiting group is bonded.

Examples of acetal-type acid-dissociable, dissolution-inhibiting groups include groups represented by general formula (p1) shown below.

[Chemical Formula 5]

(p1)

In the formula, each of $R^{1\prime}$ and $R^{2\prime}$ independently represents a hydrogen atom or a lower alkyl group, n represents an integer of 0 to 3, and Y represents a lower alkyl group or an aliphatic cyclic group.

In the formula above, n is preferably an integer of 0 to 2, more preferably 0 or 1, and most preferably 0.

Examples of the lower alkyl group for $R^{1\prime}$ and $R^{2\prime}$ include the same lower alkyl groups as those listed above for R, although a methyl group or ethyl group is preferable, and a methyl group is particularly desirable.

In the present invention, it is preferable that at least one of $R^{1\prime}$ and $R^{2\prime}$ is a hydrogen atom. That is, it is preferable that the acid-dissociable, dissolution-inhibiting group (p1) is a group represented by general formula (p1-1) shown below.

[Chemical Formula 6]

(p1-1)

In the formula, $R^{1\prime}$, n and Y are the same as defined above.

Examples of the lower alkyl group for Y include the same groups as those listed above for the lower alkyl group for R.

As the aliphatic cyclic group for Y, any of the monocyclic or polycyclic aliphatic cyclic groups which have been proposed for conventional ArF resists and the like can be appropriately selected for use. For example, the same groups described above in connection with the "aliphatic cyclic group" can be used.

Further, as the acetal-type, acid-dissociable, dissolution-inhibiting group, groups represented by general formula (p2) shown below may also be used.

[Chemical Formula 7]

(p2)

In the formula, each of $R^{17}$ and $R^{18}$ independently represents a linear or branched alkyl group or a hydrogen atom, and $R^{19}$ represents a linear, branched or cyclic alkyl group. Alternatively, each of $R^{17}$ and $R^{19}$ may independently represent a linear or branched alkylene group, wherein $R^{17}$ is bonded to $R^{19}$ to form a ring.

The alkyl group for $R^{17}$ or $R^{18}$ preferably has 1 to 15 carbon atoms, and may be either linear or branched. As the alkyl group, an ethyl group or a methyl group is preferable, and a methyl group is most preferable.

It is particularly desirable that one of $R^{17}$ and $R^{18}$ is a hydrogen atom and the other is a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane and cyclohexane, or a polycycloalkane such as adamantane, norbornane, isobornane, tricyclodecane or tetracyclododecane. Among these, a group in which one or more hydrogen atoms have been removed from adamantane is preferable.

In the formula above, each of $R^{17}$ and $R^{19}$ may independently represent a linear or branched alkylene group (and preferably an alkylene group of 1 to 5 carbon atoms), wherein $R^{19}$ is bonded to $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of this cyclic group include tetrahydropyranyl group and tetrahydrofuranyl group.

As the structural unit (a1), it is preferable to use at least one type of structural unit selected from the group consisting of structural units represented by general formula (a1-0-1) shown below and structural units represented by general formula (a1-0-2) shown below.

[Chemical Formula 8]

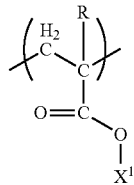

(a1-0-1)

In the formula, R represents a hydrogen atom, a lower alkyl group or a halogenated lower alkyl group, and $X^1$ represents an acid-dissociable, dissolution-inhibiting group.

[Chemical Formula 9]

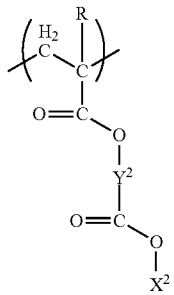

(a1-0-2)

In the formula, R represents a hydrogen atom, a lower alkyl group or a halogenated lower alkyl group, $X^2$ represents an acid-dissociable, dissolution-inhibiting group, and $Y^2$ represents a divalent linking group.

In formula (a1-0-1) shown above, the lower alkyl group and halogenated lower alkyl group for R are the same as the alkyl group of 1 to 5 carbon atoms and halogenated alkyl group of 1 to 5 carbon atoms which may be bonded to the α-position of the aforementioned acrylate ester.

$X^1$ is not particularly limited as long as it is an acid-dissociable, dissolution-inhibiting group. Examples include the aforementioned tertiary alkyl ester-type acid-dissociable, dissolution-inhibiting groups and acetal-type acid-dissociable, dissolution-inhibiting groups, and of these, tertiary alkyl ester-type acid-dissociable, dissolution-inhibiting groups are preferable.

In formula (a1-0-2), R is the same as defined above.

$X^2$ is the same as defined for $X^1$ in formula (a1-0-1).

Examples of the divalent linking group for $Y^2$ include alkylene groups, divalent aliphatic cyclic groups, and divalent linking groups containing a hetero atom.

Examples of the aliphatic cyclic group include the same groups as those exemplified above within the description of the "aliphatic cyclic group" with the exception that two or more hydrogen atoms have been removed therefrom.

When $Y^2$ represents an alkylene group, the group preferably contains 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, it is particularly desirable that the divalent aliphatic cyclic group is a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples of the divalent linking group containing a hetero atom include —O—, —C(=O)—O—, —C(=O)—, —O—C(=O)—O—, —C(=O)—NH—, —NH— (wherein H may be substituted with a substituent such as an alkyl group or acyl group), —S—, —S(=O)$_2$—, —S(=O)$_2$—O—, and -A-O (oxygen atom)-B— (wherein each of A and B independently represents a divalent hydrocarbon group which may have a substituent).

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ is -A-O—B—, each of A and B independently represents a divalent hydrocarbon group which may have a substituent.

The description that the hydrocarbon group "may have a substituent" means that some or all of the hydrogen atoms within the hydrocarbon group may each be substituted with an atom other than a hydrogen atom or with a group.

The hydrocarbon group for A may be either an aliphatic hydrocarbon group or an aromatic hydrocarbon group. An "aliphatic hydrocarbon group" refers to a hydrocarbon group that has no aromaticity.

The aliphatic hydrocarbon group for A may be saturated or unsaturated. In general, the aliphatic hydrocarbon group is preferably saturated.

Specific examples of the aliphatic hydrocarbon group include linear and branched aliphatic hydrocarbon groups, and aliphatic hydrocarbon groups containing a ring in the structure thereof.

The linear or branched aliphatic hydrocarbon group preferably has 1 to 10 carbon atoms, more preferably 1 to 8 carbon atoms, still more preferably 2 to 5 carbon atoms, and most preferably 2 carbon atoms.

As the linear aliphatic hydrocarbon group, a linear alkylene group is preferable, and specific examples thereof include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated lower alkyl group of 1 to 5 carbon atoms, and an oxygen atom (=O).

Examples of the hydrocarbon group containing a ring include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an aforementioned chain-like aliphatic hydrocarbon group or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Specific examples of the monocycloalkane include cyclopentane and cyclohexane. As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon group may or may not have a substituent. Examples of the substituent include lower alkyl groups of 1 to 5 carbon atoms, a fluorine atom, fluorinated lower alkyl groups of 1 to 5 carbon atoms, and an oxygen atom (=O).

As the group A, a linear aliphatic hydrocarbon group is preferred, a linear alkylene group is more preferred, a linear alkylene group of 2 to 5 carbon atoms is still more preferred, and an ethylene group is the most desirable.

Examples of the aromatic hydrocarbon group for A include divalent aromatic hydrocarbon groups in which an additional hydrogen atom has been removed from the aromatic hydrocarbon nucleus of a monovalent aromatic hydrocarbon group such as a phenyl group, biphenylyl group, fluorenyl group, naphthyl group, anthryl group or phenanthryl group; aromatic hydrocarbon groups in which a portion of the carbon atoms that constitute the ring of an aforementioned divalent aromatic hydrocarbon group have been substituted with a hetero atom such as an oxygen atom, sulfur atom or nitrogen atom; and aromatic hydrocarbon groups in which an additional hydrogen atom has been removed from the aromatic hydrocarbon nucleus of an arylalkyl group such as a benzyl group, phenethyl group, 1-naphthylmethyl group, 2-naphthylmethyl group, 1-naphthylethyl group or 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

Examples of the hydrocarbon group for B include the same divalent hydrocarbon groups as those listed above for A.

As the group B, a linear or branched aliphatic hydrocarbon group is preferred, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 10]

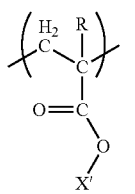

(a1-1)

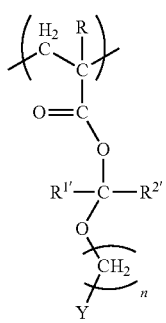

(a1-2)

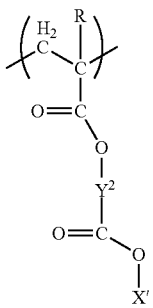

(a1-3)

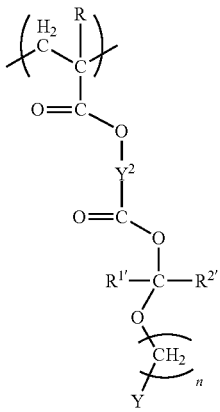

(a1-4)

In the formulas, X' represents a tertiary alkyl ester-type acid-dissociable, dissolution-inhibiting group, Y represents a lower alkyl group of 1 to 5 carbon atoms or an aliphatic cyclic group, n represents an integer of 0 to 3, $Y^2$ represents a divalent linking group, R is the same as defined above, and each of $R^{1\prime}$ and $R^{2\prime}$ independently represents a hydrogen atom or a lower alkyl group of 1 to 5 carbon atoms.

In the formulas, examples of the tertiary alkyl ester-type acid-dissociable, dissolution-inhibiting group for X' include the same tertiary alkyl ester-type acid-dissociable, dissolution-inhibiting groups as those described above for $X^1$ Examples of $R^{1\prime}$, $R^{2\prime}$, n and Y include the same groups and numbers as those listed above for $R^{1\prime}$, $R^{2\prime}$, n and Y in general formula (p1) described above in connection with the "acetal-type acid-dissociable, dissolution-inhibiting groups".

Examples of $Y^2$ include the same groups as those listed above for $Y^2$ in general formula (a1-0-2).

Specific examples of the structural units represented by general formulas (a1-1) to (a1-4) are shown below.

In each of the following formulas, $R^\alpha$ represents a hydrogen atom, a methyl group or a trifluoromethyl group.

[Chemical Formula 11]

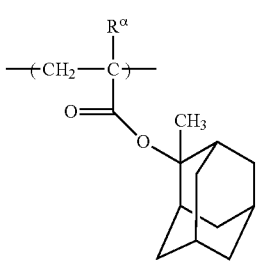

(a1-1-1)

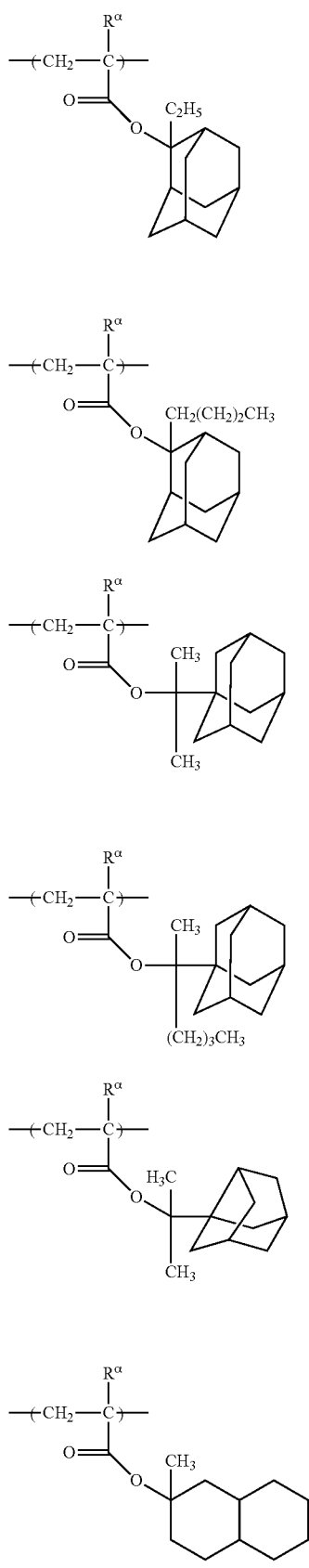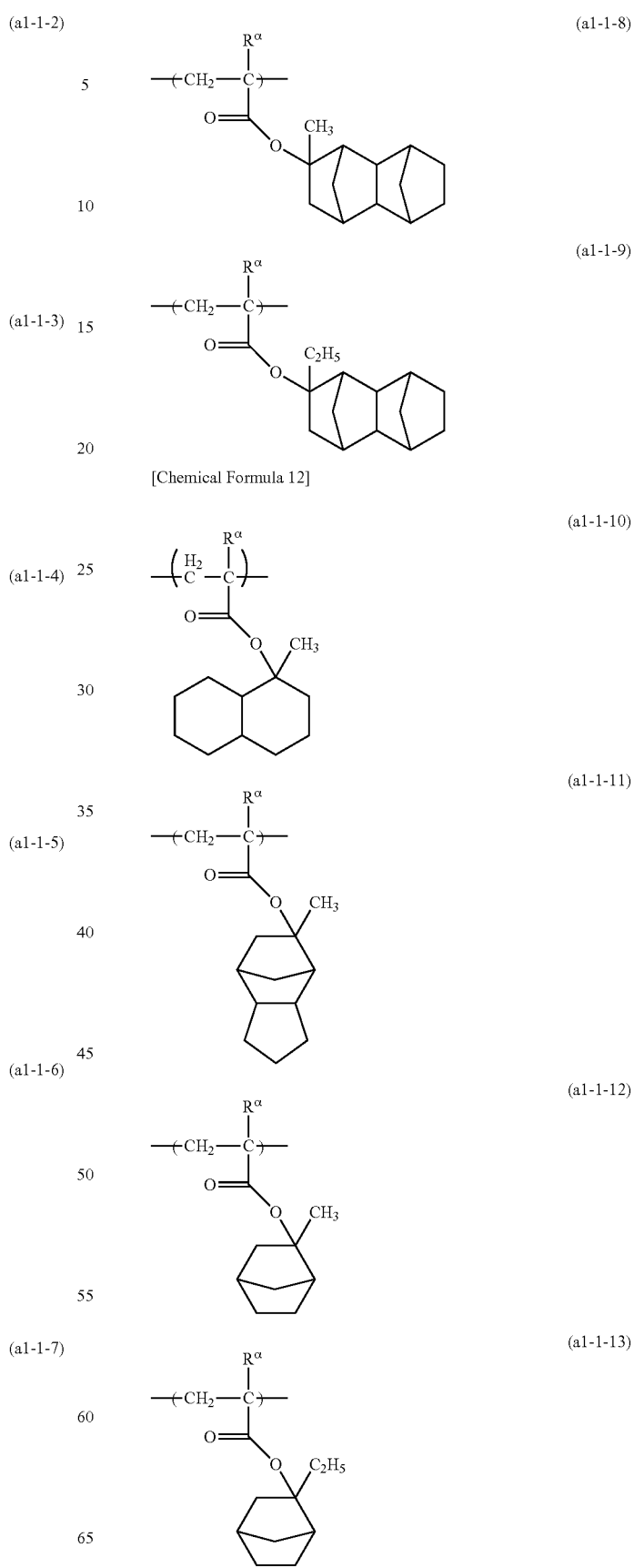
[Chemical Formula 12]

(a1-1-14)
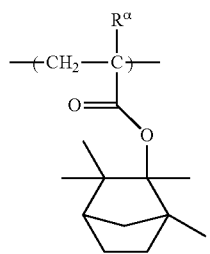
(a1-1-15)
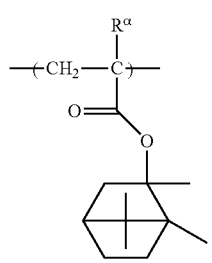
(a1-1-16)
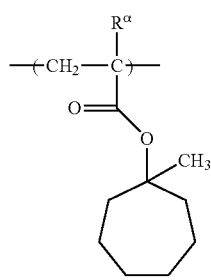
(a1-1-17)
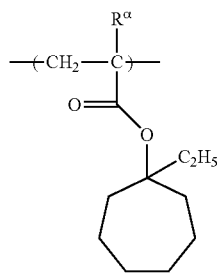
(a1-1-18)
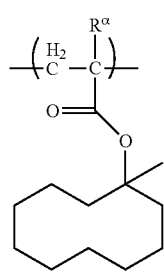
(a1-1-19)
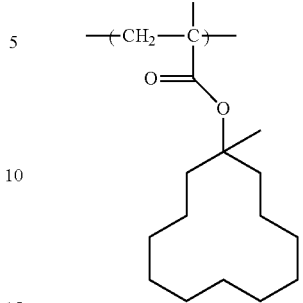
(a1-1-20)
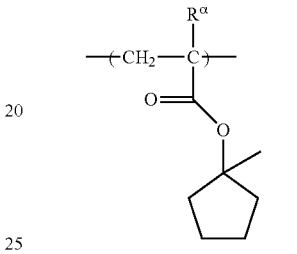
(a1-1-21)
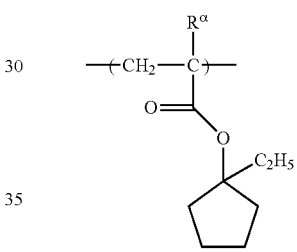
[Chemical Formula 13]
(a1-1-22)
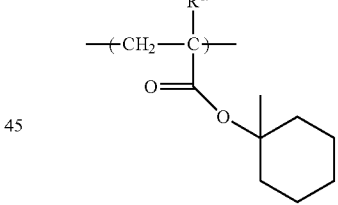
(a1-1-23)
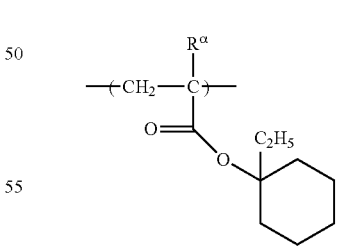
(a1-1-24)
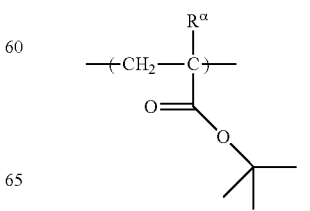

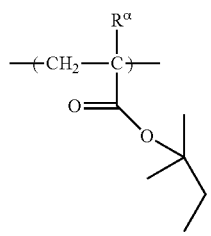 (a1-1-25)
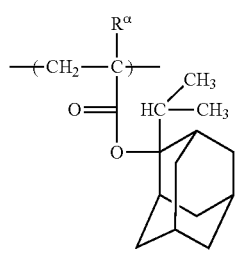 (a1-1-26)
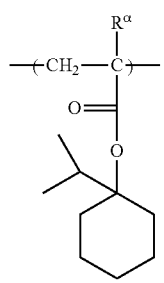 (a1-1-27)
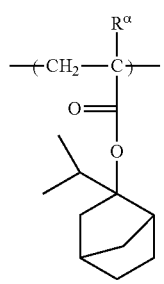 (a1-1-28)
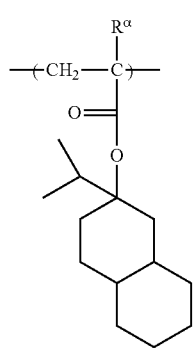 (a1-1-29)
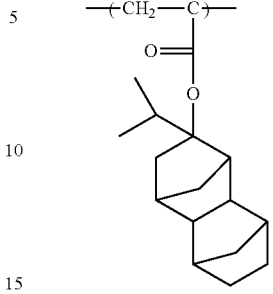 (a1-1-30)
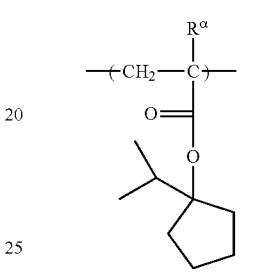 (a1-1-31)
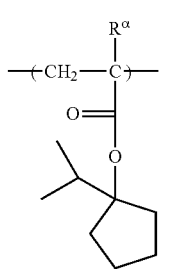 (a1-1-32)
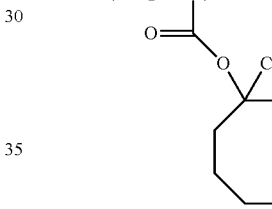 (a1-1-33)
[Chemical Formula 14]
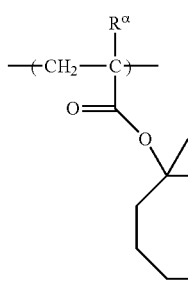 (a1-2-1)
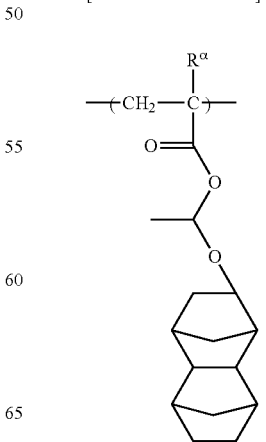

(a1-2-2)
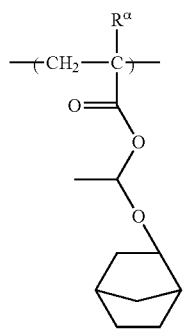
(a1-2-3)
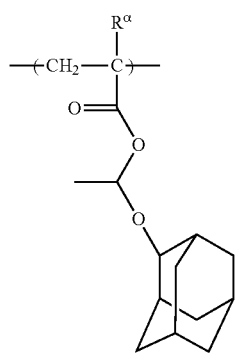
(a1-2-4)
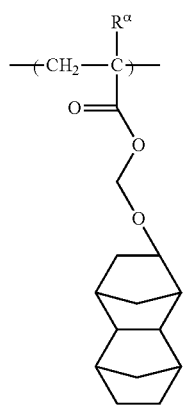
(a1-2-5)
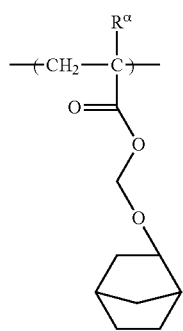
(a1-2-6)
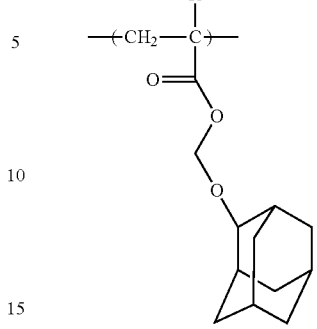
(a1-2-7)
(a1-2-8)
(a1-2-9)
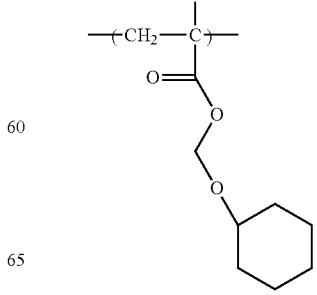

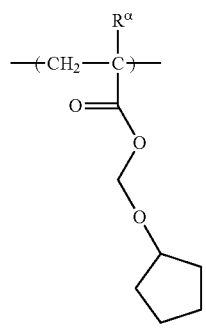
(a1-2-10)
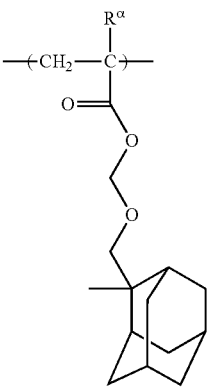
(a1-2-14)
(a1-2-11)
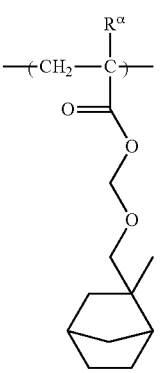
(a1-2-15)
(a1-2-12)
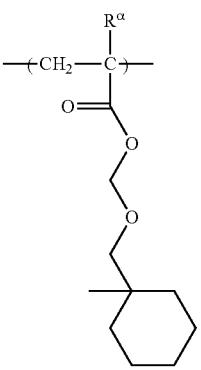
(a1-2-16)
(a1-2-13)
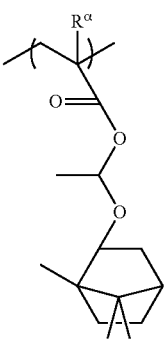
(a1-2-17)

(a1-2-18)
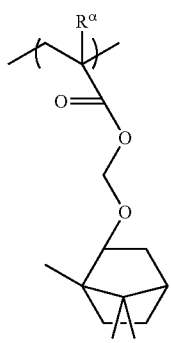
(a1-2-19)
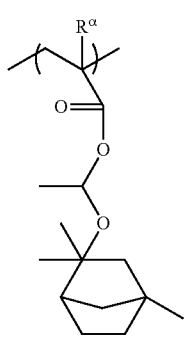
(a1-2-20)
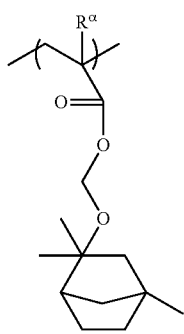
(a1-2-21)
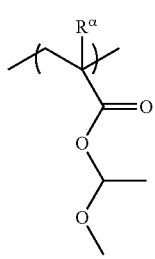
(a1-2-22)
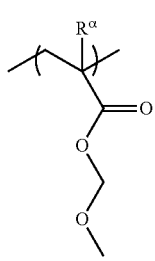
(a1-2-23)
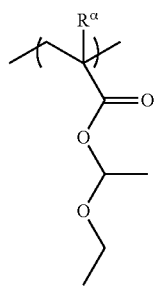
(a1-2-24)
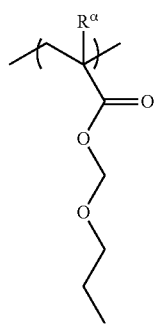
[Chemical Formula 15]
(a1-3-1)
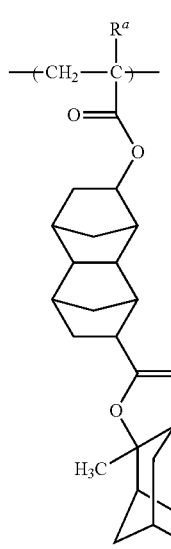

(a1-3-2)
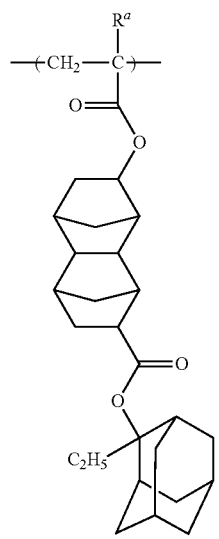
(a1-3-3)
(a1-3-4)
(a1-3-5)
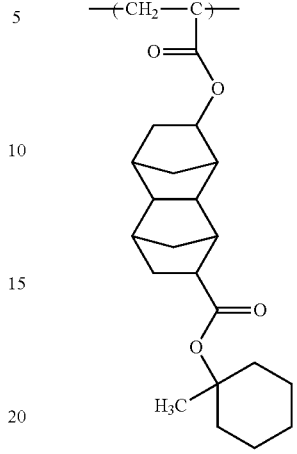
(a1-3-6)
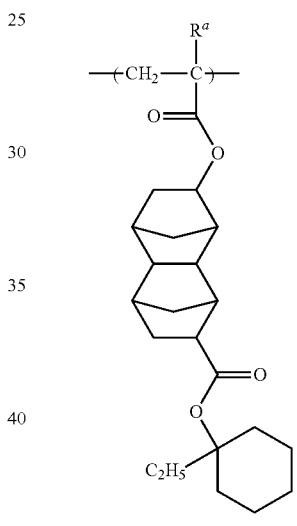
(a1-3-7)
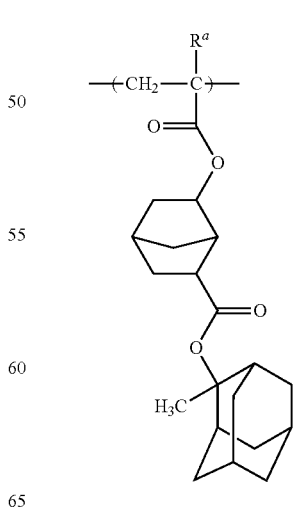

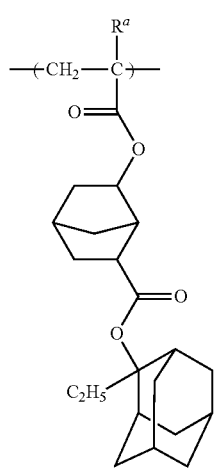
(a1-3-8)
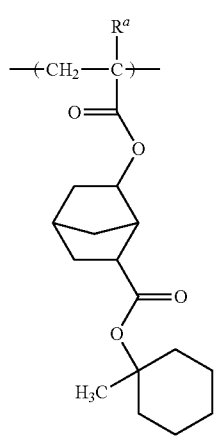
(a-1-3-9)
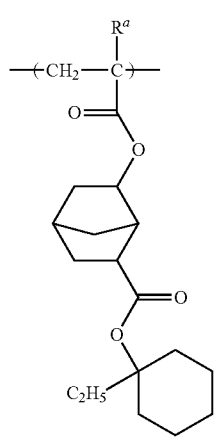
(a1-3-10)
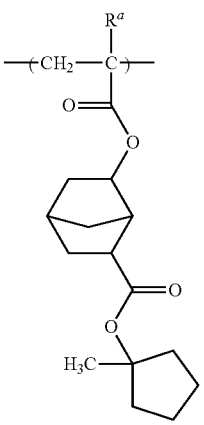
(a1-3-11)
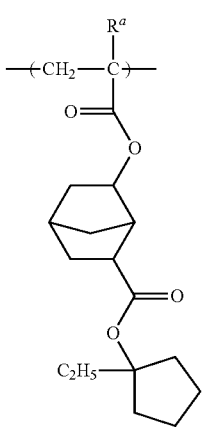
(a1-3-12)
(a1-3-13)
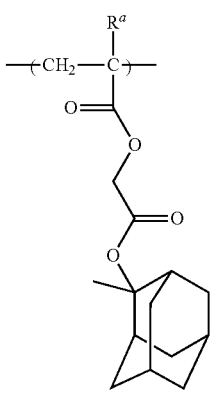
(a1-3-14)

(a1-3-15)
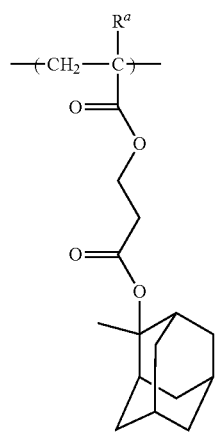
(a1-3-16)
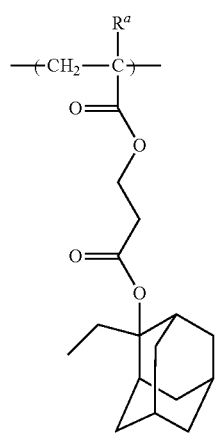
(a1-3-17)
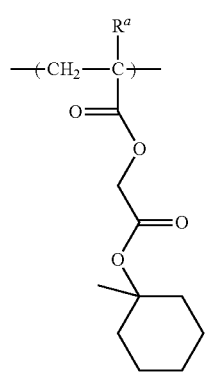
(a1-3-18)
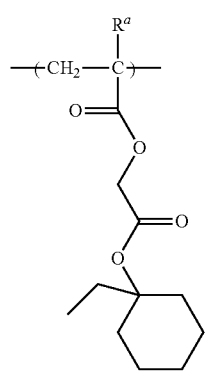
[Chemical Formula 16]
(a1-3-19)
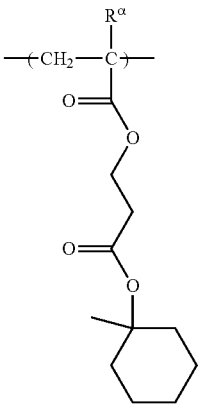
(a1-3-20)
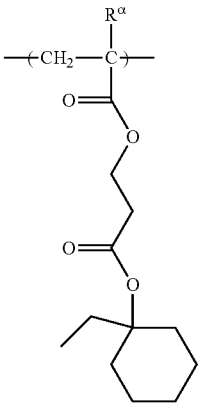
(a1-3-21)
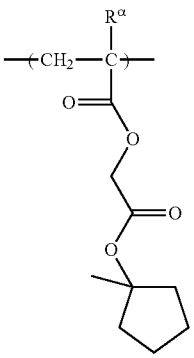
(a1-3-22)
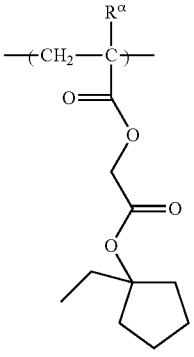

(a1-3-23)
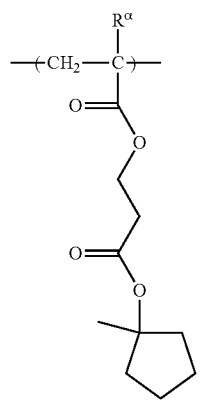
(a1-3-24)
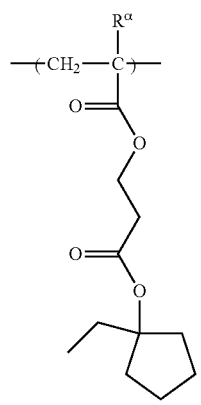
[Chemical Formula 17]
(a1-3-25)
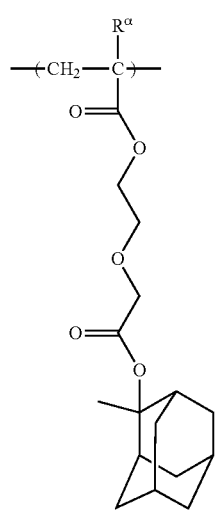
(a1-3-26)
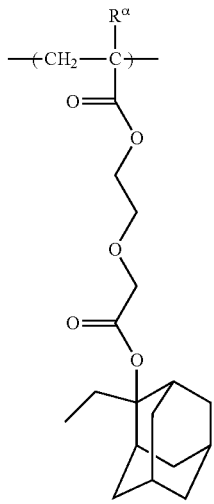
(a1-3-27)
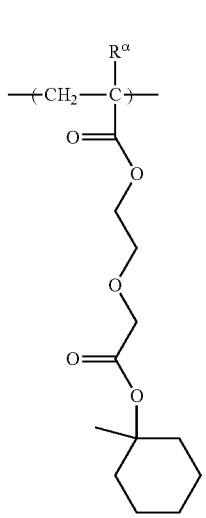
(a1-3-28)
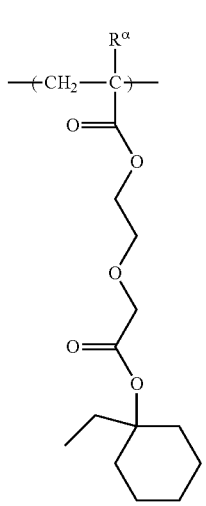

(a1-3-29)
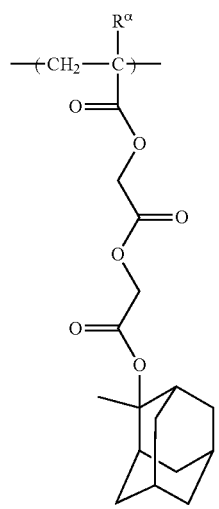
(a1-3-30)
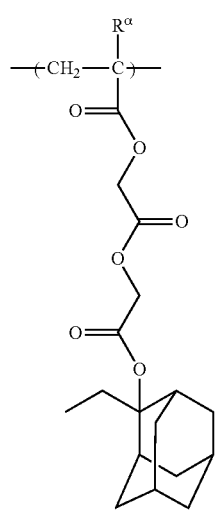
(a1-3-31)
(a1-3-32)
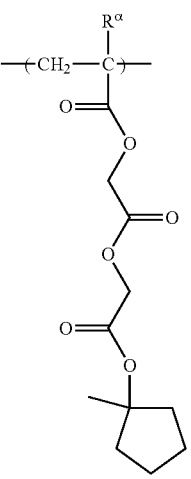
[Chemical Formula 18]
(a1-4-1)
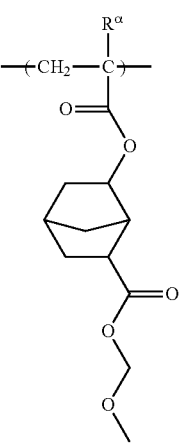
(a1-4-2)
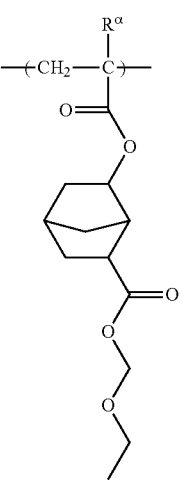

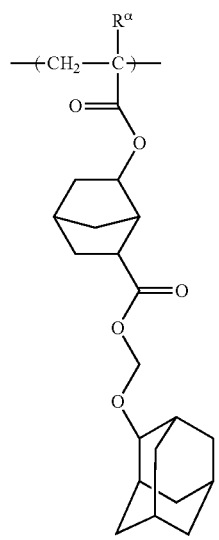
(a1-4-3)
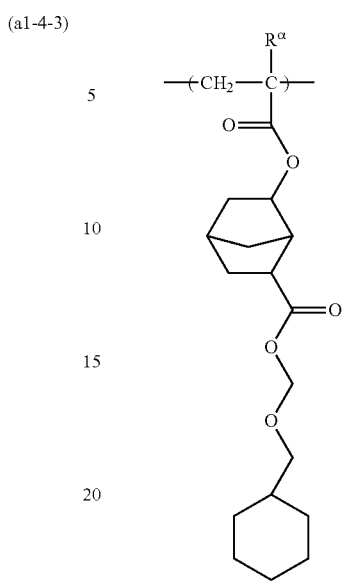
(a1-4-6)
(a1-4-4)
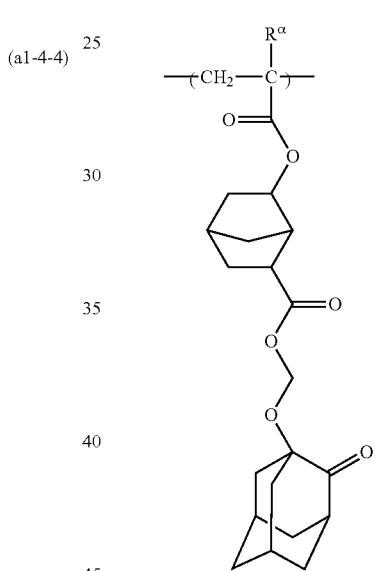
(a1-4-7)
(a1-4-5)
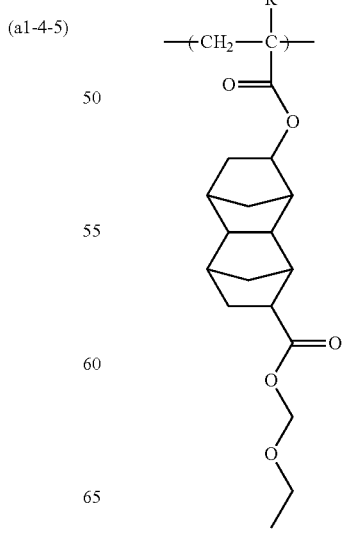
(a1-4-8)

(a1-4-9)
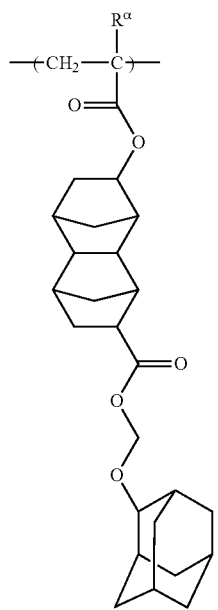
(a1-4-11)
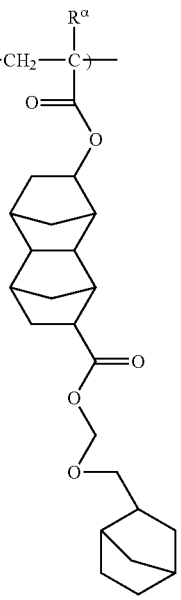
(a1-4-10)
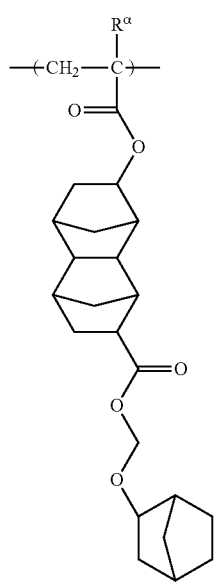
(a1-4-12)
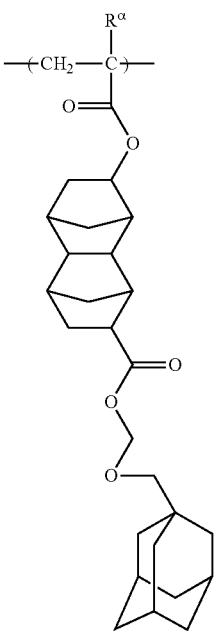

(a1-4-13)

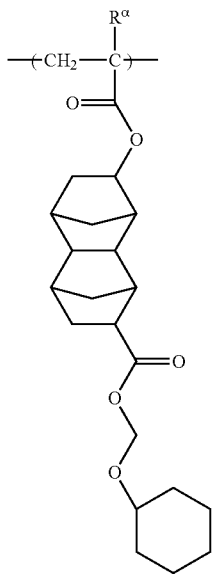

(a1-4-14)

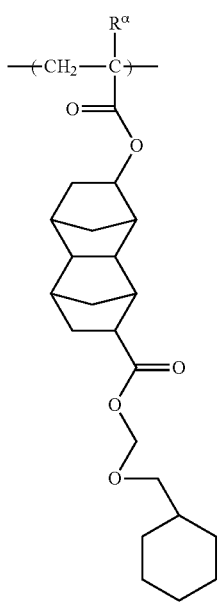

(a1-4-15)

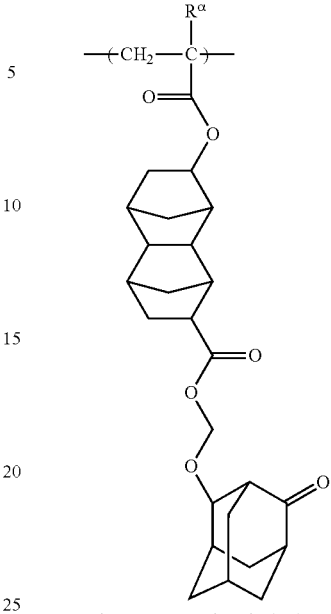

As the structural unit (a1), one type of structural unit may be used alone, or two or more types of structural units may be used in combination.

Among these, structural units represented by general formula (a1-1) or (a1-3) are preferable, and more specifically, the use of at least one structural unit selected from the group consisting of structural units represented by formulas (a1-1-1) to (a1-1-4), formulas (a1-1-16) to (a1-1-17), formulas (a1-1-20) to (a1-1-23), formula (a1-1-26), formulas (a1-1-32) to (a1-1-33), and formulas (a1-3-25) to (a1-3-28) is more preferable.

Moreover, as the structural unit (a1), structural units represented by general formula (a1-1-01) shown below, which includes the structural units represented by formulas (a1-1-1) to (a1-1-3) and formula (a1-1-26), structural units represented by general formula (a1-1-02) shown below, which includes the structural units represented by formulas (a1-1-16) to (a1-1-17), formulas (a1-1-20) to (a1-1-23) and formulas (a1-1-32) to (a1-1-33), structural units represented by general formula (a1-3-01) shown below, which includes the structural units represented by formulas (a1-3-25) to (a1-3-26), structural units represented by general formula (a1-3-02) shown below, which includes the structural units represented by formulas (a1-3-27) to (a1-3-28), structural units represented by general formula (a1-3-03-1) shown below, which includes the structural units represented by formulas (a1-3-29) and (a1-3-31), and structural units represented by general formula (a1-3-03-2) shown below, which includes the structural units represented by formulas (a1-3-30) and (a1-3-32), are preferred.

[Chemical Formula 19]

(a1-1-01)

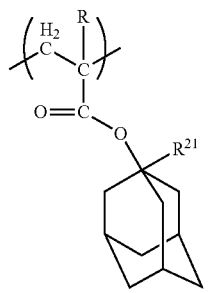

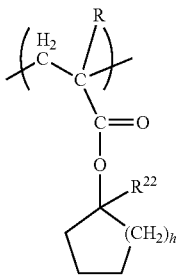

(a1-1-02)

In the formulas, R represents a hydrogen atom, a lower alkyl group or a halogenated lower alkyl group, $R^{21}$ represents a lower alkyl group, $R^{22}$ represents a lower alkyl group, and h represents an integer of 1 to 6.

In general formula (a1-1-01), R is the same as defined above.

The lower alkyl group for $R^{21}$ is the same as defined above for the lower alkyl group for R, is preferably a linear or branched alkyl group, and is most preferably a methyl group or an ethyl group.

In general formula (a1-1-02), R is the same as defined above.

The lower alkyl group for $R^{22}$ is the same as defined above for the lower alkyl group for R, is preferably a linear or branched alkyl group, and is most preferably a methyl group or an ethyl group.

h is preferably 1 or 2.

[Chemical Formula 20]

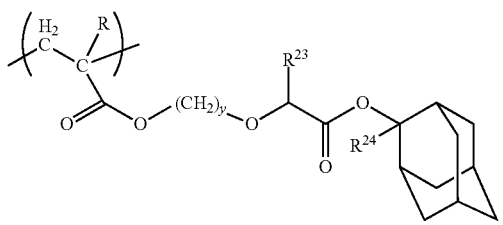

(a1-3-01)

In this formula, R represents a hydrogen atom, a lower alkyl group or a halogenated lower alkyl group, $R^{24}$ represents a lower alkyl group, $R^{23}$ represents a hydrogen atom or a methyl group, and y represents an integer of 1 to 10.

[Chemical Formula 21]

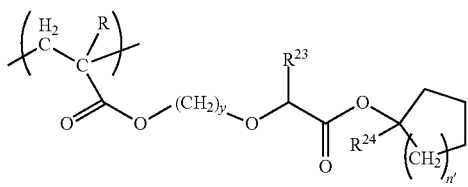

(a1-3-02)

In the formula, R represents a hydrogen atom, a lower alkyl group or a halogenated lower alkyl group, $R^{24}$ represents a lower alkyl group, $R^{23}$ represents a hydrogen atom or a methyl group, y represents an integer of 1 to 10, and n' represents an integer of 1 to 6.

In general formulas (a1-3-01) and (a1-3-02), R is the same as defined above.

$R^{23}$ is preferably a hydrogen atom.

The lower alkyl group for $R^{24}$ is the same as the lower alkyl group defined above for R, and is preferably a methyl group or an ethyl group.

y is preferably an integer of 1 to 8, more preferably an integer of 2 to 5, and most preferably 2.

[Chemical Formula 22]

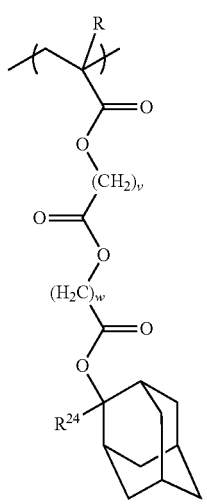

(a1-3-03-1)

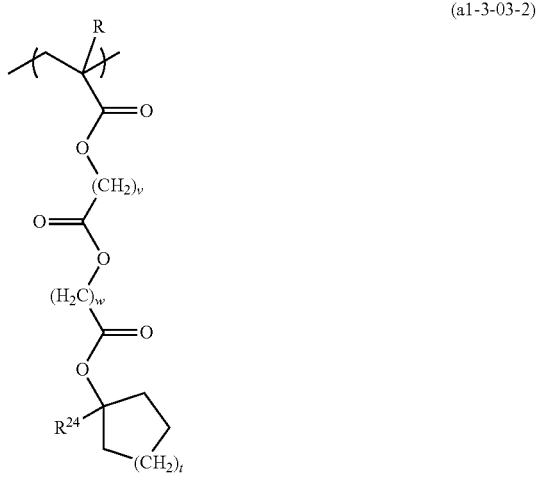

(a1-3-03-2)

In the formulas, R and $R^{24}$ are the same as defined above, v represents an integer of 1 to 10, w represents an integer of 1 to 10, and t represents an integer of 0 to 3.

v is preferably an integer of 1 to 5, and most preferably 1 or 2.

w is preferably an integer of 1 to 5, and most preferably 1 or 2.

t is preferably an integer of 1 to 3, and most preferably 1 or 2.

In the component (A1), the amount of the structural unit (a1), based on the combined total of all the structural units that constitute the component (A1), is preferably within a range from 10 to 80 mol %, more preferably from 20 to 70 mol %, and still more preferably from 25 to 50 mol %. By ensuring that the amount of the structural unit (a1) is at least as large as the lower limit of the above range, a pattern can be formed easily using a resist composition prepared from the component (A1), whereas by ensuring that the amount is not more than the upper limit of the above range, a good balance can be achieved with the other structural units.

(Structural Unit (a2))

The structural unit (a2) is a structural unit which is derived from an acrylate ester that may have an atom other than a hydrogen atom or a substituent bonded to the carbon atom on the α-position, and contains a lactone-containing cyclic group.

The term "lactone-containing cyclic group" refers to a cyclic group including one ring containing a —O—C(=O)— structure (the lactone ring). This "lactone ring" is counted as the first ring, so that a lactone-containing cyclic group in which the only ring structure is the lactone ring is referred to as a monocyclic group, and groups that also contain other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with developing solutions containing water.

There are no particular limitations on the structural unit (a2), and an arbitrary structural unit may be used.

Specific examples of lactone-containing monocyclic groups include groups in which one hydrogen atom has been removed from a 4- to 6-membered lactone ring, including a group in which one hydrogen atom has been removed from β-propiolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 23]

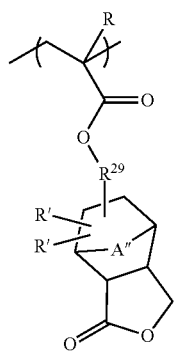
(a2-1)

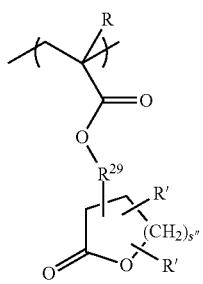
(a2-2)

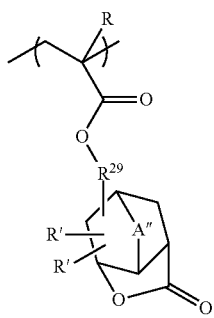
(a2-3)

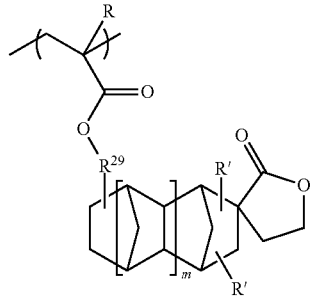
(a2-4)

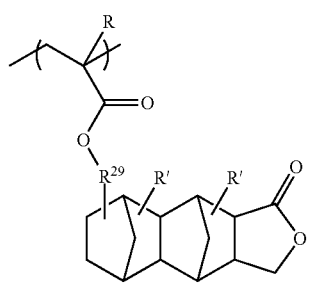
(a2-5)

In the formulas, R represents a hydrogen atom, a lower alkyl group or a halogenated lower alkyl group, each R' independently represents a hydrogen atom, an alkyl group of 1 to 5 carbon atoms, an alkoxy group of 1 to 5 carbon atoms or —COOR", wherein R" represents a hydrogen atom or an alkyl group, $R^{29}$ represents a single bond or a divalent linking group, s" represents an integer of 0 to 2, A" represents an oxygen atom, a sulfur atom or an alkylene group of 1 to 5 carbon atoms which may contain an oxygen atom or a sulfur atom, and m represents 0 or 1.

In general formulas (a2-1) to (a2-5), R is the same as defined for R in the structural unit (a1).

Examples of the alkyl group of 1 to 5 carbon atoms for R' include a methyl group, ethyl group, propyl group, n-butyl group or tert-butyl group.

Examples of the alkoxy group of 1 to 5 carbon atoms for R' include a methoxy group, ethoxy group, n-propoxy group, iso-propoxy group, n-butoxy group or tert-butoxy group.

In terms of industrial availability, R' is preferably a hydrogen atom.

R" is preferably a hydrogen atom or a linear, branched or cyclic alkyl group of 1 to 15 carbon atoms.

When R" is a linear or branched alkyl group, the alkyl group preferably has 1 to 10 carbon atoms, and more preferably 1 to 5 carbon atoms.

When R" represents a cyclic alkyl group (cycloalkyl group), the cycloalkyl group preferably has 3 to 15 carbon atoms, more preferably 4 to 12 carbon atoms, and most preferably 5 to 10 carbon atoms. Examples of the cycloalkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

A" is preferably an alkylene group of 1 to 5 carbon atoms or —O—, is more preferably an alkylene group of 1 to 5 carbon atoms, and is most preferably a methylene group.

$R^{29}$ represents a single bond or a divalent linking group. Examples of the divalent linking group include the same divalent linking groups as those described above for $Y^2$ in general formula (a1-0-2), and of these groups, an alkylene group, an ester linkage (—C(=O)—O—) or a combination thereof is preferred. The alkylene group for the divalent linking group for $R^{29}$ is preferably a linear or branched alkylene group. Specific examples include the same linear alkylene groups and branched alkylene groups as those listed above for the aliphatic hydrocarbon group for A within the description for $Y^2$.

s" is preferably an integer of 1 or 2.

Specific examples of the structural units represented by general formulas (a2-1) to (a2-5) are shown below.

In each of the following formulas, $R^\alpha$ represents a hydrogen atom, a methyl group or a trifluoromethyl group.

[Chemical Formula 24]

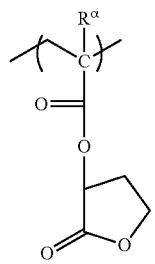

(a2-1-1)

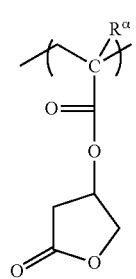

(a2-1-2)

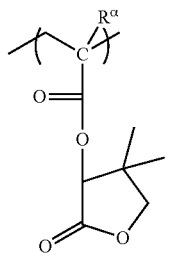

(a2-1-3)

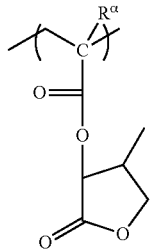

(a2-1-4)

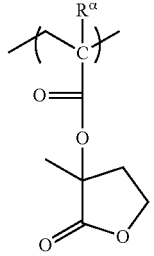

(a2-1-5)

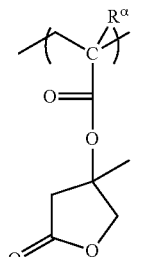

(a2-1-6)

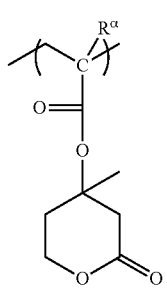

(a2-1-7)

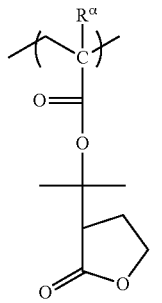

(a2-1-8)

(a2-1-9)
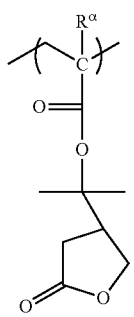
(a2-1-10)
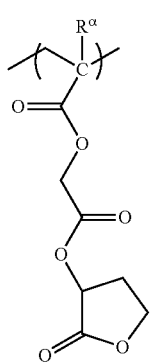
(a2-1-11)
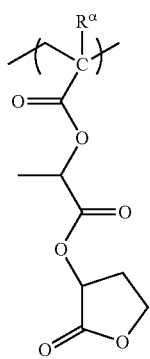
(a2-1-12)
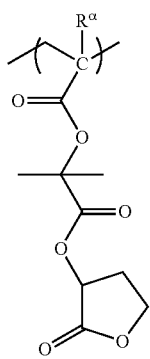
(a2-1-13)
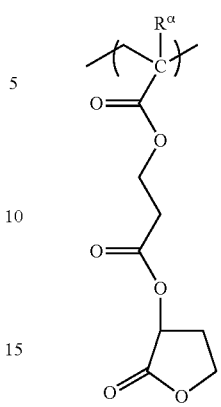
[Chemical Formula 25]
(a2-2-1)
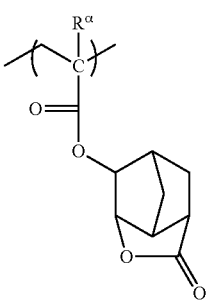
(a2-2-2)
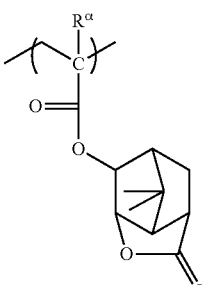
(a2-2-3)
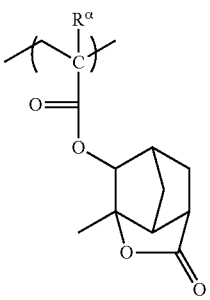
(a2-2-4)
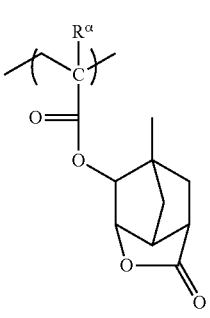

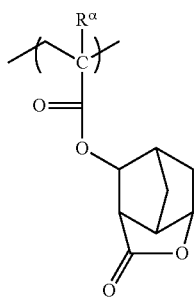
(a2-2-5)
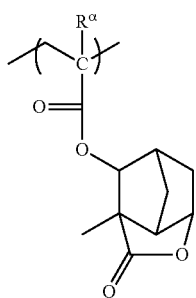
(a2-2-6)
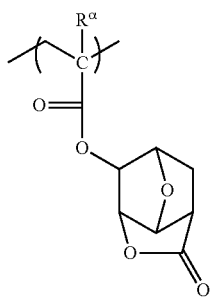
(a2-2-7)
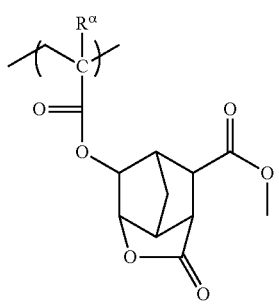
(a2-2-8)
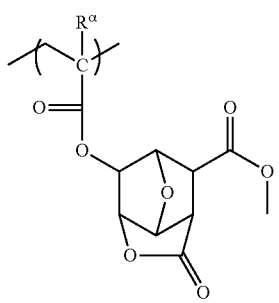
(a2-2-9)
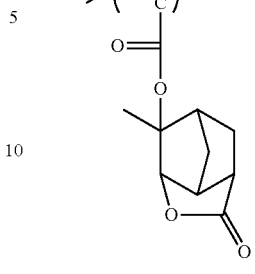
(a2-2-10)
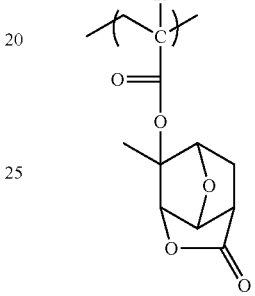
(a2-2-11)
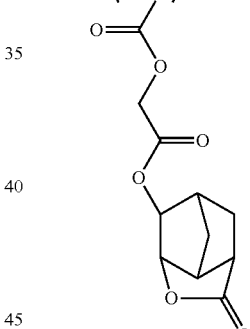
(a2-2-12)
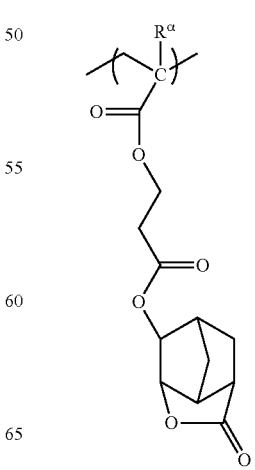
(a2-2-13)

(a2-2-14)
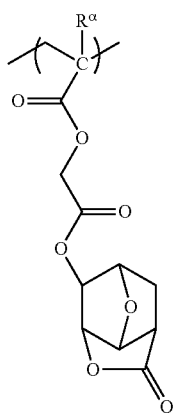
(a2-2-15)
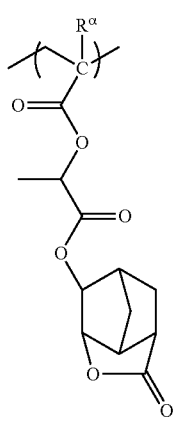
(a2-2-16)
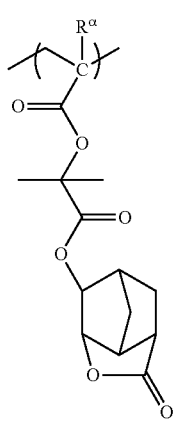
(a2-2-17)
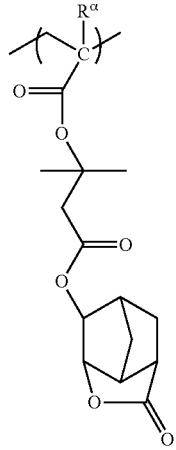
[Chemical Formula 26]
(a2-3-1)
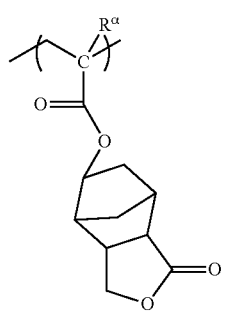
(a2-3-2)
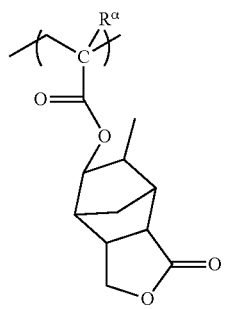
(a2-3-3)
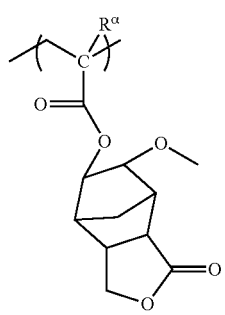

(a2-3-4) 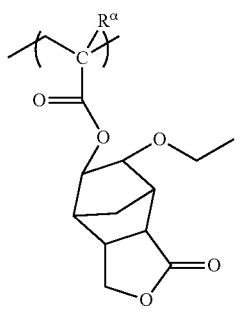
(a2-3-5) 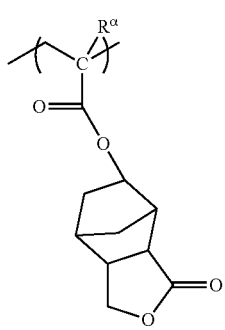
[Chemical Formula 27]
(a2-4-1) 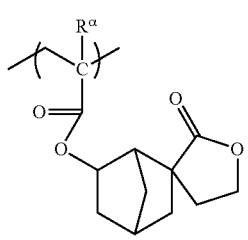
(a2-4-2) 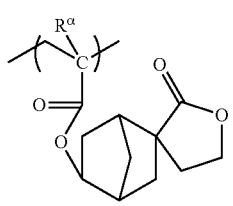
(a2-4-3) 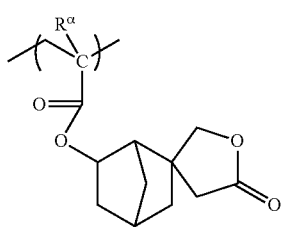
(a2-4-4) 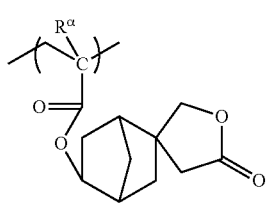
(a2-4-5) 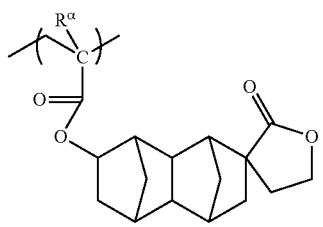
(a2-4-6) 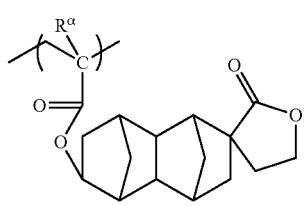
(a2-4-7) 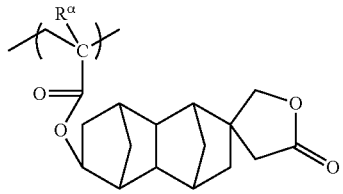
(a2-4-8) 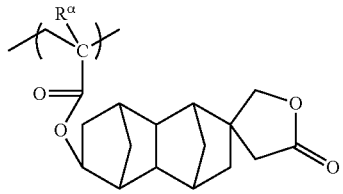
(a2-4-9) 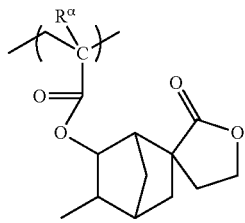
(a2-4-10) 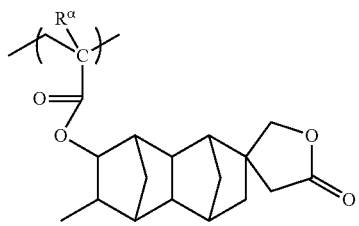

(a2-4-11)
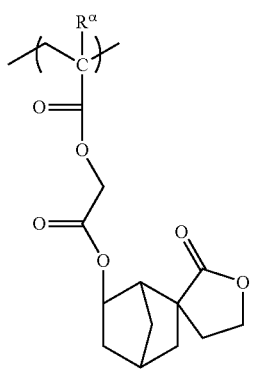
(a2-4-12)
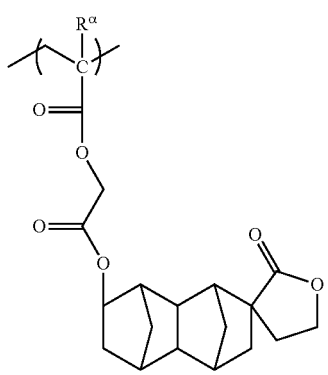
[Chemical Formula 28]
(a2-5-1)
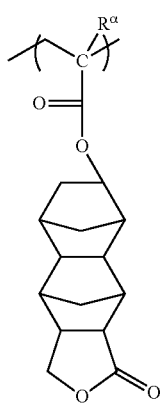
(a2-5-2)
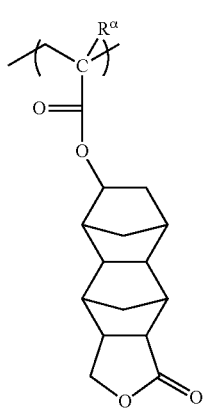
(a2-5-3)
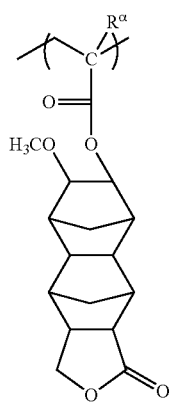
(a2-5-4)
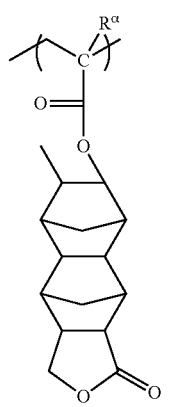
(a2-5-5)
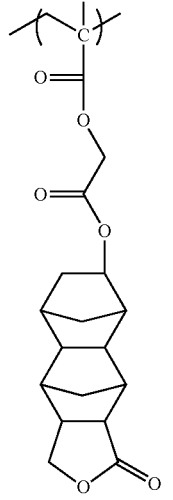

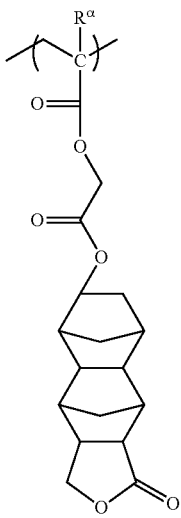

(a2-5-6)

In the component (A1), as the structural unit (a2), one type of structural unit may be used alone, or two or more types of structural units may be used in combination.

The structural unit (a2) is preferably at least one structural unit selected from the group consisting of structural units represented by general formulas (a2-1) to (a2-5), and is more preferably at least one structural unit selected from the group consisting of structural units represented by general formulas (a2-1) to (a2-3). Of these, it is particularly preferable to use at least one structural unit selected from the group consisting of the structural units represented by chemical formulas (a2-1-1), (a2-1-2), (a2-2-1), (a2-2-7), (a2-3-1) and (a2-3-5).

The amount of the structural unit (a2) within the component (A1), based on the combined total of all the structural units that constitute the component (A1), is preferably within a range from 5 to 60 mol %, more preferably from 10 to 50 mol %, and most preferably from 10 to 45 mol %. By ensuring that the amount of the structural unit (a2) is at least as large as the lower limit of the above range, the effects generated by including the structural unit (a2) are obtained satisfactorily, whereas by ensuring that the amount is not more than the upper limit of the above range, a good balance can be achieved with the other structural units.

(Structural Unit (a3))

The structural unit (a3) is a structural unit which is derived from an acrylate ester that may have an atom other than a hydrogen atom or a substituent bonded to the carbon atom on the α-position, and contains a polar group-containing aliphatic hydrocarbon group.

By including the structural unit (a3) within the component (A1), the hydrophilicity of the component (A) is improved, and the compatibility of the component (A) with the developing solution is improved. As a result, the alkali solubility of the exposed portions improves, which contributes to an improvement in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and cyclic aliphatic hydrocarbon groups (cyclic groups). These cyclic groups may be either monocyclic or polycyclic, and can be selected appropriately from the multitude of groups that have been proposed for the resins of resist compositions designed for use with ArF excimer lasers. The cyclic group is preferably a polycyclic group, which more preferably contains 7 to 30 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 29]

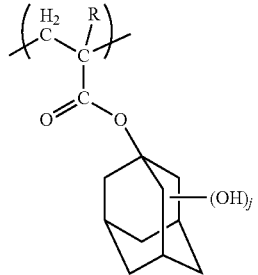

(a3-1)

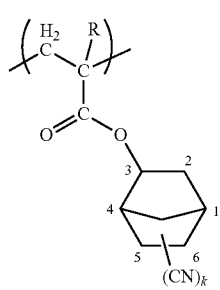

(a3-2)

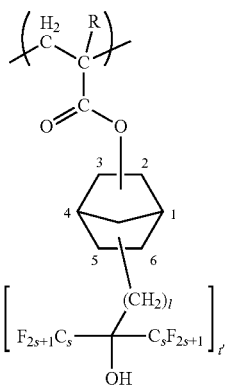

(a3-3)

In the formulas, R is the same as defined above, j is an integer of 1 to 3, k is an integer of 1 to 3, t' is an integer of 1 to 3, l is an integer of 1 to 5, and s is an integer of 1 to 3.

In formula (a3-1), j is preferably 1 or 2, and more preferably 1. When j is 2, it is preferable that the hydroxyl groups are bonded to the 3rd and 5th positions of the adamantyl group. When j is 1, it is preferable that the hydroxyl group is bonded to the 3rd position of the adamantyl group.

j is preferably 1, and it is particularly desirable that the hydroxyl group is bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group is bonded to the terminal of the carboxyl group of the acrylic acid. The fluorinated alkyl alcohol is preferably bonded to the 5th or 6th position of the norbornyl group.

As the structural unit (a3), one type of structural unit may be used alone, or two or more types may be used in combination.

The amount of the structural unit (a3) within the component (A1), based on the combined total of all the structural units that constitute the component (A1), is preferably within a range from 5 to 50 mol %, more preferably from 5 to 40 mol %, and still more preferably from 5 to 25 mol %. By ensuring that the amount of the structural unit (a3) is at least as large as the lower limit of the above range, the effects generated by including the structural unit (a3) are obtained satisfactorily, whereas by ensuring that the amount is not more than the upper limit of the above range, a good balance can be achieved with the other structural units.

(Structural Unit (a0))

The structural unit (a0) is a structural unit which is derived from an acrylate ester that may have an atom other than a hydrogen atom or a substituent bonded to the carbon atom on the α-position, and contains an —SO$_2$-containing cyclic group.

By incorporating an —SO$_2$-containing cyclic group, the structural unit (a0) enhances the adhesion between the substrate and a resist film formed using a resist composition containing the component (A1). Further, the structural unit (a0) also contributes to improvements in lithography properties such as the sensitivity, resolution, exposure margin (EL margin), line width roughness (LWR), line edge roughness (LER), and mask reproducibility.

In this description, the term "—SO$_2$-containing cyclic group" refers to a cyclic group which includes a ring containing an —SO$_2$— moiety within the ring structure, and specifically refers to cyclic groups in which the sulfur atom (S) of the —SO$_2$— forms a part of the ring structure of the cyclic group.

In the —SO$_2$-containing cyclic group, the ring containing the —SO$_2$— moiety within the ring structure is counted as the first ring, so that groups containing only that ring are referred to as monocyclic groups, and groups containing other ring structures are described as polycyclic groups regardless of the structure of the other rings.

The —SO$_2$-containing cyclic group may be either monocyclic or polycyclic.

The —SO$_2$-containing cyclic group is preferably a cyclic group containing an —O—SO$_2$-moiety within the ring structure, namely a cyclic group containing a sultone ring in which the —O—S— within the —O—SO$_2$— forms a part of the ring structure.

The —SO$_2$-containing cyclic group preferably contains 3 to 30 carbon atoms, more preferably 4 to 20 carbon atoms, still more preferably 4 to 15 carbon atoms, and most preferably 4 to 12 carbon atoms. Here, the number of carbon atoms refers to the number of carbon atoms that constitute the ring structure, and does not include carbon atoms contained within substituents.

The —SO$_2$-containing cyclic group may be an —SO$_2$-containing aliphatic cyclic group or an —SO$_2$-containing aromatic cyclic group. An —SO$_2$-containing aliphatic cyclic group is preferred.

Examples of the —SO$_2$-containing aliphatic cyclic group include groups in which at least one hydrogen atom has been removed from an aliphatic hydrocarbon ring in which some of the carbon atoms that constitute the ring structure have been substituted with either —SO$_2$— or —O—SO$_2$—. More specific examples include groups in which at least one hydrogen atom has been removed from an aliphatic hydrocarbon ring in which a —CH$_2$-moiety that constitutes part of the ring structure has been substituted with an —SO$_2$-moiety, and groups in which at least one hydrogen atom has been removed from an aliphatic hydrocarbon ring in which a —CH$_2$—CH$_2$— moiety that constitutes part of the ring structure has been substituted with an —O—SO$_2$— moiety.

The alicyclic hydrocarbon group preferably contains 3 to 20 carbon atoms, and more preferably 3 to 12 carbon atoms.

The alicyclic hydrocarbon group may be either polycyclic or monocyclic. As the monocyclic alicyclic hydrocarbon group, groups in which two hydrogen atoms have been removed from a monocycloalkane of 3 to 6 carbon atoms are preferable, and specific examples of such monocycloalkanes include cyclopentane and cyclohexane. As the polycyclic alicyclic hydrocarbon group, groups in which two hydrogen atoms have been removed from a polycycloalkane of 7 to 12 carbon atoms are preferable, and specific examples of such polycycloalkanes include adamantane, norbornane, isobornane, tricyclodecane and tetracyclododecane.

The —SO$_2$-containing cyclic group may have a substituent. Examples of the substituent include an alkyl group, alkoxy group, halogen atom, halogenated alkyl group, hydroxyl group, oxygen atom (=O), —COOR", —OC(=O)R" (wherein R" is a hydrogen atom or an alkyl group), hydroxyalkyl group and cyano group.

The alkyl group for the substituent is preferably an alkyl group of 1 to 6 carbon atoms. The alkyl group is preferably a linear or branched group. Specific examples include a methyl group, ethyl group, propyl group, isopropyl group, n-butyl group, isobutyl group, tert-butyl group, pentyl group, isopentyl group, neopentyl group or hexyl group. Among these, a methyl group or ethyl group is preferred, and a methyl group is particularly desirable.

The alkoxy group for the substituent is preferably an alkoxy group of 1 to 6 carbon atoms. The alkoxy group is preferably a linear or branched group. Specific examples include groups in which an oxygen atom (—O—) is bonded to any of the alkyl groups described above for the alkyl group substituent.

Examples of the halogen atom for the substituent include a fluorine atom, chlorine atom, bromine atom or iodine atom, and a fluorine atom is preferable.

Examples of the halogenated alkyl group for the substituent include groups in which some or all of the hydrogen atoms of an aforementioned alkyl group substituent have been substituted with the above halogen atoms. A fluorinated alkyl group is preferred as the halogenated alkyl group, and a perfluoroalkyl group is particularly desirable.

In the aforementioned —COOR" group and —OC(=O)R" group, R" represents a hydrogen atom, or a linear, branched or cyclic alkyl group of 1 to 15 carbon atoms.

In those cases where R" represents a linear or branched alkyl group, the alkyl group preferably contains 1 to 10 carbon atoms, and more preferably 1 to 5 carbon atoms, and is most preferably a methyl group or ethyl group.

In those cases where R" is a cyclic alkyl group, the alkyl group preferably contains 3 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

The hydroxyalkyl group for the substituent preferably contains 1 to 6 carbon atoms, and specific examples thereof include groups in which at least one hydrogen atom within an aforementioned alkyl group substituent has been substituted with a hydroxyl group.

More specific examples of the —SO$_2$-containing cyclic group include groups represented by general formulas (3-1) to (3-4) shown below.

[Chemical Formula 30]

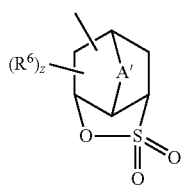

(3-1)

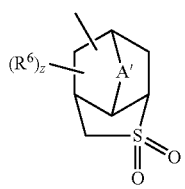

(3-2)

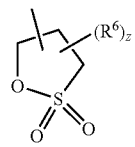

(3-3)

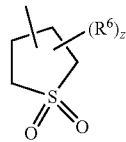

(3-4)

In the formulas, A' represents an oxygen atom, a sulfur atom, or an alkylene group of 1 to 5 carbon atoms which may contain an oxygen atom or a sulfur atom, z represents an integer of 0 to 2, and R$^6$ represents an alkyl group, alkoxy group, halogenated alkyl group, hydroxyl group, —COOR", —OC(=O)R", hydroxyalkyl group or cyano group, wherein R" represents a hydrogen atom or an alkyl group.

In general formulas (3-1) to (3-4) above, A' represents an oxygen atom (—O—), a sulfur atom (—S—), or an alkylene group of 1 to 5 carbon atoms which may contain an oxygen atom or a sulfur atom.

As the alkylene group of 1 to 5 carbon atoms for A', a linear or branched alkylene group is preferable, and examples thereof include a methylene group, ethylene group, n-propylene group and isopropylene group.

Examples of the alkylene groups which contain an oxygen atom or a sulfur atom include the aforementioned alkylene groups in which —O— or —S— is either bonded to the terminal of the alkylene group or interposed within the alkylene group. Specific examples of such alkylene groups include —O—CH$_2$—, —CH$_2$—O—CH$_2$—, —S—CH$_2$— and —CH$_2$—S—CH$_2$—.

A' is preferably an alkylene group of 1 to 5 carbon atoms or —O—, more preferably an alkylene group of 1 to 5 carbon atoms, and most preferably a methylene group.

z represents an integer of 0 to 2, and is most preferably 0.

When z is 2, the plurality of R$^6$ groups may be the same or different from each other.

Examples of the alkyl group, alkoxy group, halogenated alkyl group, —COOR" group, —OC(=O)R" group and hydroxyalkyl group for R$^6$ include the same alkyl groups, alkoxy groups, halogenated alkyl groups, —COOR" groups, —OC(=O)R" groups and hydroxyalkyl groups as those described above for the substituent which the —SO$_2$-containing cyclic group may have.

Specific examples of the cyclic groups represented by general formulas (3-1) to (3-4) are shown below. In the formulas shown below, "Ac" represents an acetyl group.

[Chemical Formula 31]

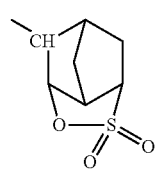

(3-1-1)

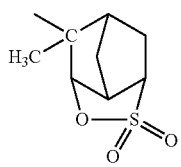 (3-1-2)
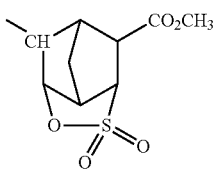 (3-1-10)
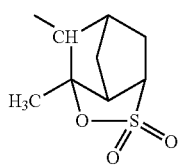 (3-1-3)
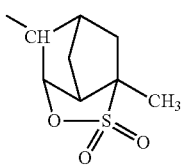 (3-1-11)
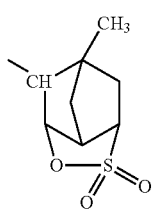 (3-1-4)
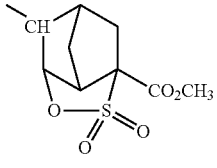 (3-1-12)
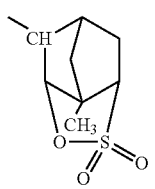 (3-1-5)
[Chemical Formula 32]
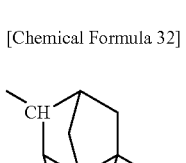 (3-1-13)
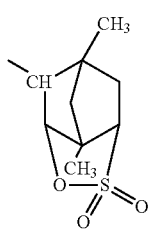 (3-1-6)
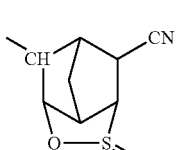 (3-1-14)
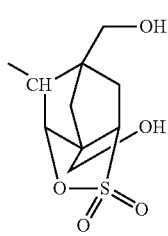 (3-1-7)
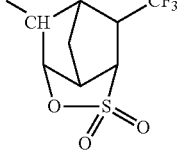 (3-1-15)
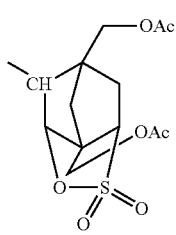 (3-1-8)
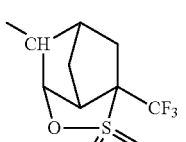 (3-1-16)
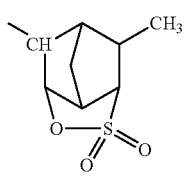 (3-1-9)
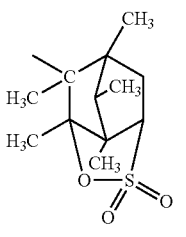 (3-1-17)

-continued
[Chemical Formula 33]
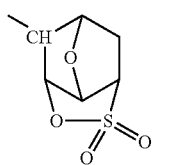
(3-1-18)
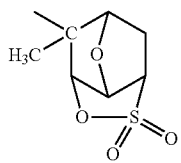
(3-1-19)
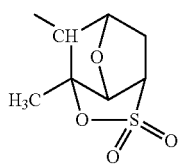
(3-1-20)
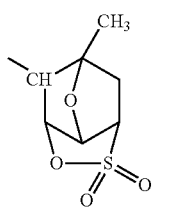
(3-1-21)
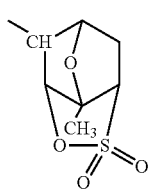
(3-1-22)
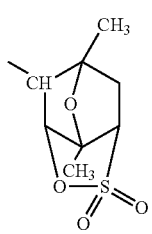
(3-1-23)
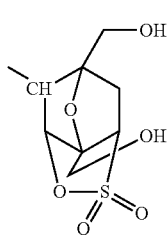
(3-1-24)
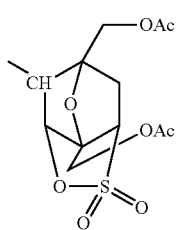
(3-1-25)
[Chemical Formula 34]
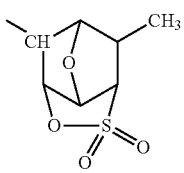
(3-1-26)
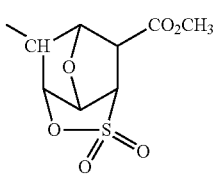
(3-1-27)
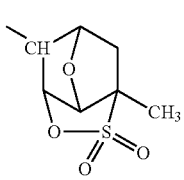
(3-1-28)
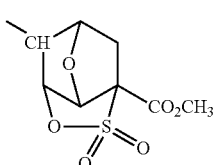
(3-1-29)
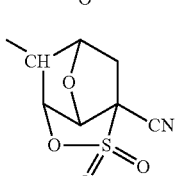
(3-1-30)
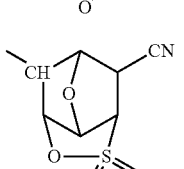
(3-1-31)
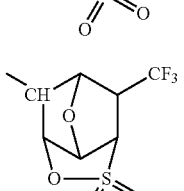
(3-1-32)
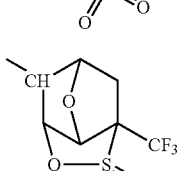
(3-1-33)
[Chemical Formula 35]
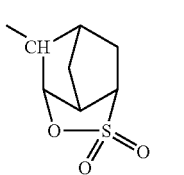
(3-2-1)

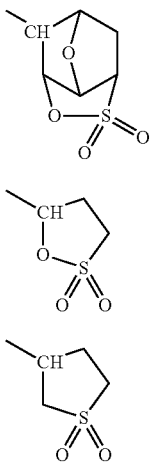

(3-2-2)

(3-3-1)

(3-4-1)

Of the groups shown above, the —SO$_2$-containing cyclic group is preferably a group represented by general formula (3-1), more preferably at least one group selected from the group consisting of groups represented by the above chemical formulas (3-1-1), (3-1-18), (3-3-1) and (3-4-1), and most preferably a group represented by chemical formula (3-1-1).

More specific examples of the structural unit (a0) include structural units represented by general formula (a0-0) shown below.

[Chemical Formula 36]

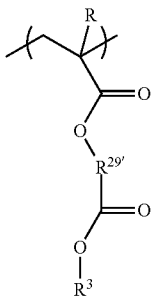

(a0-0)

In the formula, R represents a hydrogen atom, an alkyl group of 1 to 5 carbon atoms or a halogenated alkyl group of 1 to 5 carbon atoms, R$^3$ represents an —SO$_2$-containing cyclic group, and R$^{29'}$ represents a single bond or a divalent linking group.

In the formula (a0-0), R represents a hydrogen atom, an alkyl group of 1 to 5 carbon atoms or a halogenated alkyl group of 1 to 5 carbon atoms.

The alkyl group of 1 to 5 carbon atoms for R is preferably a linear or branched alkyl group of 1 to 5 carbon atoms, and specific examples include a methyl group, ethyl group, propyl group, isopropyl group, n-butyl group, isobutyl group, tert-butyl group, pentyl group, isopentyl group or neopentyl group.

The halogenated alkyl group for R is a group in which some or all of the hydrogen atoms of an aforementioned alkyl group of 1 to 5 carbon atoms have each been substituted with a halogen atom. Examples of the halogen atom include a fluorine atom, a chlorine atom, a bromine atom and an iodine atom. A fluorine atom is particularly desirable.

As R, a hydrogen atom, an alkyl group of 1 to 5 carbon atoms or a fluorinated alkyl group of 1 to 5 carbon atoms is preferable, and in terms of industrial availability, a hydrogen atom or a methyl group is the most desirable.

In formula (a0-0), R$^3$ is the same as the —SO$_2$-containing cyclic group described above.

R$^{29'}$ may be either a single bond or a divalent linking group. A divalent linking group is preferable in terms of achieving superior effects for the present invention.

Examples of the divalent linking group for R$^{29'}$ include the same groups as those described above for R$^{29}$ in connection with the structural unit (a2).

As the divalent linking group for R$^{29'}$, linear or branched alkylene groups, divalent alicyclic hydrocarbon groups, and divalent linking groups containing a hetero atom are preferred. Among these, linear or branched alkylene groups, and divalent linking groups containing a hetero atom are preferable, and linear alkylene groups are particularly desirable.

When R$^{29'}$ is an alkylene group, the alkylene group preferably has 1 to 10 carbon atoms, more preferably 1 to 6 carbon atoms, still more preferably 1 to 4 carbon atoms, and most preferably 1 to 3 carbon atoms. Specific examples include the same groups as the linear alkylene groups and branched alkylene groups mentioned above.

When R$^{29'}$ is a divalent alicyclic hydrocarbon group, examples of the alicyclic hydrocarbon group include the same groups as those described above for the alicyclic hydrocarbon group in connection with the "aliphatic hydrocarbon groups containing a ring in the structure thereof".

As the alicyclic hydrocarbon group, groups in which two or more hydrogen atoms have been removed from cyclopentane, cyclohexane, norbornane, isobornane, adamantane, tricyclodecane or tetracyclododecane are particularly desirable.

When R$^{29'}$ represents a divalent linking group containing a hetero atom, preferred examples of the linking group include —O—, —C(=O)—O—, —C(=O)—, —O—C(=O)—O—, —C(=O)—NH—, —NH— (wherein H may be substituted with a substituent such as an alkyl group or acyl group), —S—, —S(=O)$_2$—, —S(=O)$_2$—O—, or a group represented by one of the general formulas -A-O—B—, -[A-C(=O)—O]$_{m'}$—B— or -A-O—C(=O)—B— [wherein each of A and B independently represents a divalent hydrocarbon group which may have a substituent, O represents an oxygen atom, and m' represents an integer of 0 to 3].

When R$^{29'}$ represents —NH—, the H may be substituted with a substituent such as an alkyl group or an aryl group (aromatic group) or the like. The substituent (the alkyl group or aryl group or the like) preferably contains 1 to 10 carbon atoms, more preferably 1 to 8 carbon atoms, and most preferably 1 to 5 carbon atoms.

In the groups represented by general formulas -A-O—B—, -[A-C(=O)—O]$_{m'}$—B— or -A-O—C(=O)—B—, each of A and B independently represents a divalent hydrocarbon group which may have a substituent. Examples of these divalent hydrocarbon groups include the same groups as those described above for the "divalent hydrocarbon group which may have a substituent" for A within the aforementioned group Y$^2$.

A is preferably a linear aliphatic hydrocarbon group, more preferably a linear alkylene group, still more preferably a linear alkylene group of 1 to 5 carbon atoms, and most preferably a methylene group or ethylene group.

B is preferably a linear or branched aliphatic hydrocarbon group, and is more preferably a methylene group, ethylene group or alkylmethylene group. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula -[A-C(=O)—O]$_{m'}$—B—, m' represents an integer of 0 to 3, preferably an integer of 0 to 2, more preferably 0 or 1, and most preferably 1. In other words, the group represented by -[A-C(=O)—O]$_{m'}$—B— is most preferably a group represented by the formula -A-C(=O)—O—B—. Among such groups, groups represented by —(CH$_2$)$_{a'}$—C(=O)—O—(CH$_2$)$_{b'}$— are particularly preferred. In this formula, a' represents an integer of 1 to 10, preferably an integer of 1 to 8, more preferably an integer of 1 to 5, still more preferably 1 or 2, and most preferably 1. b' represents an integer of 1 to 10, preferably an integer of 1 to 8, more preferably an integer of 1 to 5, still more preferably 1 or 2, and most preferably 1.

Of the above, the divalent linking group containing a hetero atom is preferably an alkylene group or a linear group containing an oxygen atom as the hetero atom, such as a group containing an ether linkage or an ester linkage.

The alkylene group is preferably a linear or branched alkylene group. Specific examples include the same groups as the linear alkylene groups and branched alkylene groups described above for the aliphatic hydrocarbon group for A within the group Y$^2$.

As the divalent linking group containing an ester linkage, groups represented by general formula: —R$^2$—C(=O)—O— (wherein R$^2$ represents a divalent linking group) are preferred. In other words, the structural unit (a0) is preferably a structural unit represented by general formula (a0-0-1) shown below.

[Chemical Formula 37]

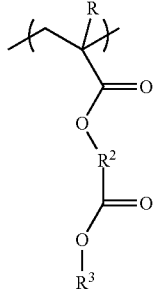

(a0-0-1)

In the formula, R represents a hydrogen atom, an alkyl group of 1 to 5 carbon atoms or a halogenated alkyl group of 1 to 5 carbon atoms, R$^2$ represents a divalent linking group, and R$^3$ represents an —SO$_2$-containing cyclic group.

There are no particular limitations on R$^2$, and examples include the same divalent linking groups as those described above for R$^{29'}$ in general formula (a0-0).

As the divalent linking group for R$^2$, a linear or branched alkylene group, a divalent alicyclic hydrocarbon group, or a divalent linking group containing a hetero atom is preferred.

Examples of the linear or branched alkylene group, divalent alicyclic hydrocarbon group, and divalent linking group containing a hetero atom include the same linear or branched alkylene groups, divalent alicyclic hydrocarbon groups, and divalent linking groups containing a hetero atom as those described above as preferred groups for R$^{29'}$.

Of the above groups, a linear or branched alkylene group, or a divalent linking group containing an oxygen atom as a hetero atom is preferred.

As the linear alkylene group, a methylene group or ethylene group is preferred, and a methylene group is particularly desirable.

As the branched alkylene group, an alkylmethylene group or alkylethylene group is preferred, and —CH(CH$_3$)—, —C(CH$_3$)$_2$— and —C(CH$_3$)$_2$CH$_2$— are particularly desirable.

The divalent linking group containing an oxygen atom is preferably a divalent linking group containing an ether linkage or an ester linkage, and is more preferably a group represented by a formula -A-O—B—, -[A-C(=O)—O]$_{m'}$—B— or -A-O—C(=O)—B—. m' represents an integer of 0 to 3.

Among these, groups represented by -A-O—C(=O)—B— are preferred, and groups represented by —(CH$_2$)$_c$—C(=O)—O—(CH$_2$)$_d$— are particularly desirable. c represents an integer of 1 to 5, and is preferably 1 or 2. d represents an integer of 1 to 5, and is preferably 1 or 2.

As the structural unit (a0), structural units represented by general formula (a0-0-11) or (a0-0-12) shown below are preferred, and structural units represented by formula (a0-0-12) are particularly desirable.

[Chemical Formula 38]

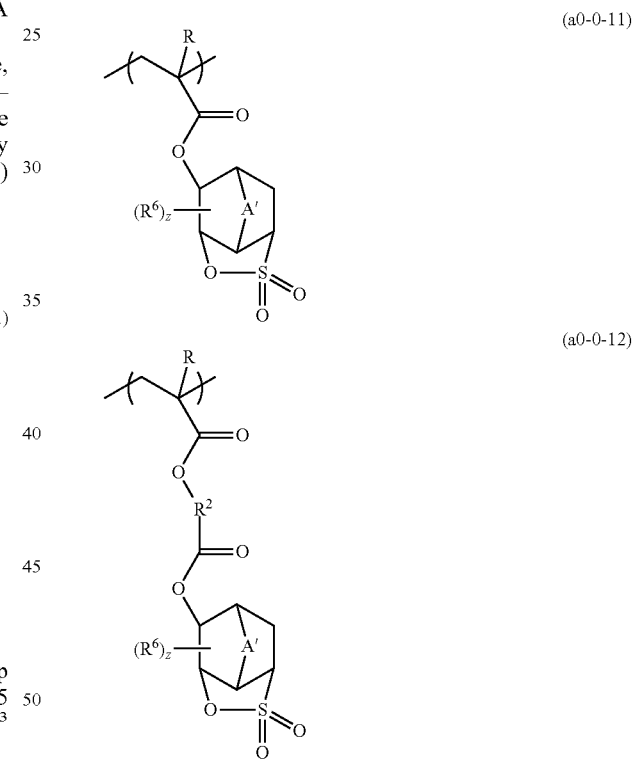

In the formulas, R, A', R$^6$, z and R$^2$ are each the same as defined above.

In formula (a0-0-11), A' is preferably a methylene group, an ethylene group, an oxygen atom (—O—) or a sulfur atom (—S—).

R$^2$ is preferably a linear or branched alkylene group, or a divalent linking group containing an oxygen atom. Examples of the linear or branched alkylene group and the divalent linking group containing an oxygen atom for R$^2$ include the same linear or branched alkylene groups and divalent linking groups containing an oxygen described above.

As the structural unit represented by formula (a0-0-12), structural units represented by general formula (a0-0-12a) and (a0-0-12b) shown below are particularly desirable.

[Chemical Formula 39]

(a0-0-12a)

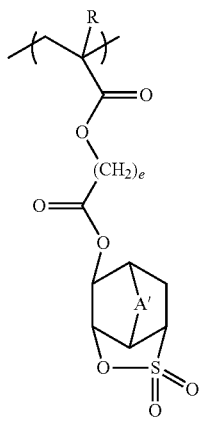

(a0-0-12b)

In the formulas, R and A' are each the same as defined above, and each of c to e independently represents an integer of 1 to 3.

As the structural unit (a0), one type of structural unit may be used alone, or two or more types of structural units may be used in combination.

The amount of the structural unit (a0) within the component (A1), based on the combined total of all the structural units that constitute the component (A1), is preferably within a range from 1 to 60 mol %, more preferably from 5 to 55 mol %, still more preferably from 10 to 50 mol %, and most preferably from 15 to 45 mol %, as such an amount yields a favorable shape for the resist pattern formed using a resist composition containing the component (A1), and also produces excellent lithography properties such as the EL margin, LWR and mask reproducibility.

(Other Structural Units)

The component (A1) may also have a structural unit other than the aforementioned structural units (a1) to (a3) and (a0), as long as the effects of the present invention are not impaired.

As such a structural unit, any other structural unit which cannot be classified as one of the above structural units (a1) to (a3) or (a0) can be used without any particular limitation, and any of the multitude of conventional structural units used within resist resins for ArF excimer lasers or KrF excimer lasers (and particularly for ArF excimer lasers) can be used.

One example of such a structural unit is a structural unit (a4) derived from an acrylate ester containing a non-acid-dissociable aliphatic polycyclic group.

Structural Unit (a4)

The structural unit (a4) is a structural unit which is derived from an acrylate ester that may have an atom other than a hydrogen atom or a substituent bonded to the carbon atom on the α-position, and contains a non-acid-dissociable aliphatic polycyclic group.

In the structural unit (a4), examples of the polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 40]

(a4-1)

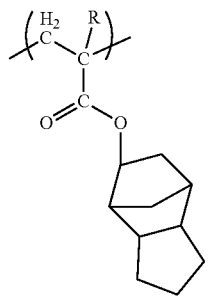

(a4-2)

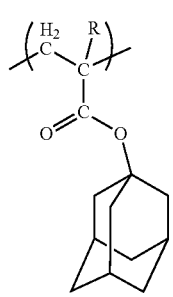

(a4-3)

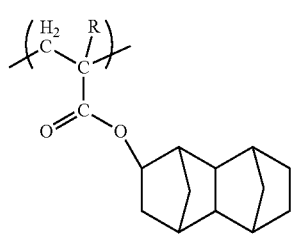

-continued (a4-4)

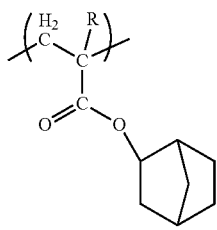

(a4-5)

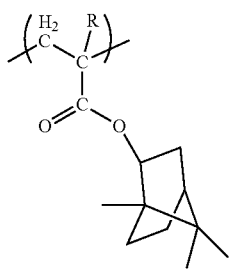

In the formulas, R is the same as defined above.

When the structural unit (a4) is included in the component (A1), the amount of the structural unit (a4), based on the combined total of all the structural units that constitute the component (A1), is preferably within the range from 1 to 30 mol %, and more preferably from 10 to 20 mol %.

In the resist composition of the present invention, the component (A1) is preferably a polymeric compound containing the structural unit (a1). Further, in terms of enhancing the adhesion of the resist film to substrates and improving the lithography properties, the component (A1) is preferably a polymeric compound containing the structural unit (a0).

Examples of the component (A1) include copolymers composed of the structural units (a1), (a2) and (a3), copolymers composed of the structural units (a1), (a2), (a3) and (a4), copolymers composed of the structural units (a1), (a2) and (a0), copolymers composed of the structural units (a1), (a3) and (a0), copolymers composed of the structural units (a1), (a2), (a3) and (a0), and copolymers composed of the structural units (a1), (a2), (a3), (a0) and (a4).

In the component (A), either a single component (A1) may be used alone, or two or more different types of the component (A1) may be used in combination.

In the present invention, as the component (A1), copolymers including the combinations of structural units shown below are particularly preferred.

[Chemical Formula 41]

(A1-11)

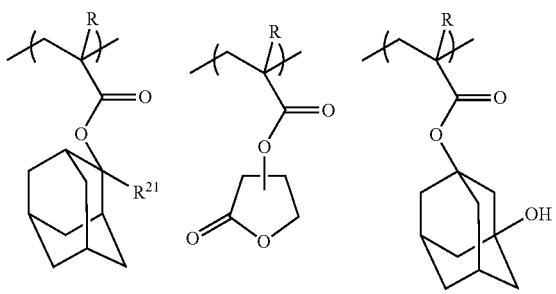

In the above formulas, R and $R^{21}$ are each the same as defined above, and the plurality of R groups may be the same or different from each other.

In formula (A1-11), the lower alkyl group for $R^{21}$ is the same as defined above for the lower alkyl group for R, is preferably a methyl group or an ethyl group, and is most preferably a methyl group.

[Chemical Formula 42]

(A1-12)

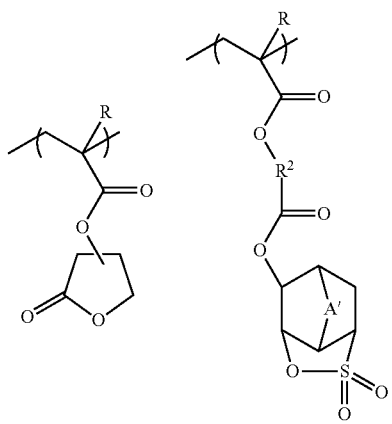

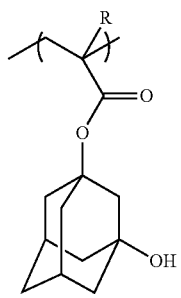

In the above formulas, R, $R^2$, A', $R^{21}$ and $R^{22}$ are each the same as defined above, and the plurality of R groups may be the same or different from each other.

[Chemical Formula 43]

(A1-13)

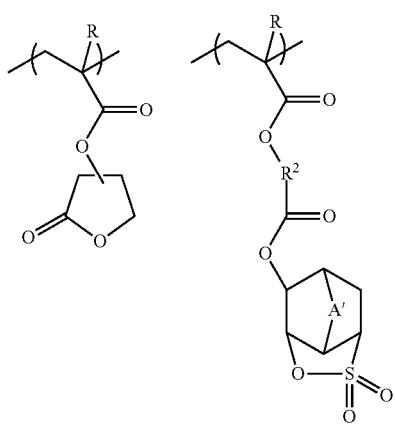

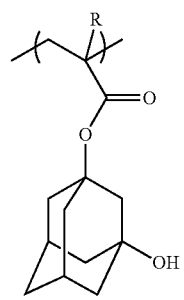

In the above formulas, R, R², A', R²¹ and R²² are each the same as defined above, and the plurality of R groups may be the same or different from each other.

[Chemical Formula 44]

(A1-14)

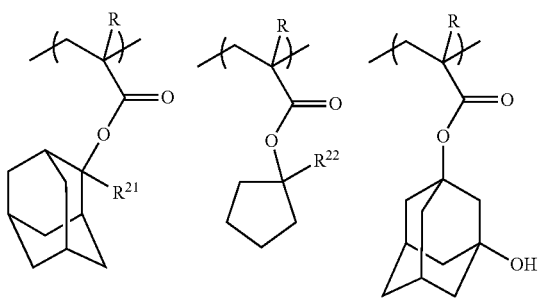

In the above formulas, R, R², A' and R²¹ are each the same as defined above, and the plurality of R groups may be the same or different from each other.

[Chemical Formula 45]

(A1-15)

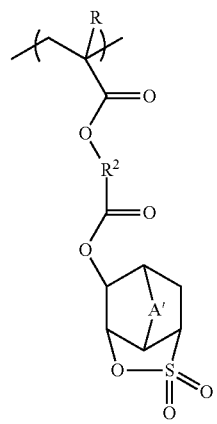

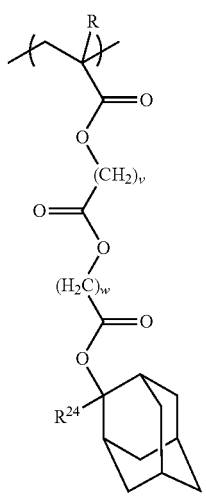

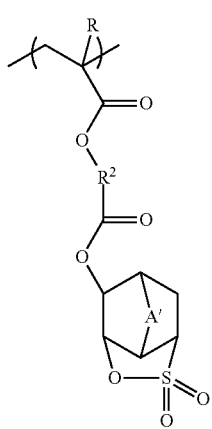

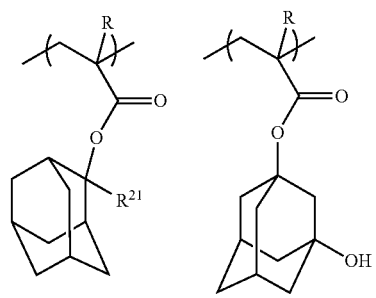

In the above formulas, R, R², A', R²⁴, v, w and R²¹ are each the same as defined above, and the plurality of R groups may be the same or different from each other.

[Chemical Formula 46]

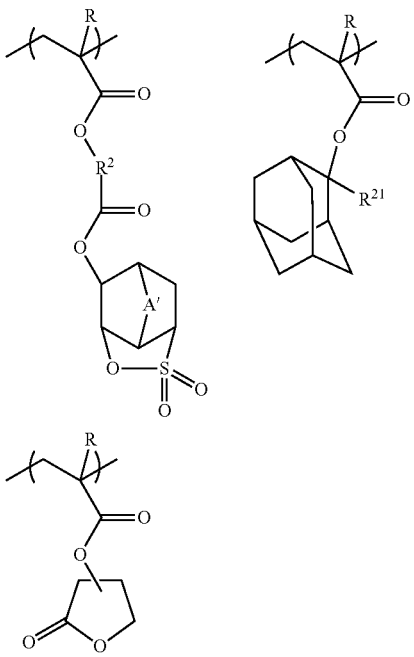

(A1-16)

In the above formulas, R, $R^2$, A' and $R^{21}$ are each the same as defined above, and the plurality of R groups may be the same or different from each other.

[Chemical Formula 47]

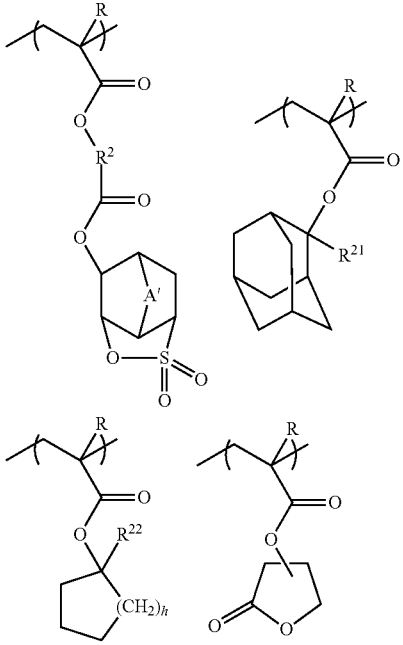

(A1-17)

In the above formulas, R, $R^2$, A', $R^{21}$, $R^{22}$ and h are each the same as defined above, and the plurality of R groups may be the same or different from each other.

[Chemical Formula 48]

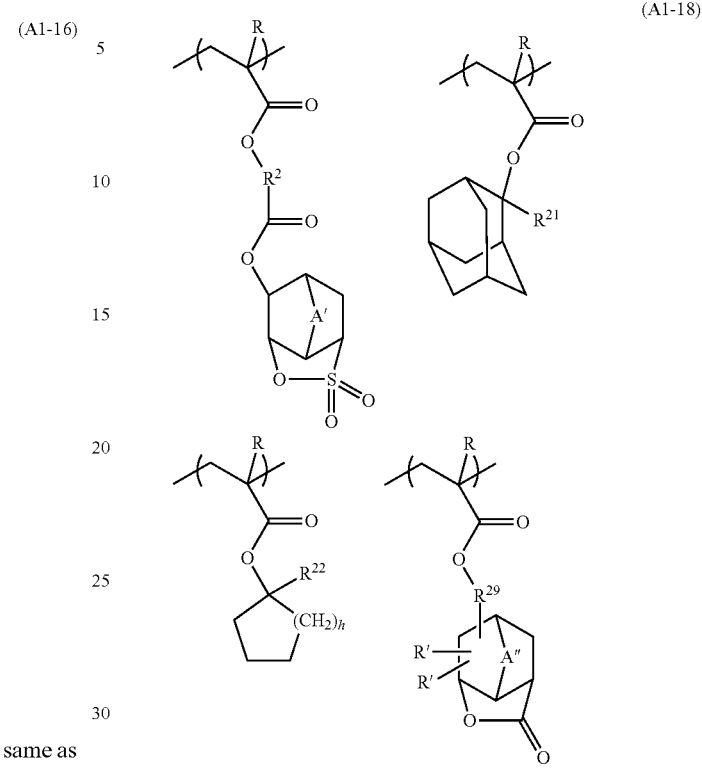

(A1-18)

In the above formulas, R, $R^2$, A', $R^{21}$, $R^{22}$, h, $R^{29}$, A" and R' are each the same as defined above, and the plurality of R groups may be the same or different from each other.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH during the above polymerization, a —$C(CF_3)_2$—OH group can be introduced at the terminals of the component (A1). Such a copolymer having an introduced hydroxyalkyl group in which some of the hydrogen atoms of the alkyl group have been substituted with fluorine atoms is effective in reducing developing defects and LER (line edge roughness: unevenness in the side walls of a line pattern).

The weight-average molecular weight (Mw) (the polystyrene equivalent value determined by gel permeation chromatography) of the component (A1) is not particularly limited, but is preferably within a range from 1,000 to 50,000, more preferably from 1,500 to 30,000, and most preferably from 2,500 to 20,000. By ensuring that the weight-average molecular weight is not more than the upper limit of the aforementioned range, the polymeric compound (A1) exhibits satisfactory solubility in a resist solvent when used as a resist, whereas by ensuring that the weight average molecular weight is at least as large as the lower limit of the aforementioned range, dry etching resistance and the cross-sectional shape of the resist pattern are improved.

Further, the dispersity (Mw/Mn) of the component (A1) is preferably from 1.0 to 5.0, more preferably from 1.0 to 3.0, and most preferably from 1.0 to 2.5. Here, Mn is the number-average molecular weight.

The resist composition of the present invention may include, as the component (A), a base component that does not correspond with the definition for the component (A1), but which exhibits increased solubility in an alkali developing solution under the action of acid.

There are no particular limitations on this base component that does not correspond with the aforementioned component (A1), and the base component may be selected arbitrarily from the multitude of conventional base components used for chemically amplified resist compositions, including resins such as novolac resins and polyhydroxystyrene (PHS)-based resins, as well as low molecular weight components (the component (A2)).

Examples of the component (A2) include low molecular weight compounds having a molecular weight of at least 500 but less than 4,000 that include both a hydrophilic group and an acid-dissociable, dissolution-inhibiting group such as those described above in connection with the component (A1). Specific examples of these low molecular weight compounds include compounds having a plurality of phenol structures in which some of the hydrogen atoms of the hydroxyl groups have been substituted with the aforementioned acid-dissociable, dissolution-inhibiting groups.

In the resist composition of the present invention, either a single component (A) may be used alone, or two or more different types of the component (A) may be used in combination.

The amount of the component (A1) within the component (A), based on the total weight of the component (A), is preferably not less than 25% by weight, more preferably 50% by weight or more, and still more preferably 75% by weight or more. The amount of the component (A1) may also represent 100% by weight of the component (A). Provided the amount is not less than 25% by weight, a resist pattern having superior resolution and a high degree of rectangularity can be more readily formed.

In the resist composition of the present invention, the amount of the component (A) can be adjusted appropriately depending on factors such as the thickness of the resist film to be formed.

<Component (B)>

In the resist composition of the present invention, the component (B) includes an acid generator (B1) (hereinafter referred to as "component (B1)") formed from a compound represented by general formula (b1-1) shown below.

[Chemical Formula 49]

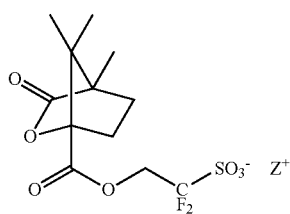

(b1-1)

In the formula, $Z^+$ represents an organic cation.

Cation Moiety of Component (B1)

In the above formula (b1-1), there are no particular limitations on the organic cation for $Z^+$, and any of the cation moieties of conventional onium salt acid generators may be used.

Among such cation moieties, sulfonium ions and iodonium ions are preferred, and sulfonium ions are particularly desirable.

Examples of preferred organic cations for $Z^+$ include organic cations represented by general formula (b1-c1) and general formula (b1-c2) shown below.

[Chemical Formula 50]

In the above formulas, each of $R^{1''}$ to $R^{3''}$ and $R^{5''}$ to $R^{6''}$ independently represents an aryl group which may have a substituent, an alkyl group or an alkenyl group. Two of $R^{1''}$ to $R^{3''}$ in formula (b1-c1) may be bonded to each other to form a ring together with the sulfur atom in the formula.

In formula (b1-c1), each of $R^{1''}$ to $R^{3''}$ independently represents an aryl group which may have a substituent, an alkyl group or an alkenyl group. Two of $R^{1''}$ to $R^{3''}$ may be bonded to each other to form a ring together with the sulfur atom in the formula.

Further, in terms of achieving better improvement in the lithography properties and the resist pattern shape, it is preferable that at least one of $R^{1''}$ to $R^{3''}$ is an aryl group, more preferable that two or more of $R^{1''}$ to $R^{3''}$ are aryl groups, and most preferable that all of $R^{1''}$ to $R^{3''}$ are aryl groups.

Examples of the aryl group for $R^{1''}$ to $R^{3''}$ include unsubstituted aryl groups of 6 to 20 carbon atoms, and substituted aryl groups in which some or all of the hydrogen atoms of an aforementioned unsubstituted aryl group have each been substituted with an alkyl group, alkoxy group, alkoxyalkyloxy group, alkoxycarbonylalkyloxy group, halogen atom, hydroxyl group, oxo group (=O), aryl group, —C—(=O)—O—$R^{6't}$, —O—C(=O)—$R^{7't}$ or —O—$R^{8t}$.

Each of $R^{6't}$, $R^{7't}$ and $R^{8t}$ represents a linear or branched saturated hydrocarbon group of 1 to 25 carbon atoms, a cyclic saturated hydrocarbon group of 3 to 20 carbon atoms, or a linear or branched aliphatic unsaturated hydrocarbon group of 2 to 5 carbon atoms.

The linear or branched saturated hydrocarbon group contains 1 to 25 carbon atoms, preferably 1 to 15 carbon atoms, and more preferably 4 to 10 carbon atoms.

Examples of the linear saturated hydrocarbon group include a methyl group, ethyl group, propyl group, butyl group, pentyl group, hexyl group, heptyl group, octyl group, nonyl group and decyl group.

Examples of the branched saturated hydrocarbon group, excluding tertiary alkyl groups, include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The linear or branched saturated hydrocarbon group may have a substituent. Examples of the substituent include an alkoxy group, halogen atom, halogenated alkyl group, hydroxyl group, oxygen atom (=O), cyano group or carboxyl group.

The alkoxy group as the substituent for the linear or branched saturated hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the linear or branched saturated hydrocarbon group include a fluorine atom, chlorine atom, bromine atom or iodine atom, and a fluorine atom is preferable.

Examples of the halogenated alkyl group as a substituent for the linear or branched saturated hydrocarbon group include groups in which some or all of the hydrogen atoms within an aforementioned linear or branched saturated hydrocarbon group have each been substituted with an aforementioned halogen atom.

The cyclic saturated hydrocarbon group of 3 to 20 carbon atoms for $R^{6\prime}$, $R^{7\prime}$ and $R^{8\prime}$ may be either a polycyclic group or a monocyclic group. Examples include groups in which one hydrogen atom has been removed from a monocycloalkane, and groups in which one hydrogen atom has been removed from a polycycloalkane such as a bicycloalkane, tricycloalkane or tetracycloalkane. More specific examples include groups in which one hydrogen atom has been removed from a monocycloalkane such as cyclopentane, cyclohexane, cycloheptane or cyclooctane, and groups in which one hydrogen atom has been removed from a polycycloalkane such as adamantane, norbornane, isobornane, tricyclodecane or tetracyclododecane.

The cyclic saturated hydrocarbon group may have a substituent. For example, some of the carbon atoms that constitute the ring within the cyclic saturated hydrocarbon group may be substituted with a hetero atom, or a hydrogen atom bonded to the ring within the cyclic saturated hydrocarbon may be substituted with a substituent.

Examples of the former case include groups in which one or more hydrogen atoms have been removed from a heterocycloalkane in which some of the carbon atoms that constitute the ring(s) of an aforementioned monocycloalkane or a polycycloalkane have been substituted with a hetero atom such as an oxygen atom, sulfur atom or nitrogen atom. Further, the ring structure may include an ester linkage (—C(=O)—O—). Specific examples include lactone-containing monocyclic groups such as groups in which one hydrogen atom has been removed from γ-butyrolactone, and lactone-containing polycyclic groups in which one hydrogen atom has been removed from a lactone ring-containing bicycloalkane, tricycloalkane or tetracycloalkane.

In the latter case, examples of the substituent include the same substituents as those described above for the linear or branched saturated hydrocarbon group, or a lower alkyl group.

Further, $R^{6\prime}$, $R^{7\prime}$ and $R^{8\prime}$ may be a combination of a linear or branched alkyl group and a cyclic alkyl group.

Examples of combinations of a linear or branched alkyl group and a cyclic alkyl group include groups in which a cyclic alkyl group is bonded as a substituent to a linear or branched alkyl group, and groups in which a linear or branched alkyl group is bonded as a substituent to a cyclic alkyl group.

Examples of the linear aliphatic unsaturated hydrocarbon group for $R^{6\prime}$, $R^{7\prime}$ and $R^{8\prime}$ include a vinyl group, propenyl group (allyl group), and butynyl group.

Examples of the branched aliphatic unsaturated hydrocarbon group for $R^{6\prime}$, $R^{7\prime}$ and $R^{8\prime}$ include a 1-methylpropenyl group and 2-methylpropenyl group.

The linear or branched aliphatic unsaturated hydrocarbon group may have a substituent. Examples of the substituent include the same substituents as those described above for the linear or branched saturated hydrocarbon group.

Of the various possibilities described above, each of $R^{7\prime}$ and $R^{8\prime}$ is preferably a linear or branched saturated hydrocarbon group of 1 to 15 carbon atoms, or a cyclic saturated hydrocarbon group of 3 to 20 carbon atoms, as such groups yield superior lithography properties and resist pattern shape.

The unsubstituted aryl group for $R^{1\prime\prime}$ to $R^{3\prime\prime}$ is preferably an aryl group of 6 to 10 carbon atoms because such groups enable lower cost synthesis. Specific examples include a phenyl group and a naphthyl group.

The alkyl group as the substituent for the substituted aryl group for $R^{1\prime\prime}$ to $R^{3\prime\prime}$ is preferably an alkyl group having 1 to 5 carbon atoms, and most preferably a methyl group, ethyl group, propyl group, n-butyl group, or tert-butyl group.

The alkoxy group as the substituent for the substituted aryl group is preferably an alkoxy group having 1 to 5 carbon atoms, and most preferably a methoxy group, ethoxy group, n-propoxy group, iso-propoxy group, n-butoxy group or tert-butoxy group.

The halogen atom as the substituent for the substituted aryl group is preferably a fluorine atom.

Examples of the aryl group as the substituent for the substituted aryl group include the same aryl groups as those described above for $R^{1\prime\prime}$ to $R^{3\prime\prime}$, and of these, aryl groups of 6 to 20 carbon atoms are preferred, aryl groups of 6 to 10 carbon atoms are more preferred, and a phenyl group or naphthyl group is particularly desirable.

Examples of the alkoxyalkyloxy group as the substituent for the substituted aryl group include groups represented by the general formula shown below.

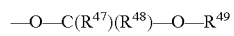

$$-O-C(R^{47})(R^{48})-O-R^{49}$$

In this formula, each of $R^{47}$ and $R^{48}$ independently represents a hydrogen atom or a linear or branched alkyl group, and $R^{49}$ represents an alkyl group.

The alkyl group for $R^{47}$ and $R^{48}$ preferably has 1 to 5 carbon atoms and may be either linear or branched, is preferably an ethyl group or a methyl group, and is most preferably a methyl group.

It is preferable that at least one of $R^{47}$ and $R^{48}$ is a hydrogen atom, and it is particularly desirable that either one of $R^{47}$ and $R^{48}$ is a hydrogen atom and the other is a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms, and examples thereof include a methyl group, ethyl group, propyl group, n-butyl group or tert-butyl group.

The cyclic alkyl group for $R^{49}$ preferably has 4 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane, which may or may not be substituted with an alkyl group of 1 to 5 carbon atoms, a fluorine atom or a fluorinated alkyl group. Examples of the monocycloalkane include cyclopentane and cyclohexane. Examples of the polycycloalkane include adamantane, norbornane, isobornane, tricyclodecane and tetracyclododecane. Among these, groups in which one or more hydrogen atoms have been removed from adamantane are preferable.

Examples of the alkoxycarbonylalkyloxy group as the substituent for the substituted aryl group include groups represented by the general formula shown below.

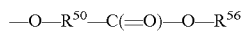
—O—R$^{50}$—C(=O)—O—R$^{56}$

In this formula, R$^{50}$ represents a linear or branched alkylene group, and R$^{56}$ represents a tertiary alkyl group.

The linear or branched alkylene group for R$^{50}$ preferably has 1 to 5 carbon atoms, and examples thereof include a methylene group, ethylene group, trimethylene group, tetramethylene group and 1,1-dimethylethylene group.

Examples of the tertiary alkyl group for R$^{56}$ include a 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group and tert-hexyl group.

Moreover, groups in which R$^{56}$ in the general formula —O—R$^{50}$—C(=O)—O—R$^{56}$ has been substituted with R$^{56'}$ may also be used. R$^{56'}$ represents a hydrogen atom, an alkyl group, a fluorinated alkyl group, or an aliphatic cyclic group which may contain a hetero atom.

Examples of the alkyl group for R$^{56'}$ include the same groups as those described above for the alkyl group for R$^{49}$.

Examples of the fluorinated alkyl group for R$^{56'}$ include groups in which some or all of the hydrogen atoms within an aforementioned alkyl group for R$^{49}$ have been substituted with fluorine atoms.

Examples of the aliphatic cyclic group which may contain a hetero atom for R$^{56'}$ include aliphatic cyclic groups that do not contain a hetero atom, aliphatic cyclic groups containing a hetero atom within the ring structure, and groups in which one or more hydrogen atoms within an aliphatic cyclic group have been substituted with a hetero atom.

For R$^{56'}$, examples of the aliphatic cyclic groups that do not contain a hetero atom include groups in which one or more hydrogen atoms have been removed from a monocycloalkane or a polycycloalkane such as a bicycloalkane, tricycloalkane or tetracycloalkane. Examples of the monocycloalkane include cyclopentane and cyclohexane. Examples of the polycycloalkane include adamantane, norbornane, isobornane, tricyclodecane and tetracyclododecane. Among these, groups in which one or more hydrogen atoms have been removed from adamantane are preferable.

For R$^{56'}$, specific examples of the aliphatic cyclic groups containing a hetero atom within the ring structure include groups represented by formulas (L1) to (L5) and (S1) to (S4) shown below.

For R$^{56'}$, specific examples of the groups in which one or more hydrogen atoms within the aliphatic cyclic group have been substituted with a hetero atom include groups in which two hydrogen atoms within an aliphatic cyclic group have been substituted with an oxygen atom (=O).

The aryl group for each of R$^{1\prime\prime\prime}$ to R$^{3\prime\prime\prime}$ is preferably a phenyl group or a naphthyl group.

Examples of the alkyl group for R$^{1\prime\prime\prime}$ to R$^{3\prime\prime\prime}$ include linear, branched and cyclic alkyl groups having 1 to 10 carbon atoms. In terms of achieving excellent resolution, the alkyl group preferably has 1 to 5 carbon atoms. Specific examples include a methyl group, ethyl group, n-propyl group, isopropyl group, n-butyl group, isobutyl group, n-pentyl group, cyclopentyl group, hexyl group, cyclohexyl group, nonyl group and decyl group. A methyl group is most preferable because it yields excellent resolution and enables synthesis to be conducted at a low cost.

The alkenyl group for R$^{1\prime\prime\prime}$ to R$^{3\prime\prime\prime}$ preferably has 2 to 10 carbon atoms, more preferably 2 to 5 carbon atoms, and still more preferably 2 to 4 carbon atoms. Specific examples of the alkenyl group include a vinyl group, propenyl group (allyl group), butenyl group, 1-methylpropenyl group and 2-methylpropenyl group.

In those cases where two of R$^{1\prime\prime\prime}$ to R$^{3\prime\prime\prime}$ are bonded to each other to form a ring together with the sulfur atom in the formula, the ring including the sulfur atom is preferably a 3- to 10-membered ring, and more preferably a 5- to 7-membered ring.

When two of R$^{1\prime\prime\prime}$ to R$^{3\prime\prime\prime}$ are bonded to each other to form a ring together with the sulfur atom in the formula, the remaining one of R$^{1\prime\prime\prime}$ to R$^{3\prime\prime\prime}$ is preferably an aryl group. Examples of this aryl group include the same groups as those described above for the aryl group for R$^{1\prime\prime\prime}$ to R$^{3\prime\prime\prime}$.

Specific examples of the cation moiety represented by formula (b1-c1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl) diphenylsulfonium, (4-(2-methyl-2-adamantyloxycarbonylmethyloxy)phenyl) diphenylsulfonium, (4-(2-methyl-2-adamantyloxycarbonylmethyloxy)-3,5-dimethylphenyl) diphenylsulfonium, tri(4-methylphenyl)sulfonium, dimethyl (4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl) phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl) tetrahydrothiopyranium and 1-(4-methylphenyl)tetrahydrothiopyranium.

Furthermore, examples of preferred organic cations represented by the above formula (b1-c1) include the cations shown below.

[Chemical Formula 51]

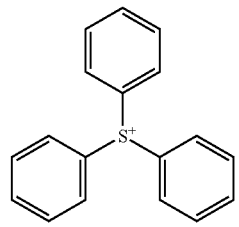

(b1-c1-1)

(b1-c1-2)
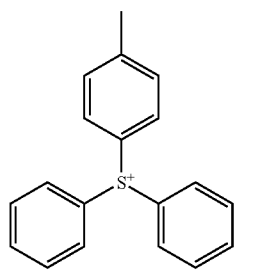
(b1-c1-3)
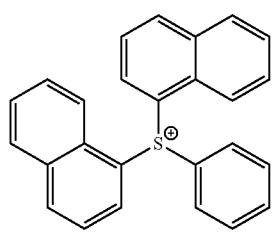
[Chemical Formula 52]
(b1-c1-4)
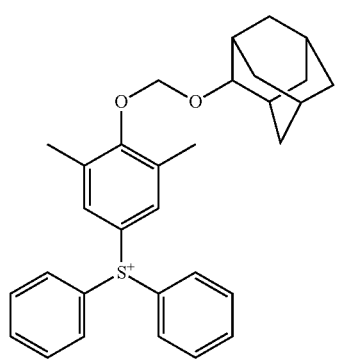
(b1-c1-5)
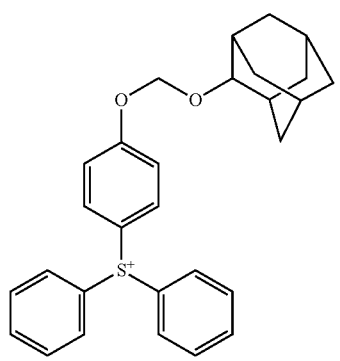
(b1-c1-6)
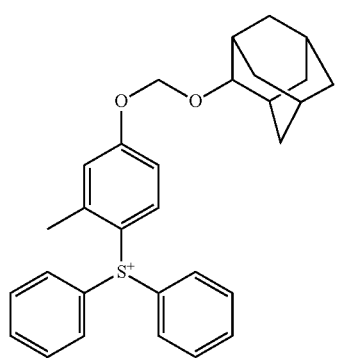
[Chemical Formula 53]
(b1-c1-7)
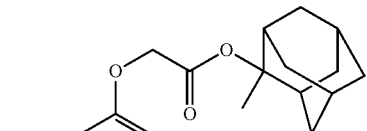
(b1-c1-8)
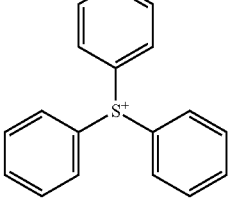
(b1-c1-9)
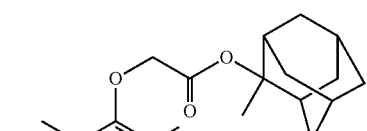
(b1-c1-10)
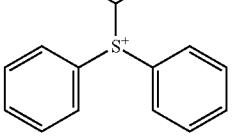
(b1-c1-11)
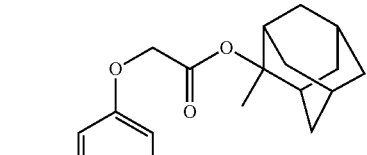

(b1-c1-12)
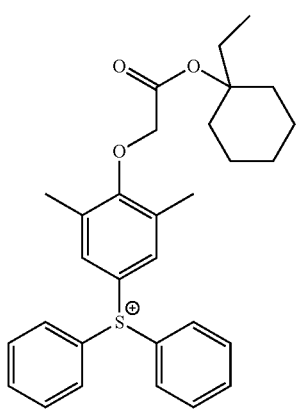
(b1-c1-13)
[Chemical Formula 54]
(b1-c1-14)
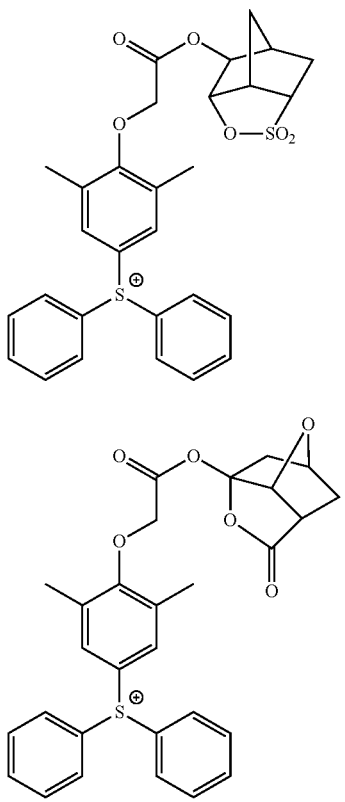
(b1-c1-15)
(b1-c1-16)
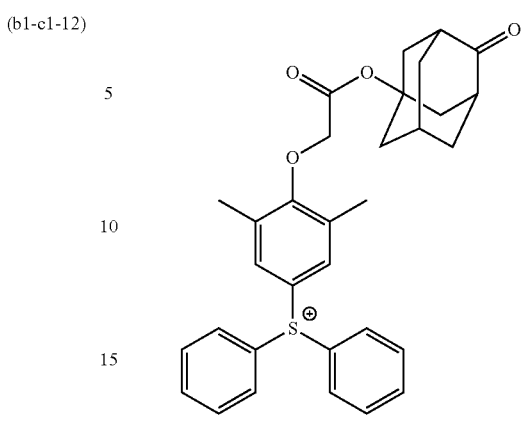
(b1-c1-17)
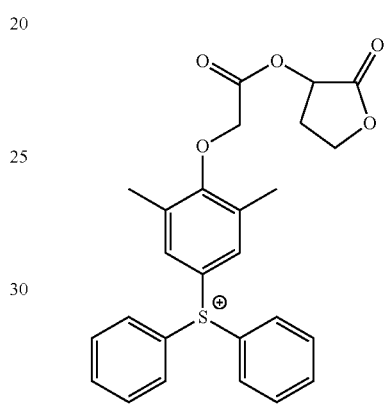
(b1-c1-18)
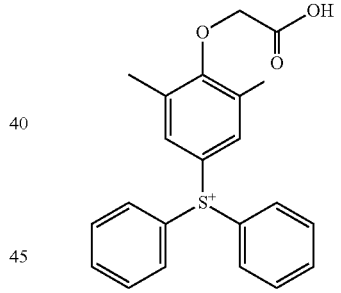
(b1-c1-19)
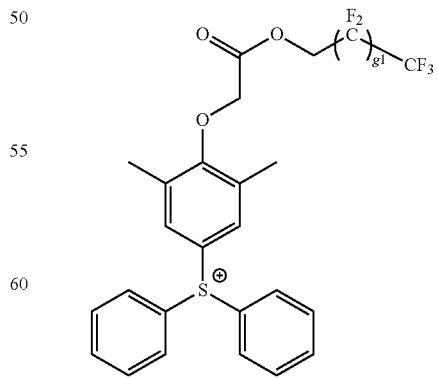
In the above formula, g1 represents the number of repeating units, and is typically an integer of 1 to 5.

[Chemical Formula 55]
(b1-c1-20)
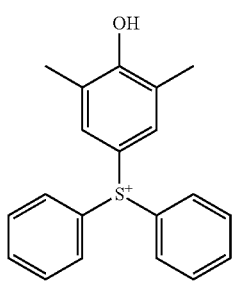
(b1-c1-21)
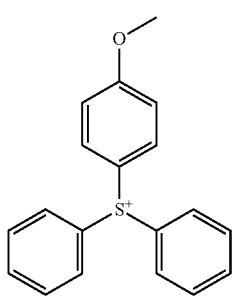
(b1-c1-22)
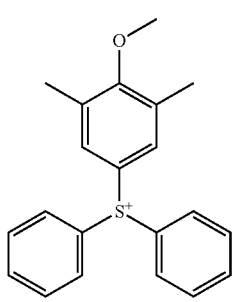
[Chemical Formula 56]
(b1-c1-23)
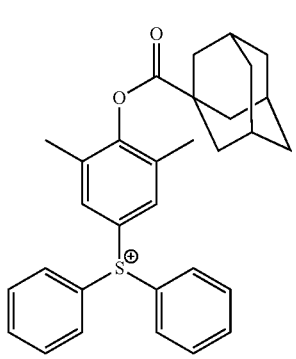
(b1-c1-24)
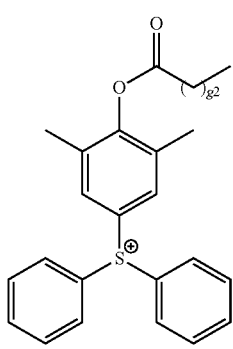
(b1-c1-25)
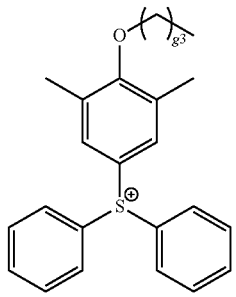
In the above formulas, g2 and g3 represent numbers of repeating units, wherein g2 is an integer of 0 to 20, and g3 is an integer of 0 to 20.
[Chemical Formula 57]
(b1-c1-26)
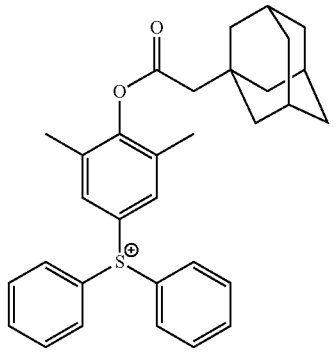
(b1-c1-27)
(b1-c1-28)
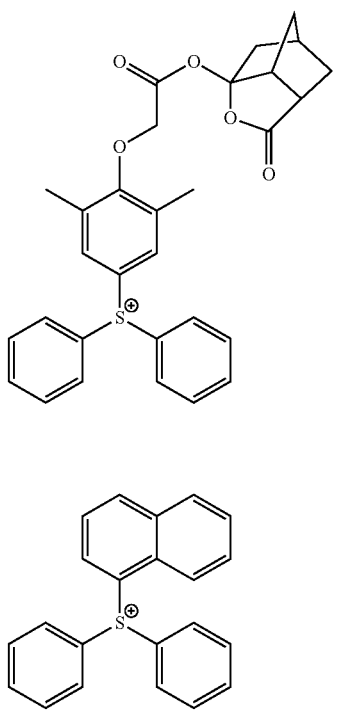

[Chemical Formula 58]

(b1-c1-29)
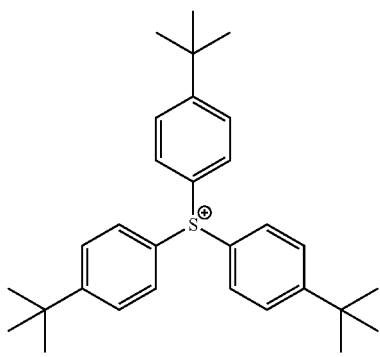

(b1-c1-30)
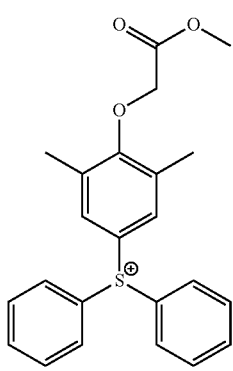

(b1-c1-31)
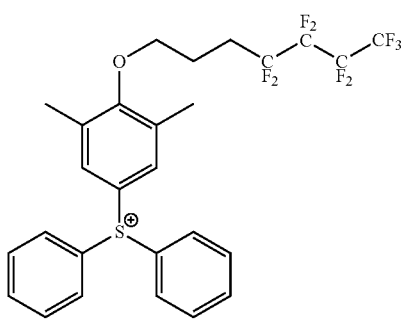

[Chemical Formula 59]

(b1-c1-32)
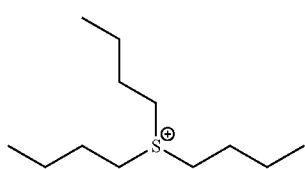

(b1-c1-33)
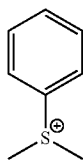

In formula (b1-c2), each of $R^{5\prime\prime\prime}$ and $R^{6\prime\prime\prime}$ independently represents an aryl group which may have a substituent, an alkyl group or an alkenyl group.

Further, in terms of achieving better improvement in the lithography properties and the resist pattern shape, it is preferable that at least one of $R^{5\prime\prime\prime}$ and $R^{6\prime\prime\prime}$ is an aryl group, and more preferable that both of $R^{5\prime\prime\prime}$ and $R^{6\prime\prime\prime}$ are aryl groups.

Examples of the aryl group for $R^{5\prime\prime\prime}$ and $R^{6\prime\prime\prime}$ include the same aryl groups as those described for $R^{\prime\prime}$ to $R^{3\prime\prime}$.

Examples of the alkyl group for $R^{5\prime\prime\prime}$ and $R^{6\prime\prime\prime}$ include the same alkyl groups as those described for $R^{1\prime\prime}$ to $R^{3\prime\prime}$.

Examples of the alkenyl group for $R^{5\prime\prime\prime}$ and $R^{6\prime\prime\prime}$ include the same alkenyl groups as those described for $R^{1\prime\prime}$ to $R^{3\prime\prime}$.

Among the various possibilities, the case in which $R^{5\prime\prime\prime}$ and $R^{6\prime\prime\prime}$ are both phenyl groups is the most desirable.

Specific examples of the cation moieties represented by formula (b1-c2) include diphenyliodonium and bis(4-tert-butylphenyl)iodonium.

Further, examples of other preferred organic cations for $Z^+$ include cations represented by general formula (I-1) and general formula (I-2) shown below.

[Chemical Formula 60]

(I-1)
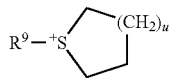

(I-2)
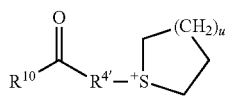

In formulas (I-1) and (I-2), each of $R^9$ and $R^{19}$ independently represents a phenyl group which may have a substituent, a naphthyl group, an alkyl group of 1 to 5 carbon atoms, an alkoxy group, or a hydroxyl group. Examples of the substituent include the same substituents as those described above for the substituted aryl group in connection with the aryl group for $R^{1\prime\prime}$ to $R^{3\prime\prime}$ (namely, an alkyl group, alkoxy group, alkoxyalkyloxy group, alkoxycarbonylalkyloxy group, halogen atom, hydroxyl group, oxo group (=O), aryl group, —C—(=O)—O—$R^{6\prime}$, —O—C(=O)—$R^{7\prime}$, —O—$R^{8\prime}$, —O—$R^{50}$—C(=O)—O—$R^{56}$, and groups in which $R^{56}$ in the general formula —O—$R^{50}$—C(=O)—O—$R^{56}$ has been substituted with $R^{56\prime}$).

$R^{4\prime}$ represents an alkylene group of 1 to 5 carbon atoms.

u represents an integer of 1 to 3, and is most preferably 1 or 2.

Preferred examples of the organic cations represented by the above formulas (I-1) and (I-2) include the cations shown below.

[Chemical Formula 61]

(I-1-1)
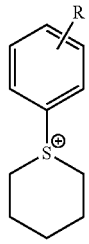

-continued (I-1-2)

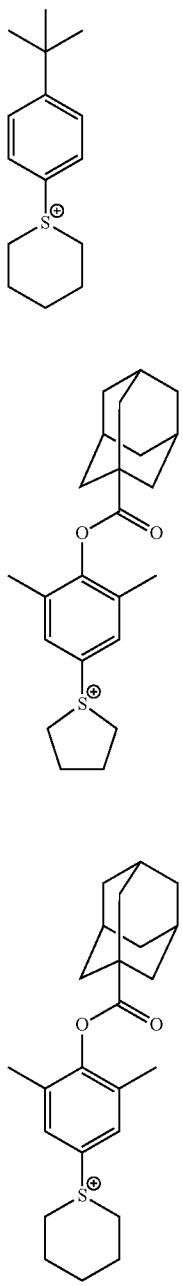

(I-1-3)

(I-1-4)

(I-1-5)

-continued

[Chemical Formula 62]

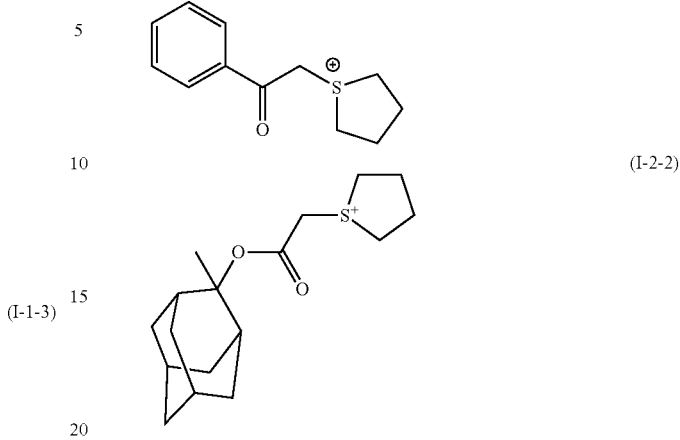

(I-2-1)

(I-2-2)

Furthermore, examples of other preferred organic cations for $Z^+$ include cations represented by general formula (I-5) and general formula (I-6) shown below.

[Chemical Formula 63]

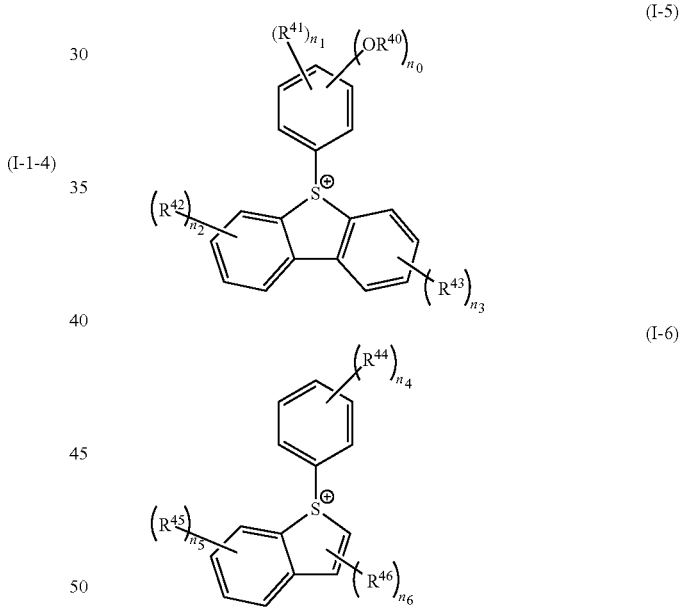

(I-5)

(I-6)

In the formulas, $R^{40}$ represents a hydrogen atom or an alkyl group, $R^{41}$ represents an alkyl group, acetyl group, carboxyl group or hydroxyalkyl group, each of $R^{42}$ to $R^{46}$ independently represents an alkyl group, acetyl group, alkoxy group, carboxyl group or hydroxyalkyl group, each of $n_0$ to $n_5$ independently represents an integer of 0 to 3, provided that $n_0+n_1$ is not more than 5, and $n_6$ represents an integer of 0 to 2.

In general formula (I-5), the alkyl group for $R^{40}$ is preferably an alkyl group of 1 to 15 carbon atoms, more preferably an alkyl group of 1 to 10 carbon atoms, and still more preferably an alkyl group of 4 to 10 carbon atoms. Among these alkyl groups, a linear or branched alkyl group is particularly desirable.

The alkyl group for $R^{41}$ to $R^{46}$ in general formula (I-5) or (I-6) is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably an aforementioned alkyl group in which one or more hydrogen atoms have been substituted with hydroxyl groups. Specific examples include a hydroxymethyl group, hydroxyethyl group and hydroxypropyl group.

If there are two or more $OR^{40}$ groups, as indicated by a value of 2 or greater for $n_0$, then the two or more $OR^{40}$ groups may be the same or different from each other.

If there are two or more of an individual $R^{41}$ to $R^{46}$ group, as indicated by a value of 2 or greater for the corresponding $n_1$ to $n_6$, then the two or more of the individual $R^{41}$ to $R^{46}$ group may be the same or different from each other.

$n_0$ is preferably 0 or 1.
$n^1$ is preferably 0 to 2.
It is preferable that $n_2$ and $n_3$ each represents 0 or 1, and more preferably 0.
$n_4$ is preferably 0 to 2, and more preferably 0 or 1.
$n_5$ is preferably 0 or 1, and more preferably 0.
$n_6$ is preferably 0 or 1.

Examples of preferred organic cations represented by the above formulas (I-5) and (I-6) include the cations shown below.

[Chemical Formula 64]

(I-5-1)

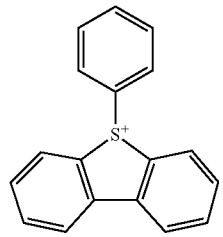

(I-5-2)

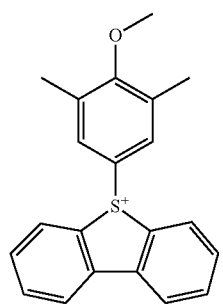

(I-5-3)

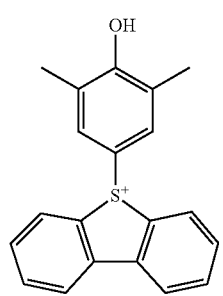

(I-5-4)

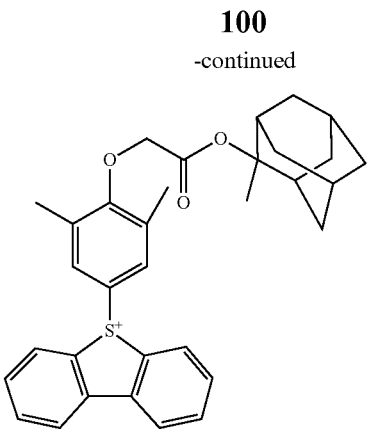

(I-5-5)

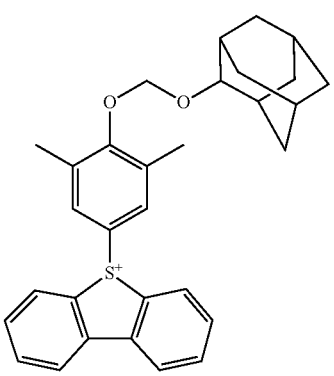

(I-5-6)

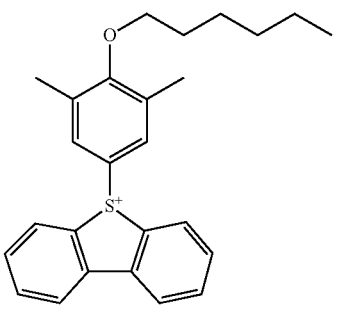

(I-6-1)

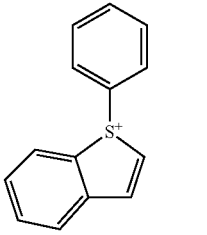

(I-6-2)

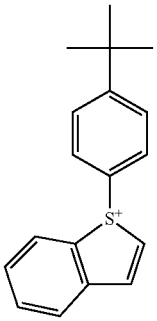

Furthermore, other preferred examples of the organic cation for $Z^+$ include the cations shown below.

[Chemical Formula 65]
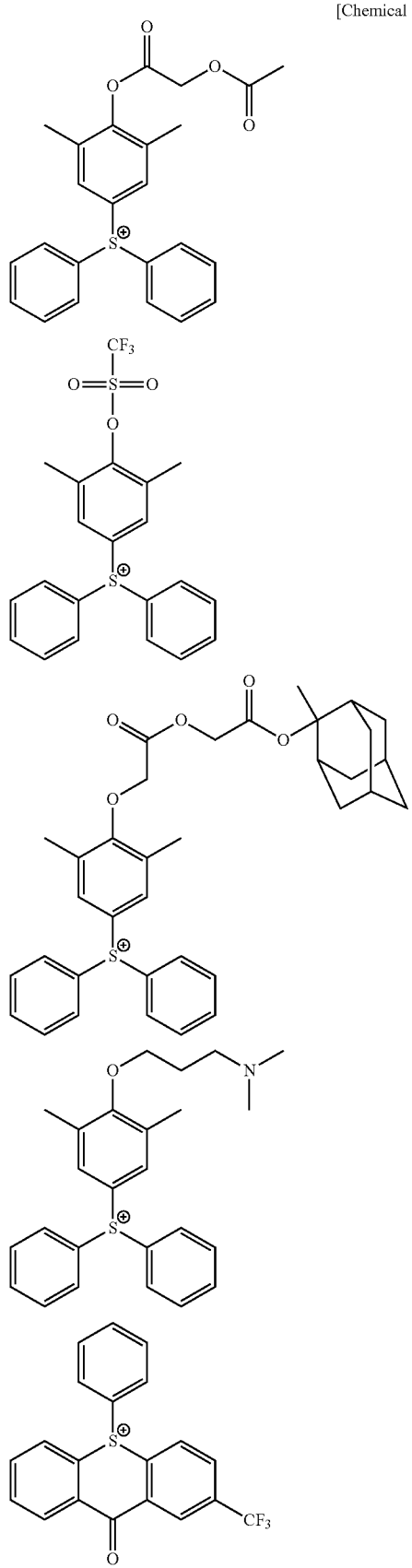
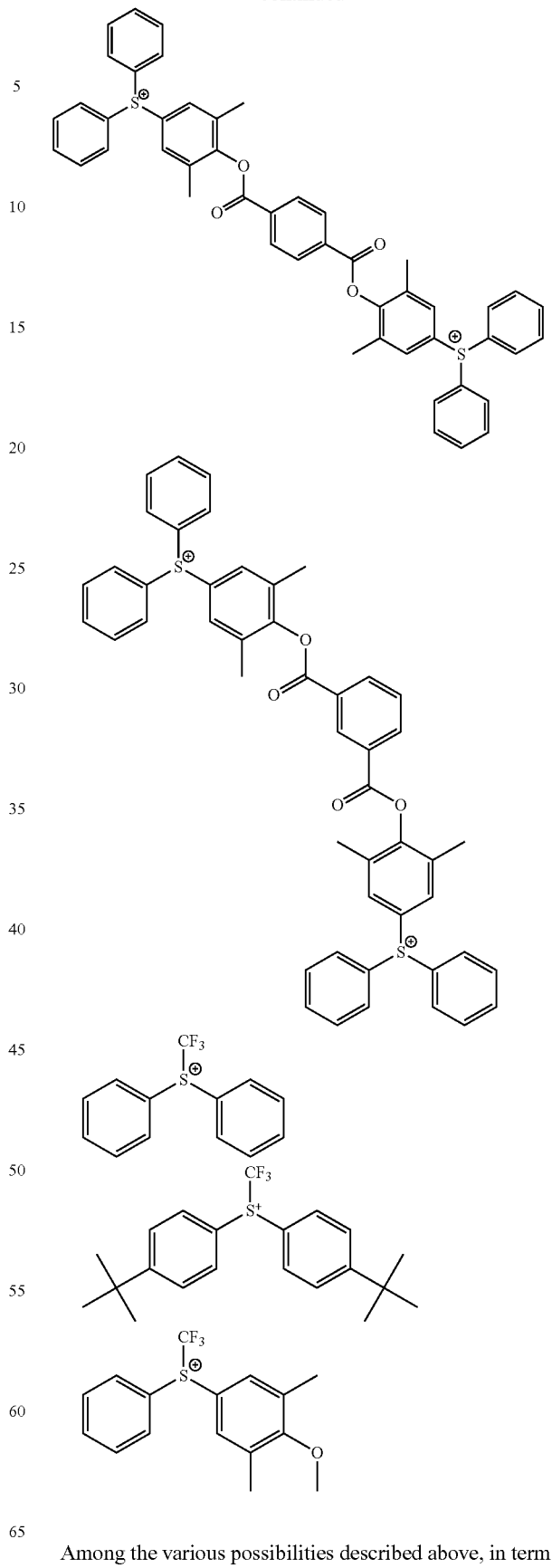
Among the various possibilities described above, in terms of achieving superior lithography properties and resist pattern shape upon formation of a resist composition, the component (B1) is preferably a compound represented by general formula (b1-1-0) shown below.

[Chemical Formual 66]

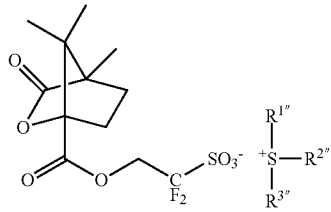

(b1-1-0)

In the formula, $R^{1''}$ to $R^{3''}$ are each the same as defined above.

A single component (B1) may be used alone, or two or more different types of the component (B1) may be used in combination.

The amount of the component (B1) within the resist composition of the present invention is preferably within a range from 1 to 60 parts by weight, more preferably from 3 to 50 parts by weight, and still more preferably from 5 to 40 parts by weight, per 100 parts by weight of the component (A).

Ensuring that the amount of the component (B1) is at least as large as the lower limit of the above range yields superior improvement in the lithography properties such as the roughness, mask reproducibility and exposure margin when a resist composition is formed, and also facilitates formation of a favorable resist pattern shape with a high degree of rectangularity. Provided the amount is not more than the upper limit of the above range, a uniform solution can be obtained and the storage stability of the composition improves.

The proportion of the component (B1) within the component (B), based on the total weight of the component (B), is preferably at least 20% by weight, and more preferably 40% by weight or more, and may be 100% by weight. A proportion of 100% by weight is the most preferred option. Provided the proportion of the component (B1) is at least as large as the lower limit of the above-mentioned range, the lithography properties can be further improved when a resist composition is formed. Further, a more favorable resist pattern shape can be obtained.

[Component (B2)]

In the resist composition of the present invention, if required, the component (B) may also include another acid generator (hereinafter referred to as "component (B2)") besides the component (B1).

As the component (B2), there are no particular limitations provided the acid generator falls outside the definition for component (B1), and any of the multitude of known acid generators may be used, including onium salt acid generators such as iodonium salts and sulfonium salts, oxime sulfonate acid generators, diazomethane acid generators such as bisalkyl or bisaryl sulfonyl diazomethanes and poly(bis-sulfonyl)diazomethanes, nitrobenzylsulfonate acid generators, iminosulfonate acid generators, and disulfone acid generators.

Preferred examples of the component (B2) include onium salt acid generators represented by general formulas (b-1) and (b-2) shown below.

[Chemical Formula 67]

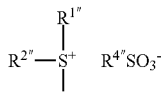

(b-1)

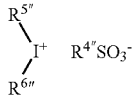

(b-2)

In the formulas, $R^{1''}$ to $R^{3''}$, $R^{5''}$ and $R^{6''}$ each independently represents an aryl group which may have a substituent, an alkyl group or an alkenyl group. Two of $R^{1''}$ to $R^{3''}$ in formula (b-1) may be bonded to each other to form a ring together with the sulfur atom in the formula. $R^{4''}$ represents a halogenated alkyl group, aryl group or alkenyl group, which may have a substituent.

In formula (b-1), $R^{1''}$ to $R^{3''}$ are the same as defined above for $R^{1''}$ to $R^{3''}$ in formula (b1-c1).

In formula (b-2), $R^{5''}$ and $R^{6''}$ are the same as defined above for $R^{5''}$ and $R^{6''}$ in formula (b1-c2).

In formulas (b-1) and (b-2), $R^{4''}$ represents a halogenated alkyl group which may have a substituent, an aryl group which may have a substituent, or an alkenyl group which may have a substituent.

Examples of the halogenated alkyl group for $R^{4''}$ include groups in which some or all of the hydrogen atoms within a linear, branched or cyclic alkyl group have been substituted with halogen atoms. Examples of the halogen atoms include fluorine atoms, chlorine atoms, bromine atoms and iodine atoms. Fluorine atoms are preferred.

When the alkyl group within the halogenated alkyl group is a linear or branched alkyl group, the alkyl group preferably contains 1 to 10 carbon atoms, more preferably 1 to 8 carbon atoms, and most preferably 1 to 4 carbon atoms, whereas when the alkyl group is a cyclic alkyl group, the cyclic alkyl group preferably contains 4 to 15 carbon atoms, more preferably 4 to 10 carbon atoms, and most preferably 6 to 10 carbon atoms.

In the halogenated alkyl group, the percentage of the number of halogen atoms relative to the total number of halogen atoms and hydrogen atoms within the halogenated alkyl group (namely, the halogenation ratio (%)) is preferably within a range from 10 to 100%, more preferably from 50 to 100%, and most preferably 100%. A higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that some or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula $X-Q^2-$ (wherein $Q^2$ represents a divalent linking group containing an oxygen atom, and X represents a hydrocarbon group of 3 to 30 carbon atoms which may have a substituent).

Examples of the halogen atom and alkyl group as substituents for $R^{4'''}$ include the same halogen atoms and alkyl groups as those described above with respect to the halogenated alkyl group for $R^{4'''}$.

Examples of the hetero atoms include an oxygen atom, a nitrogen atom, and a sulfur atom.

In the group represented by formula X-$Q^2$-, $Q^2$ represents a divalent linking group containing an oxygen atom.

$Q^2$ may contain atoms other than the oxygen atom. Examples of these atoms other than the oxygen atom include a carbon atom, hydrogen atom, sulfur atom or nitrogen atom.

Examples of divalent linking groups containing an oxygen atom include non-hydrocarbon, oxygen atom-containing linking groups such as an oxygen atom (an ether linkage, —O—), an ester linkage (—C(=O)—O—), an amido linkage (—C(=O)—NH—), a carbonyl group (—C(=O)—), a carbonate linkage (—O—C(=O)—O—), and combinations of these non-hydrocarbon, hetero atom-containing linking groups with an alkylene group.

Specific examples of these combinations include —$R^{91}$—O—, —$R^{92}$—O—C(=O)—, and —C(=O)—O—$R^{93}$—O—C(=O)— (wherein each of $R^{91}$ to $R^{93}$ independently represents an alkylene group).

The alkylene group for $R^{91}$ to $R^{93}$ is preferably a linear or branched alkylene group, and the alkylene group preferably has 1 to 12 carbon atoms, more preferably 1 to 5 carbon atoms, and most preferably 1 to 3 carbon atoms.

Specific examples of the alkylene group include a methylene group [—$CH_2$—], alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—, an ethylene group [—$CH_2CH_2$—], alkylethylene groups such as —CH($CH_3$)$CH_2$—, —CH($CH_3$)CH($CH_3$)—, —C($CH_3$)$_2CH_2$— and —CH($CH_2CH_3$)$CH_2$—, a trimethylene group (n-propylene group) [—$CH_2CH_2CH_2$—], alkyltrimethylene groups such as —CH($CH_3$)$CH_2CH_2$— and —$CH_2$CH($CH_3$)$CH_2$—, a tetramethylene group [—$CH_2CH_2CH_2CH_2$—], alkyltetramethylene groups such as —CH($CH_3$)$CH_2CH_2CH_2$— and —$CH_2$CH($CH_3$)$CH_2CH_2$—, and a pentamethylene group [—$CH_2CH_2CH_2CH_2CH_2$—].

$Q^2$ is preferably a divalent linking group containing an ester linkage or ether linkage, and is more preferably a group represented by —$R^{91}$—O—, —$R^{92}$—O—C(=O)— or —C(=O)—O—$R^{93}$—O—C(=O)—.

In the group represented by the formula X-$Q^2$-, the hydrocarbon group for X may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

Specific examples of the aromatic hydrocarbon group include aryl groups, which are aromatic hydrocarbon rings having one hydrogen atom removed therefrom, such as a phenyl group, biphenylyl group, fluorenyl group, naphthyl group, anthryl group or phenanthryl group, and alkylaryl groups such as a benzyl group, phenethyl group, 1-naphthylmethyl group, 2-naphthylmethyl group, 1-naphthylethyl group or 2-naphthylethyl group. The alkyl chain within the arylalkyl group preferably has 1 to 4 carbon atoms, more preferably 1 or 2 carbon atoms, and most preferably 1 carbon atom.

The aromatic hydrocarbon group may have a substituent. For example, some of the carbon atoms that constitute the aromatic ring within the aromatic hydrocarbon group may be substituted with a hetero atom, or a hydrogen atom bonded to the aromatic ring within the aromatic hydrocarbon group may be substituted with a substituent.

Examples of the former include heteroaryl groups in which some of the carbon atoms that constitute the ring within an aforementioned aryl group have been substituted with a hetero atom such as an oxygen atom, a sulfur atom or a nitrogen atom, and heteroarylalkyl groups in which some of the carbon atoms that constitute the aromatic hydrocarbon ring within an aforementioned arylalkyl group have been substituted with an aforementioned hetero atom.

In the latter example, examples of the substituent for the aromatic hydrocarbon group include an alkyl group, an alkoxy group, a halogen atom, a halogenated alkyl group, a hydroxyl group or an oxygen atom (=O) or the like.

The alkyl group as the substituent for the aromatic hydrocarbon group is preferably an alkyl group of 1 to 5 carbon atoms, and a methyl group, ethyl group, propyl group, n-butyl group or tert-butyl group is particularly desirable.

The alkoxy group as the substituent for the aromatic hydrocarbon group is preferably an alkoxy group having 1 to 5 carbon atoms, is more preferably a methoxy group, ethoxy group, n-propoxy group, iso-propoxy group, n-butoxy group or tert-butoxy group, and is most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group as the substituent for the aromatic hydrocarbon group include groups in which some or all of the hydrogen atoms within an aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, some of the carbon atoms that constitute the aliphatic hydrocarbon group may be substituted with a substituent group containing a hetero atom, or some or all of the hydrogen atoms that constitute the aliphatic hydrocarbon group may be substituted with a substituent group containing a hetero atom.

As this "hetero atom" within X, there is no particular limitation as long as it is an atom other than a carbon atom and a hydrogen atom. Examples of the hetero atom include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist solely of the hetero atom, or may be a group containing a group or atom other than a hetero atom.

Specific examples of the substituent group for substituting some of the carbon atoms include —O—, —C(=O)—O—, —C(=O)—, —O—C(=O)—O—, —C(=O)—NH—, —NH— (wherein H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups within the ring structure.

Examples of the substituent group for substituting some or all of the hydrogen atoms include an alkoxy group, a halogen atom, a halogenated alkyl group, a hydroxyl group, an oxygen atom (=O) and a cyano group.

The alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom include a fluorine atom, a chlorine atom, a bromine atom and an iodine atom, and a fluorine atom is preferable.

Examples of the halogenated alkyl group include groups in which some or all of the hydrogen atoms within an alkyl group of 1 to 5 carbon atoms (such as a methyl group, ethyl group, propyl group, n-butyl group or tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, ethyl group, propyl group, butyl group, pentyl group, hexyl group, heptyl group, octyl group, nonyl group, decyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group or docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group or 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, a propenyl group is particularly desirable as the unsaturated hydrocarbon group.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples of the aliphatic cyclic group include groups in which one or more hydrogen atoms have been removed from a monocycloalkane or a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and most preferably a group in which one or more hydrogen atoms have been removed from adamantane.

When the aliphatic cyclic group contains a hetero atom-containing substituent group in the ring structure, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 68]

(L1)

(L2)

(L3)

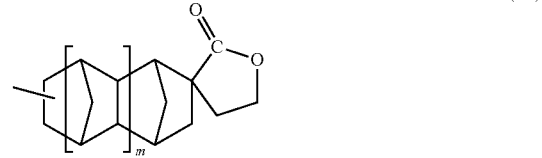

(L4)

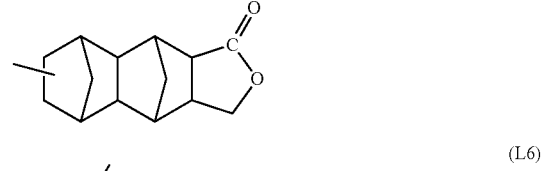

(L5)

(L6)

(S1)

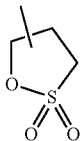
(S2)

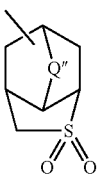
(S3)

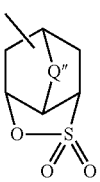
(S4)

In the above formulas, Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms), and m represents 0 or 1.

Examples of the alkylene groups for Q", $R^{94}$ and $R^{95}$ include the same alkylene groups as those described above for $R^{91}$ to $R^{93}$.

In these aliphatic cyclic groups, some of the hydrogen atoms bonded to the carbon atoms that constitute the ring structure may each be substituted with a substituent. Examples of this substituent include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, ethyl group, propyl group, n-butyl group or tert-butyl group is particularly desirable.

Examples of the alkoxy group and the halogen atom include the same groups and atoms as those exemplified above for the substituent group used for substituting some or all of the hydrogen atoms that constitute the aliphatic hydrocarbon group.

Of the above options, X is preferably a cyclic group which may have a substituent. This cyclic group may be either an aromatic hydrocarbon group which may have a substituent, or an aliphatic cyclic group which may have a substituent, although an aliphatic cyclic group which may have a substituent is preferable.

As the aromatic hydrocarbon group, a naphthyl group which may have a substituent or a phenyl group which may have a substituent is preferable.

As the aliphatic cyclic group which may have a substituent, an aliphatic polycyclic group which may have a substituent is preferable. As this aliphatic polycyclic group, groups in which one or more hydrogen atoms have been removed from an aforementioned polycycloalkane, and groups represented by formulas (L2) to (L5), and (S3) and (S4) above are preferable.

Further, in the present invention, X is preferably a group containing a polar region, as such groups yield improved lithography properties and a superior resist pattern shape.

Examples of these groups containing a polar region include groups in which a portion of the carbon atoms that constitute the aliphatic cyclic group of an aforementioned group X have been substituted with a substituent containing a hetero atom, namely with a substituent such as —O—, —C(=O)—O—, —C(=O)—, —O—C(=O)—O—, —C(=O)—NH—, —NH— (wherein H may be replaced with a substituent such as an alkyl group or acyl group), —S—, —S(=O)$_2$— or —S(=O)$_2$—O—.

In the present invention, $R^{4'''}$ preferably has X-$Q^2$- as a substituent. In such a case, $R^{4'''}$ is preferably a group represented by the formula X-$Q^2$-$Y^3$— (wherein $Q^2$ and X are the same as defined above, and $Y^3$ represents an alkylene group of 1 to 4 carbon atoms which may have a substituent, or a fluorinated alkylene group of 1 to 4 carbon atoms which may have a substituent).

In the group represented by the formula X-$Q^2$-$Y^3$—, examples of the alkylene group represented by $Y^3$ include those alkylene groups described above for $Q^2$ in which the number of carbon atoms is from 1 to 4.

Examples of the fluorinated alkylene group for $Y^3$ include groups in which some or all of the hydrogen atoms of an aforementioned alkylene group have been substituted with fluorine atoms.

Specific examples of $Y^3$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—, —CHF—, —$CH_2CF_2$—, —$CH_2CH_2CF_2$—, —$CH_2CF_2CF_2$—, —CH($CF_3$)$CH_2$—, —CH($CF_2CF_3$)—, —C($CH_3$)($CF_3$)—, —$CH_2CH_2CH_2CF_2$—, —$CH_2CH_2CF_2CF_2$—, —CH($CF_3$)$CH_2CH_2$—, —$CH_2CH(CF_3)CH_2$—, —CH($CF_3$)CH($CF_3$)—, —C($CF_3$)$_2CH_2$—, —$CH_2$—, —$CH_2CH_2$—, —$CH_2CH_2CH_2$—, —CH($CH_3$)$CH_2$—, —CH($CH_2CH_3$)—, —C($CH_3$)$_2$—, —$CH_2CH_2CH_2CH_2$—, —CH($CH_3$)$CH_2CH_2$—, —$CH_2CH(CH_3)CH_2$—, —CH($CH_3$)CH($CH_3$)—, —C($CH_3$)$_2CH_2$—, —CH($CH_2CH_3$)$CH_2$—, —CH($CH_2CH_2CH_3$)— and —C($CH_3$)($CH_2CH_3$)—.

$Y^3$ is preferably a fluorinated alkylene group, and more preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CH_2CF_2$—, —$CH_2CH_2CF_2$—, —$CH_2CF_2CF_2$—, —$CH_2CH_2CH_2CF_2$—, —$CH_2CH_2CF_2CF_2$— and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The expression that the alkylene group or fluorinated alkylene group "may have a substituent" means that some or all of the hydrogen atoms or fluorine atoms in the alkylene group or fluorinated alkylene group may be substituted, either with atoms other than hydrogen atoms and fluorine atoms, or with groups.

Examples of substituents with which the alkylene group or fluorinated alkylene group may be substituted include alkyl groups of 1 to 4 carbon atoms, alkoxy groups of 1 to 4 carbon atoms, and a hydroxyl group.

Specific examples of onium salt acid generators represented by formula (b-1) or (b-2) include diphenyliodonium trifluoromethanesulfonate or nonafluorobutanesulfonate, bis (4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, diphenyl(1-(4-methoxy)naphthyl)sulfonium trifluoromethanesulfonate, heptafluoropropanesulfonate or nonafluorobutanesulfonate, di(1-naphthyl)phenylsulfonium trifluoromethanesulfonate, heptafluoropropanesulfonate or nonafluorobutanesulfonate, 1-phenyltetrahydrothiophenium trifluoromethanesulfonate, heptafluoropropanesulfonate or nonafluorobutanesulfonate, 1-(4-methylphenyl)tetrahydrothiophenium trifluoromethanesulfonate, heptafluoropropanesulfonate or nonafluorobutanesulfonate, 1-(3,5-dimethyl-4-hydroxyphenyl)tetrahydrothiophenium trifluoromethanesulfonate, heptafluoropropanesulfonate or nonafluorobutanesulfonate, 1-(4-methoxynaphthalene-1-yl)tetrahydrothiophenium trifluoromethanesulfonate, heptafluoropropanesulfonate or nonafluorobutanesulfonate, 1-(4-ethoxynaphthalene-1-yl)tetrahydrothiophenium trifluoromethanesulfonate, heptafluoropropanesulfonate or nonafluorobutanesulfonate, 1-(4-n-butoxynaphthalene-1-yl)tetrahydrothiophenium trifluoromethanesulfonate, heptafluoropropanesulfonate or nonafluorobutanesulfonate, 1-phenyltetrahydrothiopyranium trifluoromethanesulfonate, heptafluoropropanesulfonate or nonafluorobutanesulfonate, 1-(4-hydroxyphenyl)tetrahydrothiopyranium trifluoromethanesulfonate, heptafluoropropanesulfonate or nonafluorobutanesulfonate, 1-(3,5-dimethyl-4-hydroxyphenyl)tetrahydrothiopyranium trifluoromethanesulfonate, heptafluoropropanesulfonate or nonafluorobutanesulfonate, and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts has been replaced by an alkylsulfonate such as methanesulfonate, n-propanesulfonate, n-butanesulfonate, n-octanesulfonate, 1-adamantanesulfonate or 2-norbornanesulfonate, or a sulfonate such as d-camphor-10-sulfonate, benzenesulfonate, perfluorobenzenesulfonate or p-toluenesulfonate.

Using an aforementioned onium salt acid generator in combination with the component (B1) enables an improvement in one or more properties during resist pattern formation, including the critical resolution, sensitivity, exposure margin (EL margin), mask error factor (MEF), line width roughness (LWR), line edge roughness (LER), circularity, critical dimension uniformity (CDU) or pattern shape.

Further, as the component (B2), examples of particularly preferred acid generators among the onium salt acid generators represented by the above general formulas (b-1) and (b-2) include onium salt acid generators in which the anion moiety is represented by one of the formulas (b1) to (b8) shown below.

Using these onium salt acid generators in combination with the component (B1) enables an improvement in one or more properties during resist pattern formation, including the critical resolution, sensitivity, EL margin, MEF, LWR, LER, circularity, CDU or pattern shape.

[Chemical Formula 69]

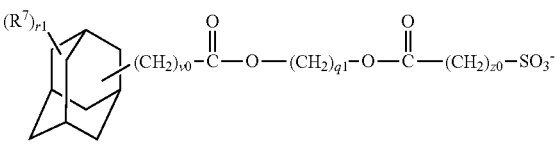

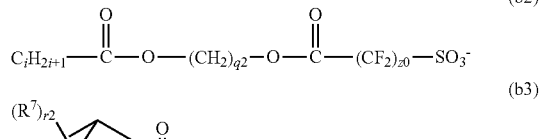

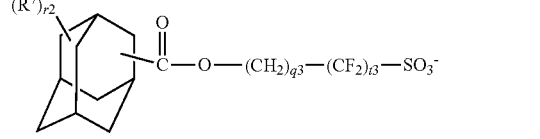

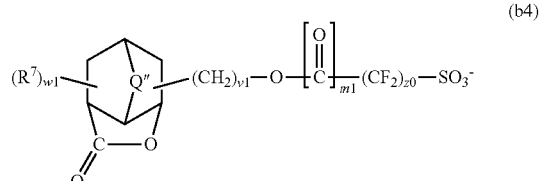

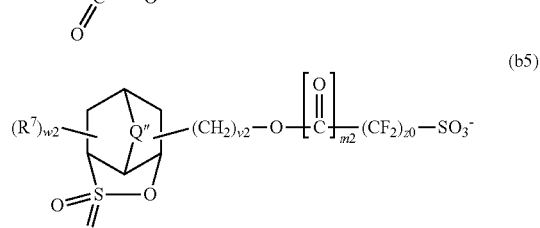

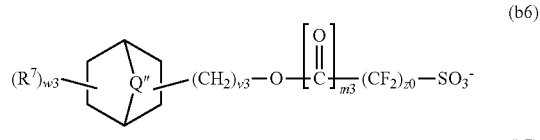

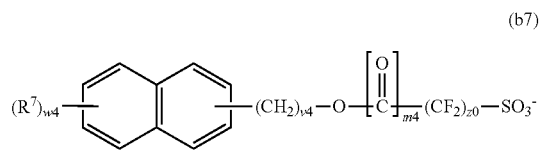

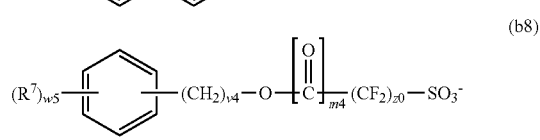

In the formulas, z0 represents an integer of 1 to 3, each of q1 and q2 independently represents an integer of 1 to 5, q3 represents an integer of 1 to 12, t3 represents an integer of 1 to 3, each of r1 and r2 independently represents an integer of 0 to 3, i represents an integer of 1 to 20, $R^7$ represents a substituent, each of m1 to m5 independently represents 0 or 1, each of v0 to v5 independently represents an integer of 0 to 3, each of w1 to w5 independently represents an integer of 0 to 3, and Q" is the same as defined above.

Examples of the substituent for $R^7$ include the same groups as those which the aforementioned aliphatic hydrocarbon group or aromatic hydrocarbon group for X may have as a substituent.

If there are two or more $R^7$ groups, as indicated by the values r1, r2 and w1 to w5, then the plurality of $R^7$ groups within the compound may be the same or different from each other.

Further, onium salt acid generators in which the anion moiety in the above general formula (b-1) or (b-2) has been replaced with an anion moiety represented by general formula (b-3) or (b-4) shown below can also be used favorably as the component (B2). Using these onium salt acid generators in combination with the component (B1) enables an improvement in one or more properties during resist pattern formation, including the critical resolution, sensitivity, EL margin, MEF, LWR, LER, circularity, CDU or pattern shape.

[Chemical Formula 70]

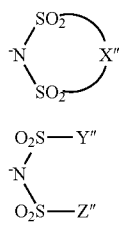

(b-3)

$$O_2S—Y''$$
$$\phantom{O_2S}\diagdown$$
$$\phantom{O_2S}N$$
$$\phantom{O_2S}\diagup$$
$$O_2S—Z''$$

(b-4)

In the formulas, X" represents an alkylene group of 2 to 6 carbon atoms in which at least one hydrogen atom has been substituted with a fluorine atom, and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, wherein the alkylene group contains 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, wherein the alkyl group contains 1 to 10 carbon atoms, preferably 1 to 7 carbon atoms, and most preferably 1 to 3 carbon atoms.

The smaller the number of carbon atoms in the alkylene group for X" or the alkyl group for Y" and Z" within the above numerical ranges for the number of carbon atoms, the more the solubility in a resist solvent is improved, and therefore a smaller number of carbon atoms is preferred.

Further, in the alkylene group for X" or the alkyl group for Y" and Z", it is preferable that the number of hydrogen atoms substituted with fluorine atoms is as large as possible, because the acid strength increases and the transparency to high energy radiation of 200 nm or less and electron beams is improved.

The fluorination ratio of the alkylene group or alkyl group is preferably within a range from 70 to 100%, and more preferably from 90 to 100%. A perfluoroalkylene or perfluoroalkyl group in which all the hydrogen atoms are substituted with fluorine atoms is the most desirable.

As the onium salt acid generator of the component (B2), onium salts of the above general formula (b-1) or (b-2) in which the anion moiety ($R^{4\prime\prime}SO_3^-$) has been substituted with $R^a$—$COO^-$ (wherein $R^a$ represents an alkyl group or a fluorinated alkyl group) (and in which the cation moiety is the same as that of general formula (b-1) or (b-2)) may also be used.

Specific examples of the group $R^a$ in the above formula include the same groups as those listed above for $R^{4\prime\prime}$.

Specific examples of $R^a$—$COO^-$ include a trifluoroacetate ion, an acetate ion, and a 1-adamantanecarboxylate ion.

Furthermore, in those cases where the cation moiety is represented by one of the aforementioned general formulas (I-1), (I-2), (I-5) or (I-6), onium salt acid generators in which the anion moiety has been replaced with a fluorinated alkylsulfonate ion such as the anion moiety shown in general formula (b-1) and (b-2) ($R^{4\prime\prime}SO_3^-$), an anion of formula (b1) to (b8), or an anion represented by the above general formula (b-3) or (b-4) may also be used.

Using these onium salt acid generators in combination with the component (B1) enables an improvement in one or more properties during resist pattern formation, including the critical resolution, sensitivity, EL margin, MEF, LWR, LER, circularity, CDU or pattern shape.

In the present description, an oxime sulfonate acid generator is a compound having at least one group represented by general formula (B-1) shown below, and has a feature of generating acid by irradiation. Such oxime sulfonate acid generators can also be used favorably as the component (B2). Using an oxime sulfonate acid generator in combination with the component (B1) enables an improvement in all manner of properties during resist pattern formation, including the critical resolution, sensitivity, EL margin, MEF, LWR, LER, circularity, CDU or pattern shape.

[Chemical Formula 71]

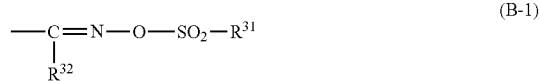

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (such as a hydrogen atom, oxygen atom, nitrogen atom, sulfur atom or halogen atom (such as a fluorine atom or chlorine atom) or the like).

As the organic group for $R^{31}$, a linear, branched, or cyclic alkyl group or aryl group is preferable. The alkyl group or aryl group may have a substituent. There are no particular limitations on the substituent, and examples thereof include a fluorine atom and a linear, branched or cyclic alkyl group of 1 to 6 carbon atoms. The expression that the alkyl group or aryl group "may have a substituent" means that some or all of the hydrogen atoms of the alkyl group or aryl group may be substituted with substituents.

The alkyl group preferably contains 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably contains 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of the hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched or cyclic alkyl group, an aryl group, or a cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent, or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 72]

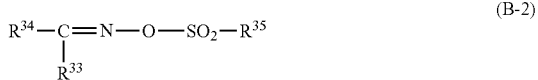

(B-2)

In formula (B-2), $R^{33}$ represents a cyano group, an alkyl group having no substituent or a halogenated alkyl group, $R^{34}$ represents an aryl group, and $R^{35}$ represents an alkyl group having no substituent or a halogenated alkyl group.

[Chemical Formula 73]

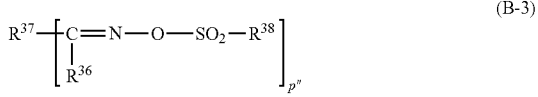

(B-3)

In formula (B-3), $R^{36}$ represents a cyano group, an alkyl group having no substituent or a halogenated alkyl group, $R^{37}$ represents a divalent or trivalent aromatic hydrocarbon group, $R^{38}$ represents an alkyl group having no substituent or a halogenated alkyl group, and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more fluorinated, and most preferably 90% or more fluorinated.

Examples of the aryl group for $R^{34}$ include groups in which one hydrogen atom has been removed from an aromatic hydrocarbon ring, such as a phenyl group, biphenylyl group, fluorenyl group, naphthyl group, anthryl group or phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group or halogenated alkyl group as the substituent preferably contains 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably contains 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more fluorinated, and still more preferably 90% or more fluorinated. A completely fluorinated alkyl group in which 100% of the hydrogen atoms have been substituted with fluorine atoms is particularly desirable.

In general formula (B-3), examples of the alkyl group having no substituent and the halogenated alkyl group for $R^{36}$ include the same groups as those described above for the alkyl group having no substituent and the halogenated alkyl group for $R^{33}$.

Examples of the divalent or trivalent aromatic hydrocarbon group for $R^{37}$ include groups in which an additional one or two hydrogen atoms have been removed from the aryl group for $R^{34}$.

Examples of the alkyl group having no substituent or the halogenated alkyl group for $R^{38}$ include the same groups as those described above for the alkyl group having no substituent or the halogenated alkyl group for $R^{35}$.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei-09-208554 (Chemical Formulas 18 and 19 shown in paragraphs [0012] to [0014]) and oxime sulfonate-based acid generators disclosed in WO 04/074242 pamphlet (Examples 1 to 40 described on pages 65 to 85) may also be used favorably.

Furthermore, the following compounds may also be used as preferred examples.

[Chemical Formula 74]

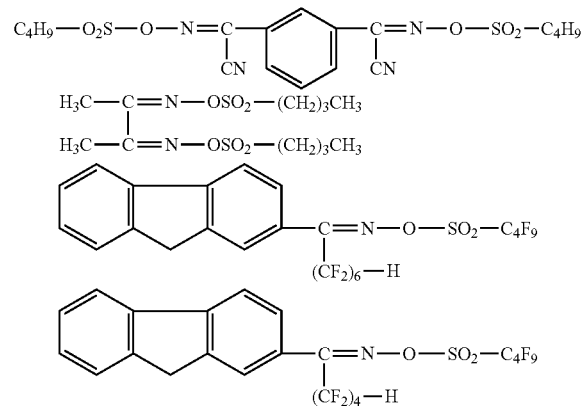

Of the above-mentioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei-11-035551, Japanese Unexamined Patent Application, First Publication No. Hei-11-035552 and Japanese Unexamined Patent Application, First Publication No. Hei-11-035573 may also be used favorably.

Furthermore, examples of poly(bis-sulfonyl)diazomethanes include those disclosed in Japanese Unexamined Patent Application, First Publication No. Hei-11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B2), one type of acid generator described above may be used alone, or two or more types of acid generators may be used in combination.

The total amount of the overall component (B) within the resist composition of the present invention is preferably within a range from 1 to 60 parts by weight, more preferably from 3 to 50 parts by weight, and still more preferably from 5 to 40 parts by weight, relative to 100 parts by weight of the component (A). When the amount of the component (B) is within the above-mentioned range, formation of a resist pattern can be performed satisfactorily. Further, a uniform solution can be obtained and the storage stability tends to improve.

<Optional Components>
[Component (D)]

The resist composition of the present invention preferably further includes a nitrogen-containing organic compound (D) (hereinafter referred to as "component (D)") as an optional component.

There are no particular limitations on the component (D) provided it functions as an acid diffusion control agent, namely, a quencher which traps the acid generated from the component (B) upon exposure. A multitude of these components (D) have already been proposed, and any of these known compounds may be used. Among these conventional compounds, an aliphatic amine, and particularly a secondary aliphatic amine, tertiary aliphatic amine or aromatic amine is preferable.

An "aliphatic amine" is an amine having one or more aliphatic groups, and each of the aliphatic groups preferably contains 1 to 12 carbon atoms.

Examples of these aliphatic amines include amines in which at least one hydrogen atom of ammonia ($NH_3$) has been substituted with an alkyl group or hydroxyalkyl group of not more than 12 carbon atoms (namely, alkylamines or alkyl alcohol amines), and cyclic amines.

Specific examples of the alkylamines and alkyl alcohol amines include monoalkylamines such as n-hexylamine, n-heptylamine, n-octylamine, n-nonylamine and n-decylamine, dialkylamines such as diethylamine, di-n-propylamine, di-n-heptylamine, di-n-octylamine and dicyclohexylamine, trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine and tri-n-dodecylamine, and alkyl alcohol amines such as diethanolamine, triethanolamine, diisopropanolamine, triisopropanolamine, di-n-octanolamine and tri-n-octanolamine. Among these, trialkylamines of 5 to 10 carbon atoms are preferred, and tri-n-pentylamine or tri-n-octylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Other aliphatic amines besides those described above may also be used. Examples of these other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, and tris[2-{2-(2-hydroxyethoxy)ethoxy}ethyl]amine.

Further, examples of the aromatic amine include aniline-based compounds such as aniline, N,N-n-butylaniline, 2,6-diisopropylaniline, N-isopropylaniline, 3-isopropoxyaniline and N-ethylaniline, as well as pyridine, 4-dimethylaminopyridine, pyrrole, indole, pyrazole, imidazole and derivatives thereof, diphenylamine, triphenylamine, and tribenzylamine.

As the component (D), a single compound may be used alone, or two or more different compounds may be used in combination.

The component (D) is typically used in an amount within a range from 0.01 to 5.0 parts by weight, relative to 100 parts by weight of the component (A). By ensuring that the amount of the component (D) is within the above-mentioned range, the shape of the resist pattern and the post exposure stability of the latent image formed by the pattern-wise exposure of the resist layer are improved.

[Component (E)]

In the resist composition of the present invention, for the purposes of preventing any deterioration in sensitivity, and improving the resist pattern shape and the post exposure stability of the latent image formed by the pattern-wise exposure of the resist layer, at least one compound (E) (hereinafter referred to as "component (E)") selected from the group consisting of organic carboxylic acids, and phosphorus oxo acids and derivatives thereof may be added as an optional component.

Examples of the organic carboxylic acids include acetic acid, malonic acid, citric acid, malic acid, succinic acid, benzoic acid and salicylic acid.

Examples of the phosphorus oxo acids include phosphoric acid, phosphonic acid and phosphinic acid. Among these, phosphonic acid is particularly desirable.

Examples of the phosphorus oxo acid derivatives include esters in which a hydrogen atom within an aforementioned oxo acid is substituted with a hydrocarbon group. Examples of the hydrocarbon group include alkyl groups of 1 to 5 carbon atoms and aryl groups of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, diphenyl phosphonate and dibenzyl phosphonate, as well as phenylphosphonic acid.

Examples of phosphinic acid derivatives include phosphinate esters and phenylphosphinic acid.

As the component (E), one compound may be used alone, or two or more different compounds may be used in combination.

The component (E) is preferably an organic carboxylic acid, and is most preferably salicylic acid.

The component (E) is typically used in an amount within a range from 0.01 to 5.0 parts by weight relative to 100 parts by weight of the component (A).

If desired, other miscible additives besides those described above may also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the components that constitute the resist composition in an organic solvent (S) (hereinafter, frequently referred to as "component (S)").

The component (S) may be any organic solvent which can dissolve the respective components to give a uniform solution, and one or more types of organic solvent may be selected appropriately from those solvents which have been conventionally known as solvents for chemically amplified resists.

Examples of the component (S) include lactones such as γ-butyrolactone; ketones such as acetone, methyl ethyl ketone, cyclohexanone (CH), methyl-n-pentyl ketone, methyl isopentyl ketone, and 2-heptanone; polyhydric alcohols such as ethylene glycol, diethylene glycol, propylene glycol and dipropylene glycol; polyhydric alcohol derivatives, including compounds having an ester bond such as ethylene glycol monoacetate, diethylene glycol monoacetate, propylene glycol monoacetate and dipropylene glycol monoacetate, and compounds having an ether bond such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene.

As the component (S), one the above organic solvents may be used alone, or two or more solvents may be used as a mixed solvent.

Among these, cyclohexanone (CH), γ-butyrolactone, propylene glycol monomethyl ether acetate (PGMEA), propylene glycol monomethyl ether (PGME) and ethyl lactate (EL) are preferable, and γ-butyrolactone, PGMEA and PGME are particularly desirable.

Furthermore, a mixed solvent obtained by mixing PGMEA with a polar solvent is also preferable. The mixing ratio (weight ratio) of this mixed solvent can be determined appropriately with due consideration of the compatibility of the PGMEA with the polar solvent, but is preferably in the range of 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME ratio is preferably from 1:9 to 9:1, more preferably from 2:8 to 8:2, and still more preferably from 3:7 to 7:3. When cyclohexanone (CH) is mixed as the polar solvent, the PGMEA:CH ratio is preferably from 1:9 to 9:1, and more preferably from 2:8 to 9:1.

Further, as the component (S), a mixed solvent of at least one of PGMEA and EL with γ-butyrolactone is also preferable. The mixing ratio (former:latter) of such a mixed solvent is preferably from 70:30 to 95:5.

The amount used of the component (S) is not particularly limited, and may be adjusted appropriately to a concentration which enables application of a coating solution onto a substrate in accordance with the thickness of the coating film. In general, the organic solvent is used in an amount that yields a solid fraction concentration for the resist composition that is within a range from 0.5 to 20% by weight, and preferably from 1 to 15% by weight.

Dissolution of the components that constitute the resist composition in the component (S) can be conducted by simply mixing and stirring each of the above components together using conventional methods. If necessary, the composition may also be mixed and dispersed using a dispersion device such as a dissolver, homogenizer or triple roll mill. Furthermore, following mixing, the composition may also be filtered using a mesh or membrane filter or the like.

As described above, the resist composition of the present invention yields excellent lithography properties such as roughness, mask reproducibility and exposure margin during formation of a resist composition, and can form a resist pattern having a favorable shape with a high degree of rectangularity. Although the reasons that these effects are obtained are not entirely clear, they are thought to include the following.

The resist composition of the present invention includes the acid generator (B1) containing a compound represented by general formula (b1-1).

The component (B1) has an anion moiety that includes a camphane structure in which the —C—O— moiety within a —C(=O)—O— structure forms a portion of a cyclic group, wherein a —C(=O)—O—CH$_2$—CF$_2$—SO$_3^-$ group is bonded to the camphane structure.

Because this camphane structure is highly polar and very bulky, the component (B1) tends to have shorter diffusion properties than conventional acid generators with fluorinated alkylsulfonate ions such as $C_4F_9SO_3^-$ as the anion moiety. Further, because the interaction with the base component (A) is enhanced, the component (B1) is able to be distributed uniformly through the resist film.

Further, because there is only a single CH$_2$ within the —C(=O)—O—CH$_2$—CF$_2$—SO$_3^-$ structure, the diffusion length of the acid generated upon exposure can be better controlled than structures that contain a plurality of CH$_2$ groups, and therefore properties such as the ultra fine resolution performance, mask reproducibility and exposure margin can be improved.

It is thought that as a result of the above effects, the resist composition of the present invention which contains the component (B1) yields excellent lithography properties and can form a resist pattern having a favorable shape.

In the resist composition of the present invention, by combining the component (B1) with a polymeric compound containing the structural unit (a0) as the component (A), the interaction between the two components yields enhanced adhesion of the resist film to the substrate, and superior improvement in the lithography properties such as the roughness, the mask reproducibility and the exposure margin.

<<Method of Forming Resist Pattern>>

The method of forming a resist pattern according to the second aspect of the present invention includes: forming a resist film on a substrate using the resist composition of the present invention described above, conducting exposure of the resist film, and alkali-developing the resist film to form a resist pattern.

More specifically, the method of forming a resist pattern according to the present invention can be performed, for example, as follows.

Firstly, the resist composition is applied onto a substrate using a spinner or the like, and a prebake (post applied bake (PAB)) is conducted under temperature conditions of 80 to 150° C. for 40 to 120 seconds, and preferably 60 to 90 seconds, to form a resist film. Then, the resist film is selectively exposed, either by exposure through a mask pattern using an exposure apparatus such as an ArF exposure apparatus, an electron beam lithography apparatus or an EUV exposure apparatus, or by patterning via direct irradiation with an electron beam without using a mask pattern, followed by post exposure baking (PEB) under temperature conditions of 80 to 150° C. for 40 to 120 seconds, and preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, a bake treatment (post bake) may be conducted following the alkali-developing treatment. In this manner, a resist pattern that is faithful to the mask pattern can be obtained.

There are no particular limitations on the substrate, and a conventionally known substrate may be used. For example, substrates for electronic components, and such substrates having wiring patterns formed thereon can be used. Specific examples of the material of the substrate include metals such as silicon wafer, copper, chromium, iron and aluminum, as well as glass. Suitable materials for the wiring pattern include copper, aluminum, nickel, and gold.

Further, as the substrate, any one of the above-mentioned substrates provided with an inorganic and/or organic film on the surface thereof may also be used. As the inorganic film, an inorganic antireflection film (inorganic BARC) can be used. As the organic film, an organic antireflection film (organic BARC) can be used.

The wavelength to be used for exposure is not particularly limited, and the exposure can be conducted using radiation such as ArF excimer laser, KrF excimer laser, F$_2$ excimer laser, extreme ultraviolet rays (EUV), vacuum ultraviolet rays (VUV), electron beam (EB), X-rays, and soft X-rays.

The resist composition of the present invention is more effective for use with a KrF excimer laser, ArF excimer laser, EB or EUV, and is particularly effective for an ArF excimer laser, EB or EUV.

The exposure of the resist film may employ either a general exposure method (dry exposure) conducted in air or an inert gas such as nitrogen, or a liquid immersion lithography method.

In liquid immersion lithography, exposure is conducted in a state where the region between the lens and the resist film formed on the wafer, which is conventionally filled with air or an inert gas such as nitrogen, is filled with a solvent (an immersion medium) that has a larger refractive index than the refractive index of air.

More specifically, in liquid immersion lithography, the region between the resist film formed in the aforementioned manner and the lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point that is preferably within a range from 70 to 180° C., and more preferably from 80 to 160° C. A fluorine-based inert liquid having a boiling point within the above-mentioned range is advantageous in that the removal of the immersion medium after the exposure can be conducted by a simple method.

As the fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point: 102° C.), and one example of a suitable perfluoroalkylamine compound is perfluorotributylamine (boiling point: 174° C.).

The method of forming a resist pattern according to the present invention can also be applied to double exposure methods and double patterning methods.

<<Compound>>

The compound of the third aspect of the present invention is a compound represented by general formula (b1-1) shown below, and is the same as the component (B1) included within the resist composition of the first aspect of the present invention.

[Chemical Formual 75]

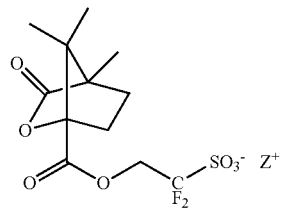

(b1-1)

In the formula, $Z^+$ represents an organic cation.

The description of this compound of the present invention is the same as the above description relating to the component (B1).

(Method of Producing the Compound)

In the following description, a compound represented by chemical formula (1) is designated as "compound (1)", and the same naming convention applies for compounds represented by other formulas.

The compound (b1-1) of the present invention can be produced by reacting a compound (b1-0) and a compound (1') shown below.

[Chemical Formula 76]

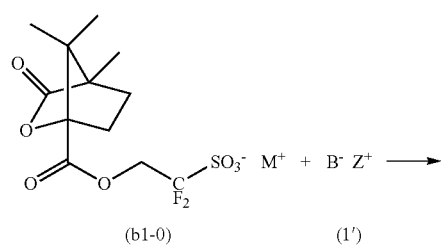

(b1-0)        (1')

-continued

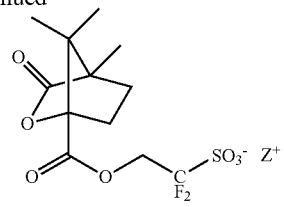

(b1-1)

In the above formulas, $Z^+$ is the same as defined above for $Z^+$ in formula (b1-1). $M^+$ represents an alkali metal ion or an ammonium ion which may have a substituent. $B^-$ represents a non-nucleophilic ion.

In the above formula (b1-0), $M^+$ represents an alkali metal ion or an ammonium ion which may have a substituent.

Examples of the alkali metal ion for $M^+$ include a sodium ion, lithium ion or potassium ion. Of these, a sodium ion or lithium ion is preferred.

Examples of the ammonium ion which may have a substituent for $M^+$ include ions represented by general formula (b1-c0) shown below.

[Chemical Formula 77]

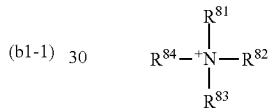

(b-1-c0)

In the formula, each of $R^{81}$ to $R^{84}$ independently represents a hydrogen atom or a hydrocarbon group which may have a substituent, provided that at least one of $R^{81}$ to $R^{84}$ represents a hydrocarbon group. Two of $R^{81}$ to $R^{84}$ may be bonded to each other to form a ring.

In the above formula (b1-c0), each of $R^{81}$ to $R^{84}$ independently represents a hydrogen atom or a hydrocarbon group which may have a substituent, provided that at least one of $R^{81}$ to $R^{84}$ represents a hydrocarbon group.

Examples of the hydrocarbon group for $R^{81}$ to $R^{84}$ include the same hydrocarbon groups as those described above for X.

The hydrocarbon group may be either an aliphatic hydrocarbon group or an aromatic hydrocarbon group. When the hydrocarbon group is an aliphatic hydrocarbon group, the aliphatic hydrocarbon group is preferably an alkyl group of 1 to 12 carbon atoms which may have a substituent.

At least one of $R^{81}$ to $R^{84}$ represents an above mentioned hydrocarbon group, and two or three of $R^{81}$ to $R^{84}$ are preferably above mentioned hydrocarbon groups.

At least two of $R^{81}$ to $R^{84}$ may be bonded to each other to form a ring. For example, two of $R^{81}$ to $R^{84}$ may be bonded to each other to form a single ring, three of $R^{81}$ to $R^{84}$ may be bonded to each other to form a single cyclic structure, or two pairs of $R^{81}$ to $R^{84}$ may be respectively bonded to each other to form two separate rings.

The ring that is formed when at least two of $R^{81}$ to $R^{84}$ are bonded to each other to form a ring together with the nitrogen atom in the formula (namely, a heterocyclic ring including the nitrogen atom as a hetero atom) may be an aliphatic heterocyclic ring or an aromatic heterocyclic ring. Further, the heterocyclic ring may be either monocyclic or polycyclic.

Specific examples of the ammonium ion represented by formula (b1-c0) include ammonium ions derived from an amine.

In this description, an "ammonium ion derived from an amine" include cations formed by bonding a hydrogen atom to the nitrogen atom of an amine, and quaternary ammonium ions formed by bonding another substituent to the nitrogen atom of an amine.

The amine that gives rise to the above ammonium ion may be either an aliphatic amine or an aromatic amine.

Examples of the aliphatic amine include amines in which at least one hydrogen atom of ammonia ($NH_3$) has been substituted with an alkyl group or hydroxyalkyl group of not more than 12 carbon atoms (namely, alkylamines or alkyl alcohol amines), and cyclic amines.

Specific examples of the alkylamines and alkyl alcohol amines include monoalkylamines such as n-hexylamine, n-heptylamine, n-octylamine, n-nonylamine and n-decylamine, dialkylamines such as diethylamine, di-n-propylamine, di-n-heptylamine, di-n-octylamine and dicyclohexylamine, trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine, and alkyl alcohol amines such as diethanolamine, triethanolamine, diisopropanolamine, triisopropanolamine, di-n-octanolamine and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Examples of the aromatic amines include aniline, pyridine, 4-dimethylaminopyridine (DMAP), pyrrole, indole, pyrazole and imidazole.

Specific examples of the quaternary ammonium ion include a tetramethylammonium ion, tetraethylammonium ion and tetrabutylammonium ion.

As the ammonium ion represented by formula (b1-c0), ammonium ions in which at least one of $R^{81}$ to $R^{84}$ represents an alkyl group and at least one of $R^{81}$ to $R^{84}$ represents a hydrogen atom are preferable.

Among these, ammonium ions in which three of $R^{81}$ to $R^{84}$ represent alkyl groups and the remaining one of $R^{81}$ to $R^{84}$ represents a hydrogen atom (namely, trialkylammonium ions), and ammonium ions in which two of $R^{81}$ to $R^{84}$ represent alkyl groups and one of the remainder represents a hydrogen atom (namely, dialkylammonium ions) are particularly desirable.

Each of the alkyl groups within a trialkylammonium ion or dialkylammonium ion preferably independently represents an alkyl group of 1 to 10 carbon atoms, more preferably an alkyl group of 1 to 8 carbon atoms, and most preferably an alkyl group of 1 to 5 carbon atoms. Specific examples include a methyl group, ethyl group, propyl group, butyl group, pentyl group, hexyl group, heptyl group, octyl group, nonyl group and decanyl group. Among these, an ethyl group is the most preferred.

In the above formula (1'), $B^-$ represents a non-nucleophilic ion.

Examples of the non-nucleophilic ion include halide ions such as a bromide ion or chloride ion, ions that yield an acid with lower acidity than the compound (b1-0), $BF_4^-$, $AsF_6^-$, $SbF_6^-$, $PF_6^-$ and $ClO_4^-$.

Examples of ions for $B^-$ that yield an acid with lower acidity than the compound (b1-0) include sulfonate ions such as a p-toluenesulfonate ion, methanesulfonate ion or benzenesulfonate ion.

Reaction of Compound (b1-0) and Compound (1')

The compound (b1-0) and the compound (1') can be reacted, for example, by dissolving the two compounds in a solvent such as water, dichloromethane, acetonitrile, methanol, chloroform or methylene chloride, and then stirring the resulting solution.

The reaction temperature is preferably within a range from approximately 0 to 150° C., and more preferably from approximately 0 to 100° C. The reaction time varies depending on the reactivity between the compound (b1-0) and the compound (1'), and the reaction temperature and the like, but in most cases, is preferably within a range from 0.5 to 48 hours, and more preferably from 1 to 24 hours.

The amount of the compound (1') used in the above reaction is preferably within a range from approximately 0.5 to 2 mols per 1 mol of the compound (b1-0).

Following completion of the reaction, the compound (b1-1) within the reaction solution may be isolated and purified. Conventional methods may be used to isolate and purify the product, including concentration, solvent extraction, distillation, crystallization, recrystallization and chromatography, which may be used individually or in combinations of two or more different methods.

The compound (b1-0) can be produced, for example, using one of the methods (I) to (III) described below.

Method (I): (–)-camphanic acid and $HO-CH_2-CF_2-SO_3^-.Na^+$ are subjected to a dehydration-condensation reaction in the presence of a condensation agent (such as diisopropylcarbodiimide), and an alkali corresponding with $M^+$ in formula (b1-0) is then added. One example of this synthesis route is shown below.

[Chemical Formula 78]

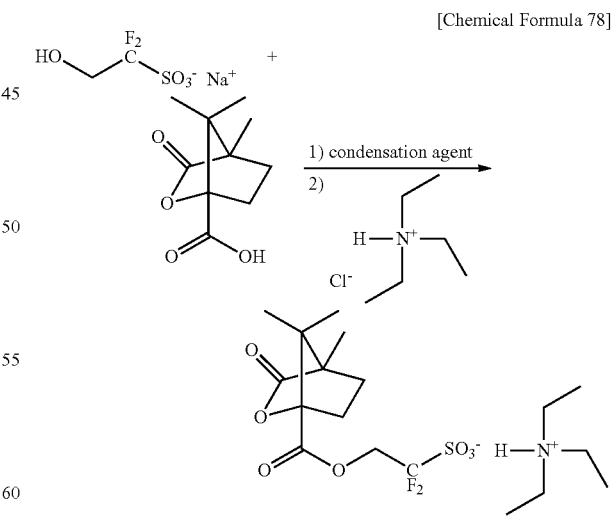

Method (II): (–)-camphanic acid chloride and $HO-CH_2-CF_2-SO_3^-.Na^+$ are reacted in the presence of a base catalyst, and an alkali corresponding with $M^+$ in formula (b1-0) is then added. One example of this synthesis route is shown below.

[Chemical Formula 79]

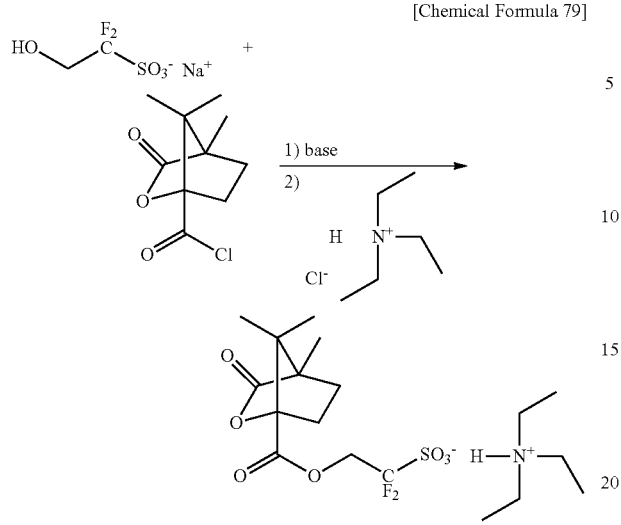

Method (III): (−)-camphanic acid chloride and HO—CH$_2$—CF$_2$—Br are reacted in the presence of a base catalyst, Na$_2$S$_2$O$_4$ is then added, and following substitution of the terminal group, an oxidation reaction is performed. One example of this synthesis route is shown below.

[Chemical Formula 80]

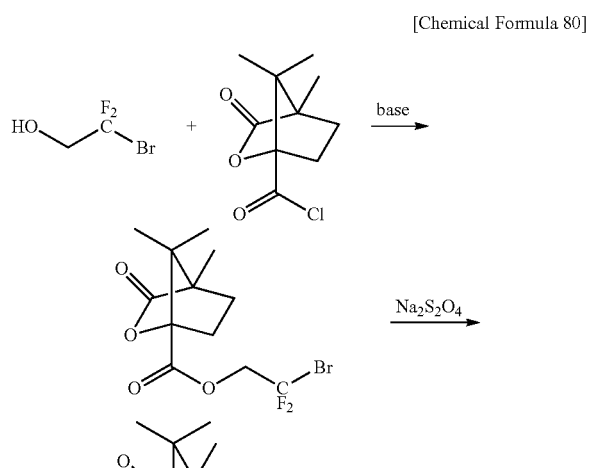

The structure of the compound of the present invention and the intermediate products obtained in the manner described above can be confirmed by general organic analysis methods such as $^1$H nuclear magnetic resonance (NMR) spectrometry, $^{13}$C-NMR spectrometry, $^{19}$F-NMR spectrometry, infrared (IR) absorption spectrometry, mass spectrometry (MS), elemental analysis methods, and X-ray crystal diffraction analysis.

The compound of the present invention described above is a novel compound that is useful as an acid generator for resist compositions, and can be added to a resist composition as an acid generator.

<<Acid Generator>>

The acid generator according to the fourth aspect of the present invention is an acid generator including the compound represented by general formula (b1-1).

This acid generator is useful as an acid generator for a chemically amplified resist composition, such as the acid generator component (B) of the resist composition according to the first aspect of the present invention.

EXAMPLES

A more detailed description of the present invention is presented below based on a series of examples, although the scope of the present invention is in no way limited by these examples.

In the following examples, a compound represented by a chemical formula (1) is designated as "compound (1)", and the same naming convention applies for compounds represented by other formulas.

Synthesis of Novel Compounds

Examples 1 to 48

Novel compounds of the present invention were synthesized using the method described in the following examples.

In the examples, for the NMR analyses, tetramethylsilane (TMS) was used as an internal standard for $^1$H-NMR, and hexafluorobenzene was used as an internal standard for $^{19}$F-NMR (with the hexafluorobenzene peak designated as −160 ppm).

Example 1

Synthesis of Compound (B1-1-1)

i) Synthesis of Compound (2)

Under an atmosphere of nitrogen, (−)-camphanic acid (7.9 g) and pyridine (40 g) were combined and cooled to 5° C. Diisopropylcarbodiimide (6.6 g) was then added, and the resulting mixture was stirred for 10 minutes at 5° C. Subsequently, the compound (1) (3.7 g) was added gradually to the reaction mixture, and reaction was allowed to proceed for 6 hours at 5° C.

Pure water (115 g) was then added to the reaction mixture, and following stirring for 30 minutes, the precipitated diisopropylurea was removed by filtration. The filtrate was collected, and triethylamine hydrochloride (5 g) was then added to the filtrate and stirred for 1 hour at room temperature. The reaction mixture was then extracted into dichloromethane (80 g) and washed with pure water, and the dichloromethane layer was concentrated and dried, yielding the compound (2) (7.1 g).

[Chemical Formula 81]

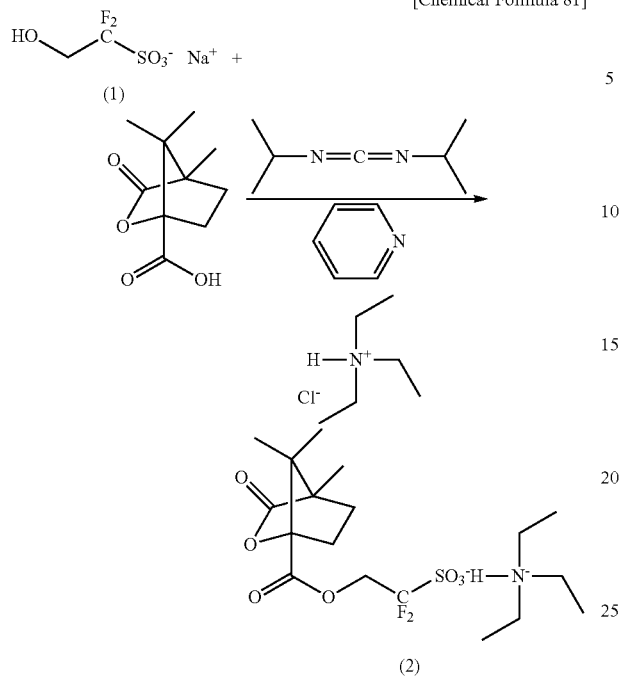

The thus obtained compound (2) was analyzed using ¹H-NMR and ¹⁹F-NMR, and the structure was identified on the basis of the following results.

¹H-NMR (400 MHz, DMSO-d6): δ (ppm)=8.82 (br s, 1H, NH), 4.84 (ddd, 1H, CH₂O), 4.68 (ddd, 1H, CH₂O), 3.13 (q, 6H, CH₂CH₃), 2.38 to 2.45 (m, 1H, camphanic), 1.93 to 2.06 (m, 2H, camphanic), 1.55 to 1.61 (m, 1H, camphanic), 1.20 (t, 9H, CH₂CH₃), 1.04 (s, 3H, CH₃), 1.03 (s, 3H, CH₃), 0.85 (s, 3H, CH₃)

¹⁹F-NMR (376 MHz, DMSO-d6): δ (ppm)=−111.0

Based on the results of the above NMR analyses, the compound (2) was confirmed as having the structure shown above.

ii) Synthesis of Compound (B1-1-1)

A round-bottom flask was charged with 4-methylphenyl-diphenylsulfonium bromide (2.1 g), the compound (2) (2.2 g), dichloromethane (31 g) and pure water (31 g), and the resulting mixture was stirred for 20 hours at room temperature. Subsequently, the dichloromethane layer was washed with 1% by weight aqueous solution of hydrochloric acid, and then washed repeatedly with pure water (31 g) until the wash water was neutral. The organic layer was then concentrated under reduced pressure, yielding the compound (B1-1-1) (3.0 g) as a white solid.

[Chemical Formula 82]

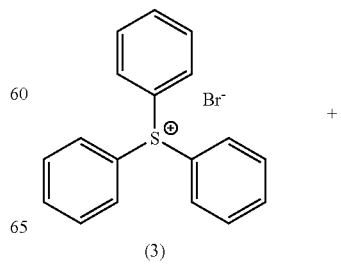

-continued

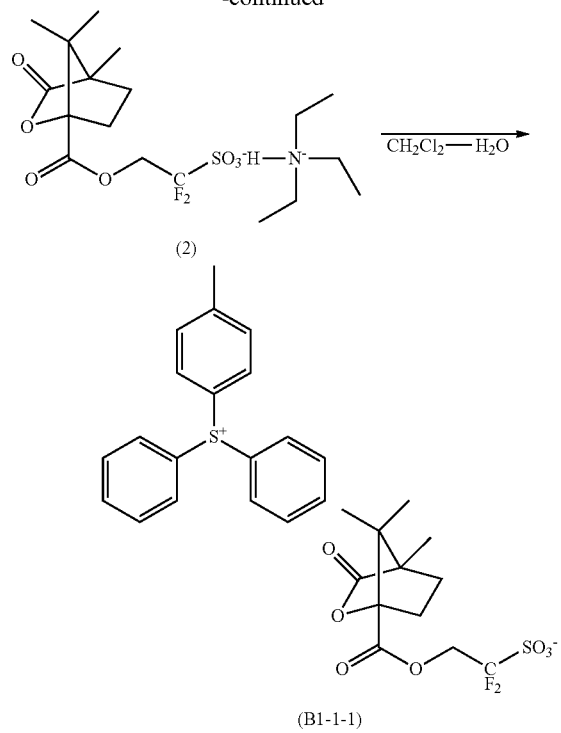

The thus obtained compound (B1-1-1) was analyzed using ¹H-NMR and ¹⁹F-NMR, and the structure was identified on the basis of the following results.

¹H-NMR (400 MHz, DMSO-d6): δ (ppm)=7.72 to 7.84 (m, 12H, ArH), 7.56 (d, 2H, ArH), 4.84 (ddd, 1H, CH₂O), 4.68 (ddd, 1H, CH₂O), 3.35 (s, 3H, CH₃), 2.38 to 2.45 (m, 1H, camphanic), 1.93 to 2.06 (m, 2H, camphanic), 1.55 to 1.61 (m, 1H, camphanic), 1.04 (s, 3H, CH₃), 1.03 (s, 3H, CH₃), 0.85 (s, 3H, CH₃)

¹⁹F-NMR (376 MHz, DMSO-d6): δ (ppm)=−111.0

Based on the results of the above NMR analyses, the compound (B1-1-1) was confirmed as having the structure shown above.

Example 2

Synthesis of Compound (B1-1-2)

With the exception of replacing the 4-methylphenyldiphenylsulfonium bromide with a compound (3), reaction was conducted in the same manner as that described for the synthesis example of ii) in Example 1, thus yielding the compound (B1-1-2).

[Chemical Formula 83]

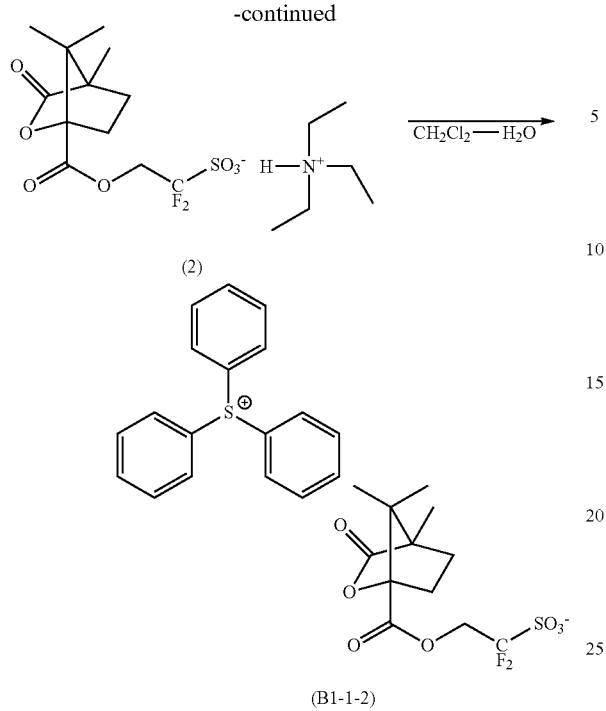

(B1-1-2)

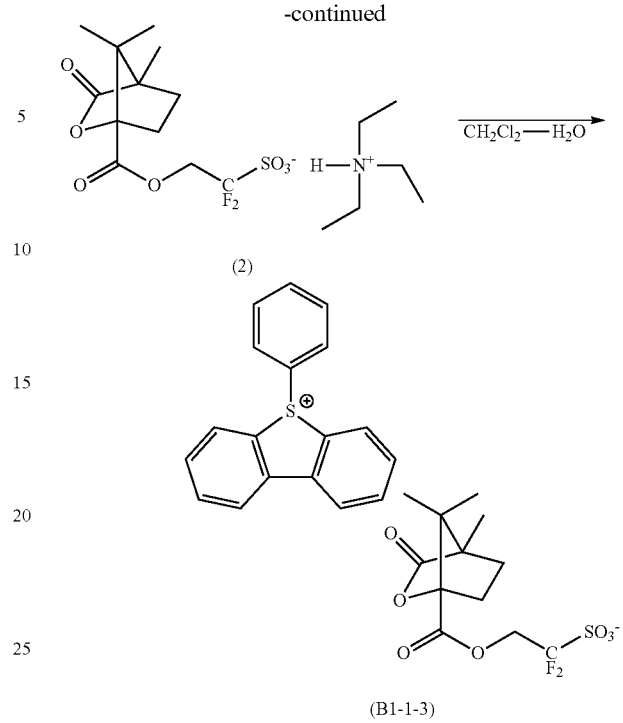

(B1-1-3)

The thus obtained compound (B1-1-2) was analyzed using $^1$H-NMR and $^{19}$F-NMR, and the structure was identified on the basis of the following results.

$^1$H-NMR (400 MHz, DMSO-d6): δ (ppm)=7.74 to 7.90 (m, 15H, phenyl), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-2) was confirmed as having the structure shown above.

Example 3

Synthesis of Compound (B1-1-3)

With the exception of replacing the 4-methylphenyldiphenylsulfonium bromide with a compound (4), reaction was conducted in the same manner as that described for the synthesis example of ii) in Example 1, thus yielding the compound (B1-1-3).

[Chemical Formula 84]

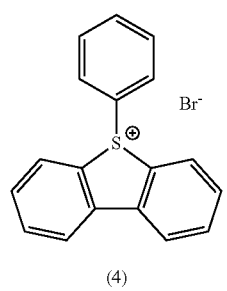

(4)

+

The thus obtained compound (B1-1-3) was analyzed using $^1$H-NMR and $^{19}$F-NMR, and the structure was identified on the basis of the following results.

$^1$H-NMR (400 MHz, DMSO-d6): δ (ppm)=8.50 (d, 2H, ArH), 8.37 (d, 2H, ArH), 7.93 (t, 2H, ArH), 7.55 to 7.75 (m, 7H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-3) was confirmed as having the structure shown above.

Example 4

Synthesis of Compound (B1-1-4)

With the exception of replacing the 4-methylphenyldiphenylsulfonium bromide with a compound (5), reaction was conducted in the same manner as that described for the synthesis example of ii) in Example 1, thus yielding the compound (B1-1-4).

[Chemical Formula 85]

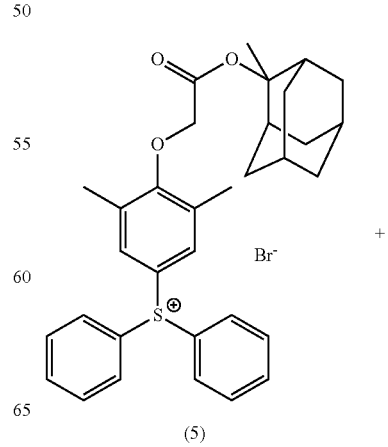

(5)

-continued

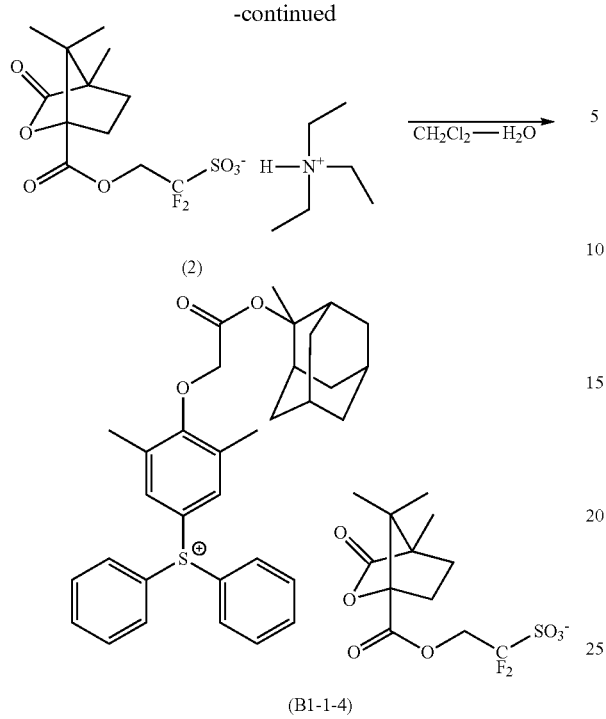

(B1-1-4)

The thus obtained compound (B1-1-4) was analyzed using $^1$H-NMR and $^{19}$F-NMR, and the structure was identified on the basis of the following results.

$^1$H-NMR (400 MHz, DMSO-d6): δ (ppm)=7.75 to 7.86 (m, 10H, ArH), 7.61 (s, 2H, ArH), 4.84 (ddd, 1H, CH$_2$O), 4.68 (ddd, 1H, CH$_2$O), 4.62 (s, 2H, CH$_2$), 2.38 to 2.45 (m, 1H, camphanic), 2.31 (s, 6H, CH$_3$), 1.49 to 2.06 (m, 20H, adamantane+camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-4) was confirmed as having the structure shown above.

Example 5

Synthesis of Compound (B1-1-5)

With the exception of replacing the 4-methylphenyldiphenylsulfonium bromide with a compound (6), reaction was conducted in the same manner as that described for the synthesis example of ii) in Example 1, thus yielding the compound (B1-1-5).

[Chemical Formula 86]

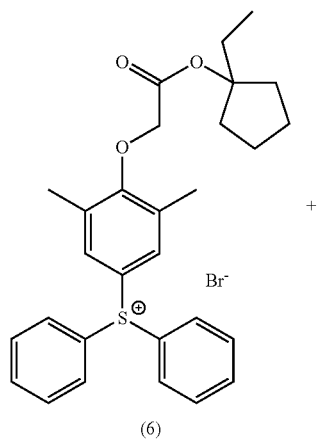

(6)

-continued

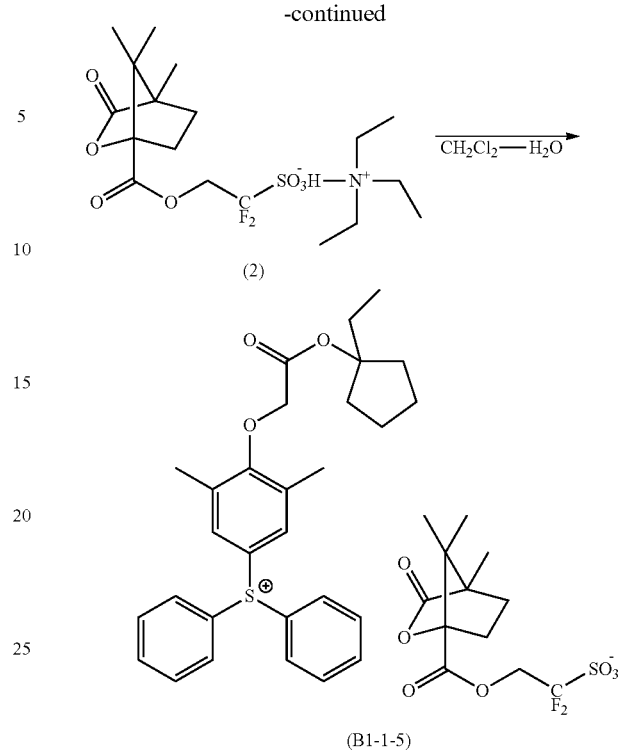

(B1-1-5)

The thus obtained compound (B1-1-5) was analyzed using $^1$H-NMR and $^{19}$F-NMR, and the structure was identified on the basis of the following results.

$^1$H-NMR (400 MHz, DMSO-d6): δ (ppm)=7.76 to 7.82 (m, 10H, ArH), 7.59 (s, 2H, ArH), 4.84 (ddd, 1H, CH$_2$O), 4.68 (ddd, 1H, CH$_2$O), 4.55 (s, 2H, CH$_2$), 2.38 to 2.45 (m, 1H, camphanic), 2.29 (m, 6H, CH$_3$), 1.90 to 2.06 (m, 6H, CH$_2$+cyclopentyl+camphanic), 1.48 to 1.75 (m, 17H, cyclopentyl+camphanic), 1.04 (s, 3H, CH$_3$), 1.03 (s, 3H, CH$_3$), 0.85 (s, 3H, CH$_3$), 0.77 to 0.81 (t, 3H, CH$_3$)

$^{19}$F-NMR (376 MHz, DMSO-d6): δ (ppm)=−111.0

Based on the results of the above NMR analyses, the compound (B1-1-5) was confirmed as having the structure shown above.

Example 6

Synthesis of Compound (B1-1-6)

With the exception of replacing the 4-methylphenyldiphenylsulfonium bromide with a compound (7), reaction was conducted in the same manner as that described for the synthesis example of ii) in Example 1, thus yielding the compound (B1-1-6).

[Chemical Formula 87]

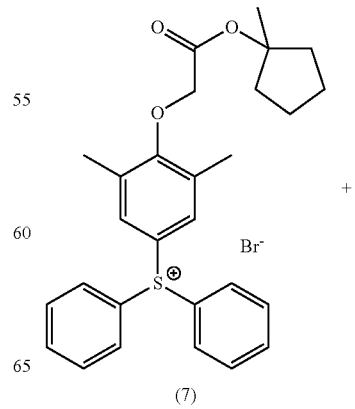

(7)

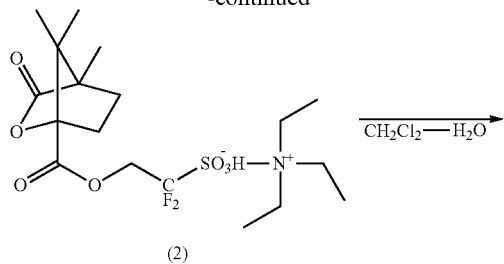

(2)

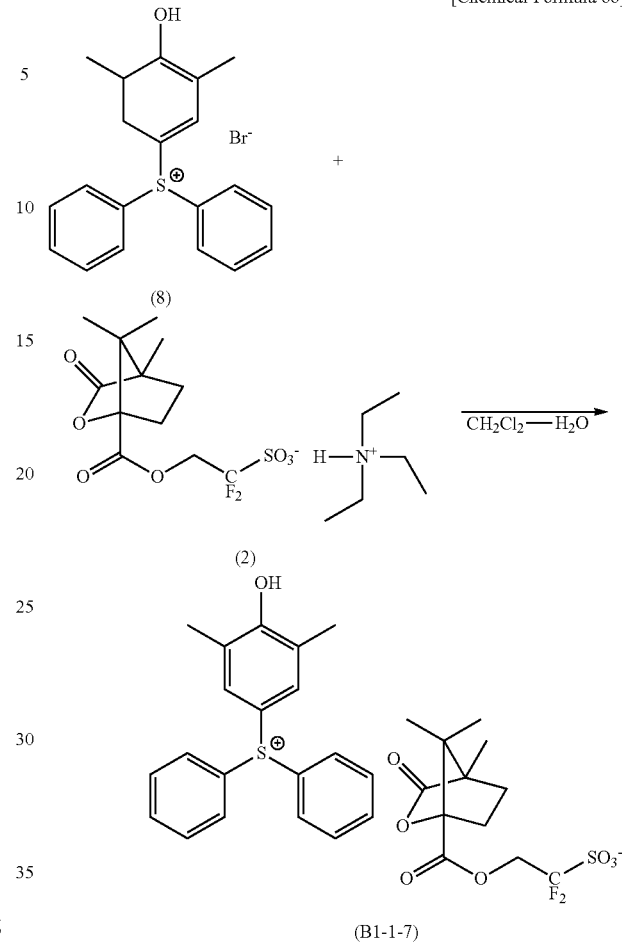

(B1-1-6)

The thus obtained compound (B1-1-6) was analyzed using ¹H-NMR and ¹⁹F-NMR, and the structure was identified on the basis of the following results.

¹H-NMR (400 MHz, DMSO-d6): δ (ppm)=7.76 to 7.82 (m, 10H, ArH), 7.59 (s, 2H, ArH), 4.84 (ddd, 1H, $CH_2O$), 4.68 (ddd, 1H, $CH_2O$), 4.55 (s, 2H, $CH_2$), 2.38 to 2.45 (m, 1H, camphanic), 2.29 (m, 6H, $CH_3$), 1.90 to 2.08 (m, 4H, cyclopentyl+camphanic), 1.48 to 1.75 (m, 10H, $CH_3$+cyclopentyl+camphanic), 1.04 (s, 3H, $CH_3$), 1.03 (s, 3H, $CH_3$), 0.85 (s, 3H, $CH_3$)

¹⁹F-NMR (376 MHz, DMSO-d6): δ (ppm)=−111.0

Based on the results of the above NMR analyses, the compound (B1-1-6) was confirmed as having the structure shown above.

Example 7

Synthesis of Compound (B1-1-7)

With the exception of replacing the 4-methylphenyldiphenylsulfonium bromide with a compound (8), reaction was conducted in the same manner as that described for the synthesis example of ii) in Example 1, thus yielding the compound (B1-1-7).

[Chemical Formula 88]

The thus obtained compound (B1-1-7) was analyzed using ¹H-NMR and ¹⁹F-NMR, and the structure was identified on the basis of the following results.

¹H-NMR (400 MHz, DMSO-d6): δ (ppm)=10.05 (s, 1H, OH), 7.64 to 7.87 (m, 10H, ArH), 7.56 (s, 2H, ArH), 4.84 (ddd, 1H, $CH_2O$), 4.68 (ddd, 1H, $CH_2O$), 2.38 to 2.45 (m, 1H, camphanic), 2.22 (m, 6H, $CH_3$), 1.93 to 2.06 (m, 2H, camphanic), 1.55 to 1.61 (m, 1H, camphanic), 1.04 (s, 3H, $CH_3$), 1.03 (s, 3H, $CH_3$), 0.85 (s, 3H, $CH_3$)

¹⁹F-NMR (376 MHz, DMSO-d6): δ (ppm)=−111.0

Based on the results of the above NMR analyses, the compound (B1-1-7) was confirmed as having the structure shown above.

Example 8

Synthesis of Compound (B1-1-8)

With the exception of replacing the 4-methylphenyldiphenylsulfonium bromide with a compound (9), reaction was conducted in the same manner as that described for the synthesis example of ii) in Example 1, thus yielding the compound (B1-1-8).

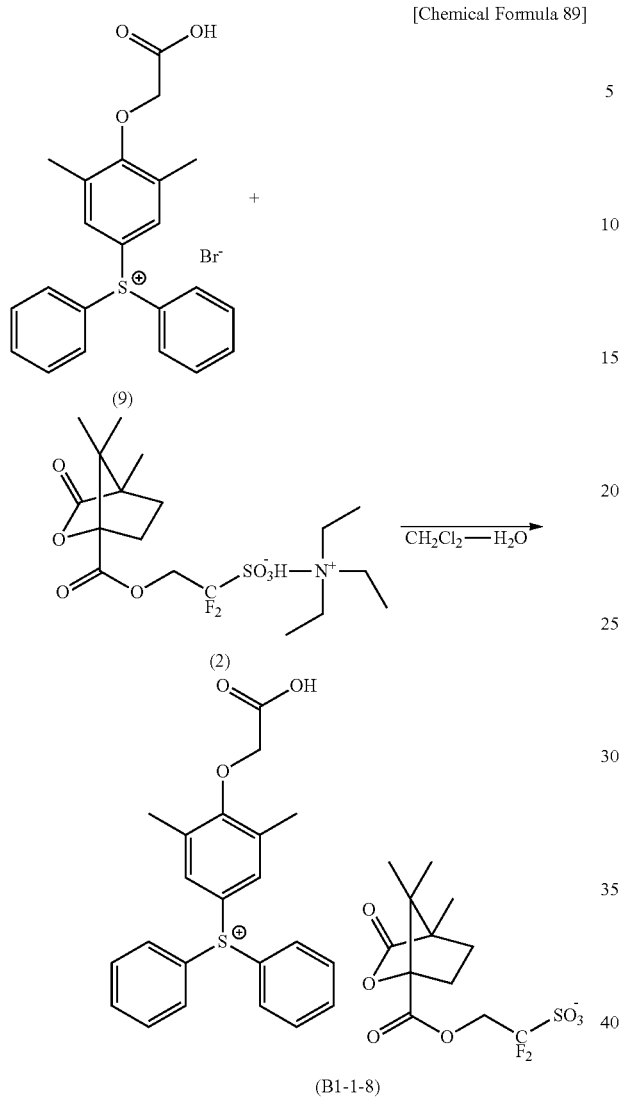

(B1-1-8)

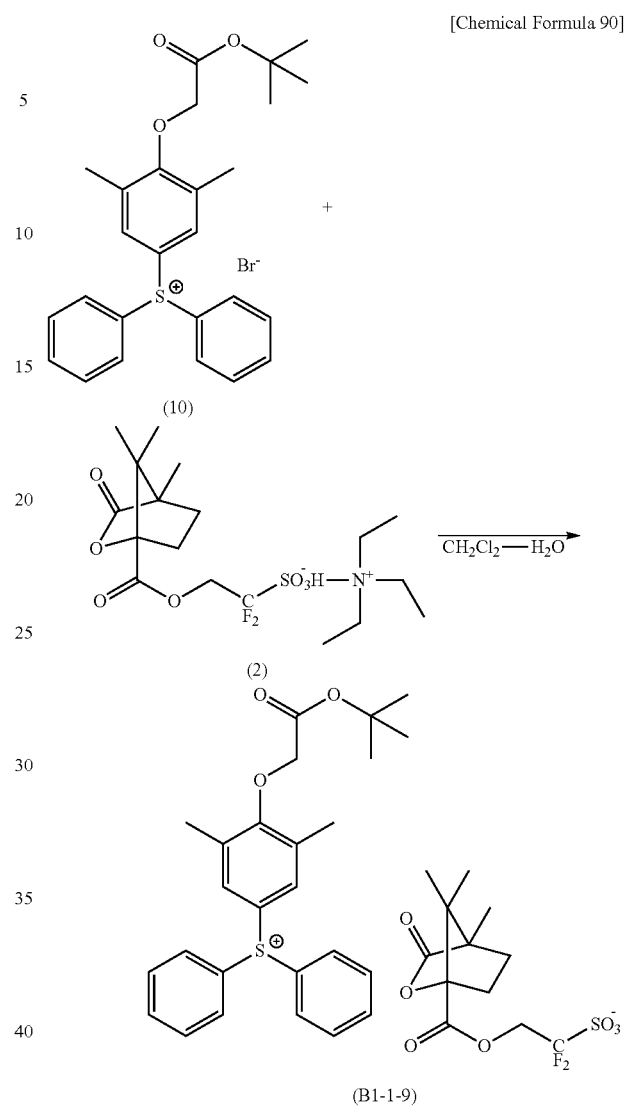

(B1-1-9)

The thus obtained compound (B1-1-8) was analyzed using $^1$H-NMR and $^{19}$F-NMR, and the structure was identified on the basis of the following results.

$^1$H-NMR (400 MHz, DMSO-d6): δ (ppm)=7.71 to 7.89 (m, 10H, ArH), 7.59 (s, 2H, ArH), 4.84 (ddd, 1H, CH$_2$O), 4.68 (ddd, 1H, CH$_2$O), 4.53 (s, 2H, CH$_2$), 2.38 to 2.45 (m, 1H, camphanic), 2.30 (d, 6H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-8) was confirmed as having the structure shown above.

Example 9

Synthesis of Compound (B1-1-9)

With the exception of replacing the 4-methylphenyldiphenylsulfonium bromide with a compound (10), reaction was conducted in the same manner as that described for the synthesis example of ii) in Example 1, thus yielding the compound (B1-1-9).

The thus obtained compound (B1-1-9) was analyzed using $^1$H-NMR and $^{19}$F-NMR, and the structure was identified on the basis of the following results.

$^1$H-NMR (400 MHz, DMSO-d6): δ (ppm)=7.75 to 7.86 (m, 10H, ArH), 7.63 (s, 2H, ArH), 4.84 (ddd, 1H, CH$_2$O), 4.68 (ddd, 1H, CH$_2$O), 4.55 (s, 2H, CO—CH$_2$), 2.38 to 2.45 (m, 1H, camphanic), 2.30 (s, 6H, ArCH$_3$), 1.93 to 2.06 (m, 2H, camphanic), 1.55 to 1.61 (m, 1H, camphanic), 1.43 (s, 9H, t-butyl), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-9) was confirmed as having the structure shown above.

Example 10

Synthesis of Compound (B1-1-10)

With the exception of replacing the 4-methylphenyldiphenylsulfonium bromide with a compound (11), reaction was conducted in the same manner as that described for the synthesis example of ii) in Example 1, thus yielding the compound (B1-1-10).

[Chemical Formula 91]

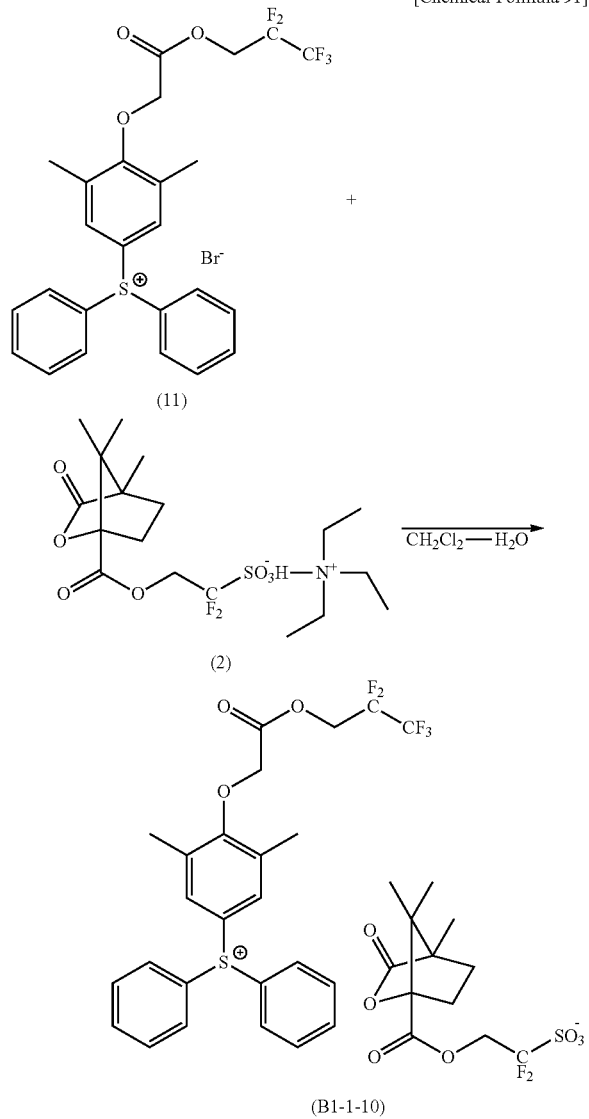

(B1-1-10)

The thus obtained compound (B1-1-10) was analyzed using $^1$H-NMR and $^{19}$F-NMR, and the structure was identified on the basis of the following results.

$^1$H-NMR (400 MHz, DMSO-d6): δ (ppm)=7.75 to 7.87 (m, 10H, ArH), 7.63 (s, 2H, ArH), 4.94 (t, 2H, OCH$_2$CF$_2$), 4.84 (m, 3H, CH$_2$O), 4.68 (ddd, 1H, CH$_2$O), 2.38 to 2.45 (m, 1H, camphanic), 2.37 (s, 6H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−80.4, −111.0, −119.7

Based on the results of the above NMR analyses, the compound (B1-1-10) was confirmed as having the structure shown above.

Example 11

Synthesis of Compound (B1-1-11)

With the exception of replacing the 4-methylphenyldiphenylsulfonium bromide with a compound (12), reaction was conducted in the same manner as that described for the synthesis example of ii) in Example 1, thus yielding the compound (B1-1-11).

[Chemical Formula 92]

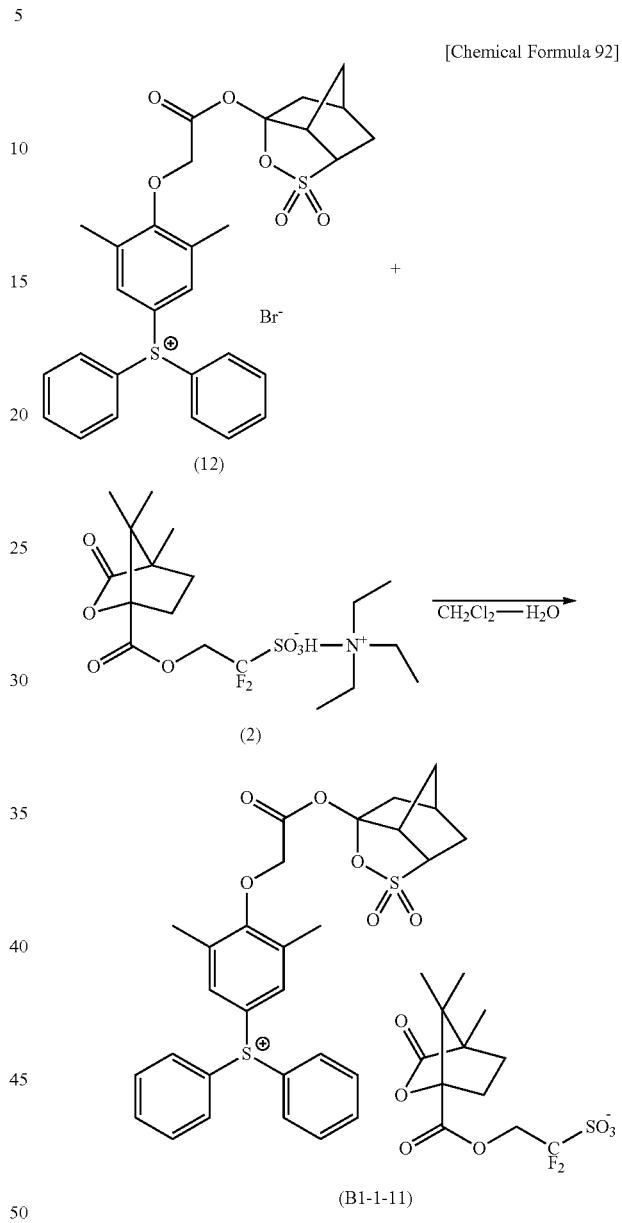

(B1-1-11)

The thus obtained compound (B1-1-11) was analyzed using $^1$H-NMR and $^{19}$F-NMR, and the structure was identified on the basis of the following results.

$^1$H-NMR (400 MHz, DMSO-d6): δ (ppm)=7.72 to 7.83 (m, 10H, ArH), 7.59 (s, 2H, ArH), 4.90 (m, 1H, sultone), 4.84 (ddd, 1H, CH$_2$O), 4.68 (ddd, 1H, CH$_2$O), 4.62 to 4.67 (m, 3H, CH$_2$O+sultone), 3.83 to 3.89 (m, 1H, sultone), 3.43 (m, 1H, sultone), 1.75 to 2.49 (m, 14H, camphanic+sultone+Ar—CH$_3$), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-11) was confirmed as having the structure shown above.

Example 12

Synthesis of Compound (B1-1-12)

With the exception of replacing the 4-methylphenyldiphenylsulfonium bromide with a compound (13), reaction was conducted in the same manner as that described for the synthesis example of ii) in Example 1, thus yielding the compound (B1-1-12).

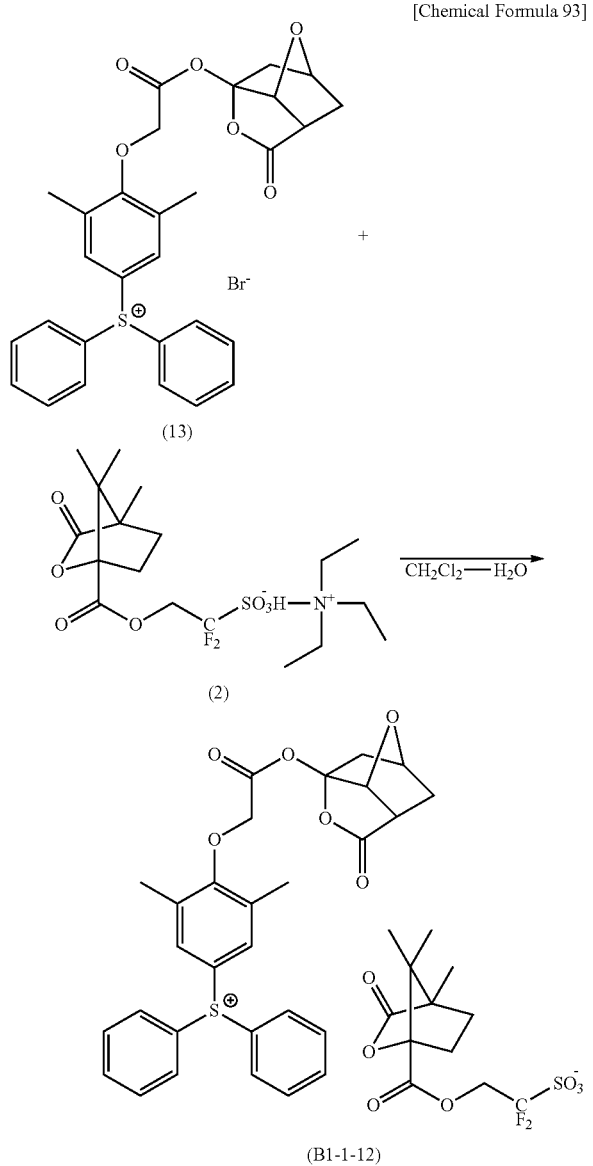

[Chemical Formula 93]

The thus obtained compound (B1-1-12) was analyzed using $^1$H-NMR and $^{19}$F-NMR, and the structure was identified on the basis of the following results.

$^1$H-NMR (400 MHz, DMSO-d6): δ (ppm)=7.74 to 7.84 (m, 10H, ArH), 7.61 (s, 2H, ArH), 5.42 (t, 1H, oxo-norbornane), 4.97 (s, 1H, oxo-norbornane), 4.84 (ddd, 1H, CH$_2$O), 4.67 to 4.71 (m, 5H, CH$_2$O+CH$_2$+oxo-norbornane), 2.69 to 2.73 (m, 1H, oxo-norbornane), 2.38 to 2.45 (m, 1H, camphanic), 2.32 (s, 6H, Ar—CH$_3$), 2.06 to 2.17 (m, 2H, oxo-norbornane), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-12) was confirmed as having the structure shown above.

Example 13

Synthesis of Compound (B1-1-13)

With the exception of replacing the 4-methylphenyldiphenylsulfonium bromide with a compound (14), reaction was conducted in the same manner as that described for the synthesis example of ii) in Example 1, thus yielding the compound (B1-1-13).

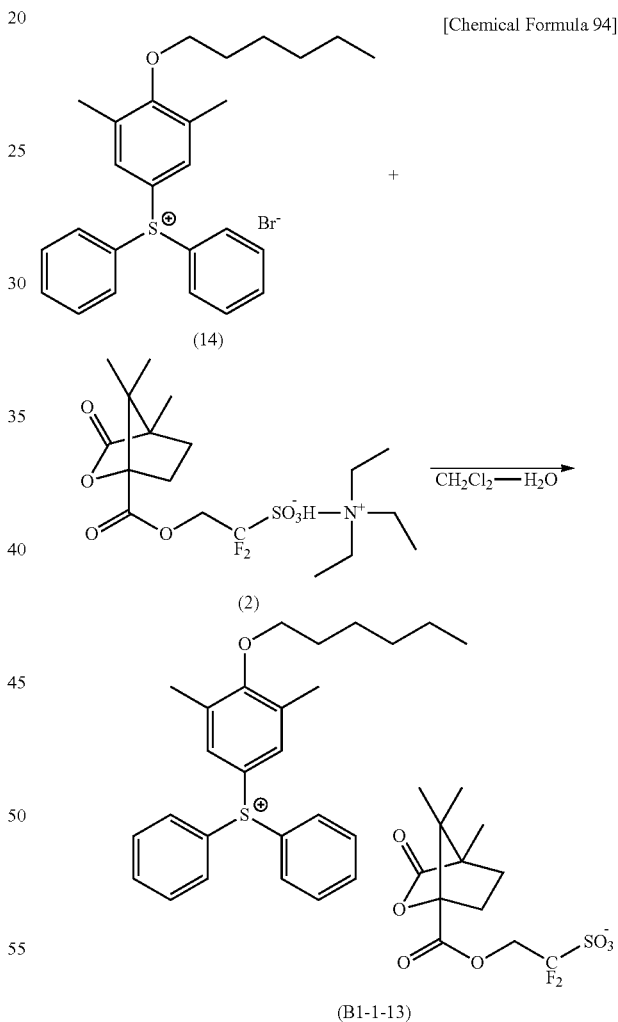

[Chemical Formula 94]

The thus obtained compound (B1-1-13) was analyzed using $^1$H-NMR and $^{19}$F-NMR, and the structure was identified on the basis of the following results.

$^1$H-NMR (400 MHz, DMSO-d6): δ (ppm)=7.73 to 7.85 (m, 10H, ArH), 7.59 (s, 2H, ArH), 4.84 (ddd, 1H, CH$_2$O), 4.68 (ddd, 1H, CH$_2$O), 3.83 (t, 2H, OCH$_2$), 2.38 to 2.45 (m, 1H, camphanic), 2.33 (s, 6H, CH$_3$), 1.93 to 2.06 (m, 2H, camphanic), 1.55 to 1.61 (m, 1H, camphanic), 1.45 (m, 4H, CH$_2$), 1.29 (m, 4H, CH$_2$), 1.04 (s, 3H, CH$_3$), 1.03 (s, 3H, CH$_3$), 0.87 (t, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-13) was confirmed as having the structure shown above.

Example 14

Synthesis of Compound (B1-1-14)

With the exception of replacing the 4-methylphenyldiphenylsulfonium bromide with a compound (15), reaction was conducted in the same manner as that described for the synthesis example of ii) in Example 1, thus yielding the compound (B1-1-14).

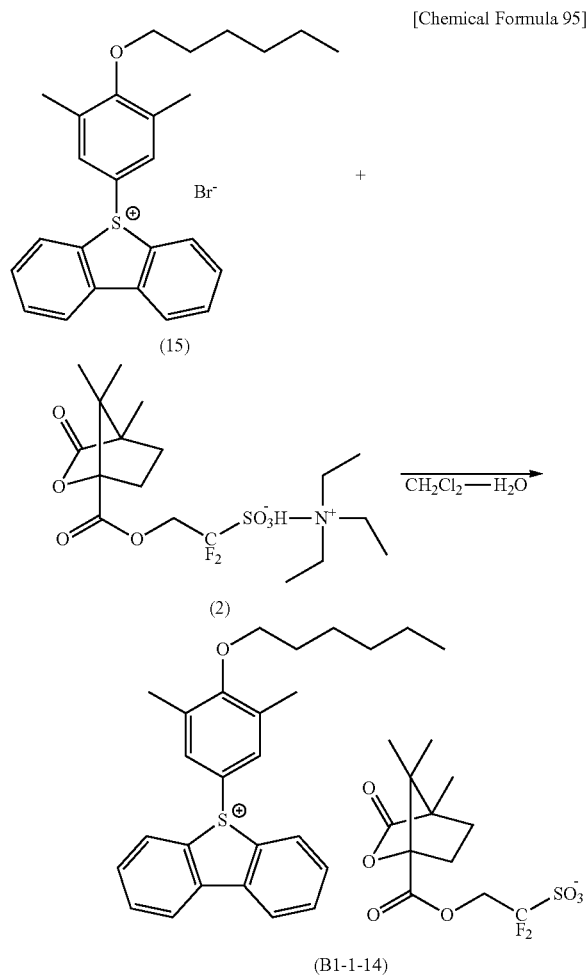

The thus obtained compound (B1-1-14) was analyzed using $^1$H-NMR and $^{19}$F-NMR, and the structure was identified on the basis of the following results.

$^1$H-NMR (400 MHz, DMSO-d6): δ (ppm)=8.53 (d, 2H, ArH), 8.27 (d, 2H, ArH), 7.95 (t, 2H, ArH), 7.74 (t, 2H, ArH), 7.20 (s, 1H, ArH), 6.38 (s, 1H, ArH), 4.84 (ddd, 1H, CH$_2$O), 4.68 (ddd, 1H, CH$_2$O), 4.05 (t, 2H, cation-OCH$_2$), 2.86 (s, 3H, ArCH$_3$), 2.38 to 2.45 (m, 1H, camphanic), 1.93 to 2.06 (m, 2H, camphanic), 1.84 (s, 3H, ArCH$_3$), 1.69 (quin, 2H, CH$_2$), 1.55 to 1.61 (m, 1H, camphanic), 1.37 (quin, 2H, CH$_2$), 1.24 to 1.26 (m, 4H, CH$_2$), 1.04 (s, 3H, CH$_3$), 1.03 (s, 3H, CH$_3$), 0.85 (s, 3H, CH$_3$), 0.82 (t, 3H, CH$_3$)

$^{19}$F-NMR (376 MHz, DMSO-d6): δ (ppm)=−111.0

Based on the results of the above NMR analyses, the compound (B1-1-14) was confirmed as having the structure shown above.

Example 15

Synthesis of Compound (B1-1-15)

With the exception of replacing the 4-methylphenyldiphenylsulfonium bromide with a compound (16), reaction was conducted in the same manner as that described for the synthesis example of ii) in Example 1, thus yielding the compound (B1-1-15).

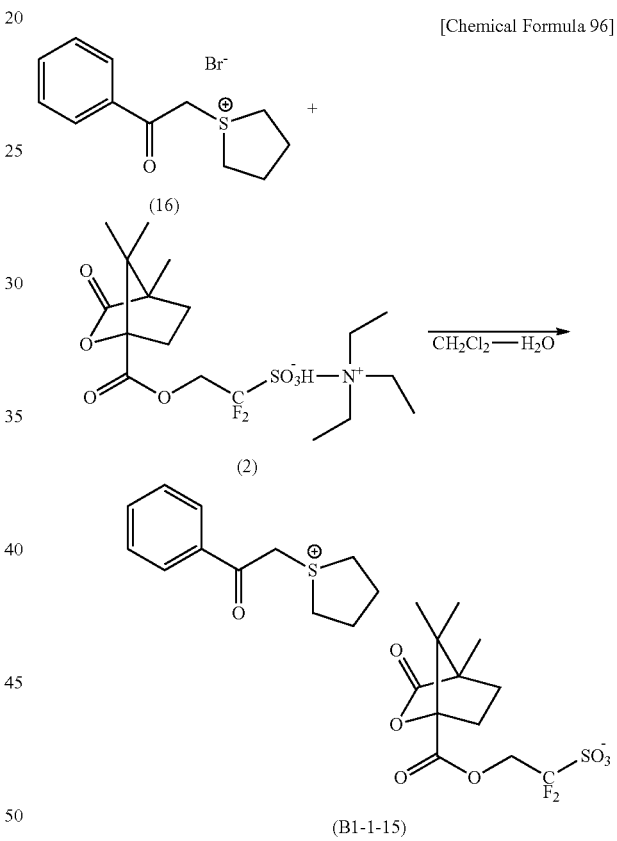

The thus obtained compound (B1-1-15) was analyzed using $^1$H-NMR and $^{19}$F-NMR, and the structure was identified on the basis of the following results.

$^1$H-NMR (400 MHz, DMSO-d6): δ (ppm)=7.99 to 8.01 (d, 2H, Ar), 7.73 to 7.76 (t, 1H, Ar), 7.58 to 7.61 (t, 2H, Ar), 5.31 (s, 2H, SCH$_2$C=O), 4.84 (ddd, 1H, CH$_2$O), 4.68 (ddd, 1H, CH$_2$O), 3.49 to 3.62 (m, 4H, CH$_2$), 2.18 to 2.49 (m, 5H, CH$_2$S+camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-15) was confirmed as having the structure shown above.

Example 16

Synthesis of Compound (B1-1-16)

With the exception of replacing the 4-methylphenyldiphenylsulfonium bromide with a compound (17), reaction was conducted in the same manner as that described for the synthesis example of ii) in Example 1, thus yielding the compound (B1-1-16).

[Chemical Formula 97]

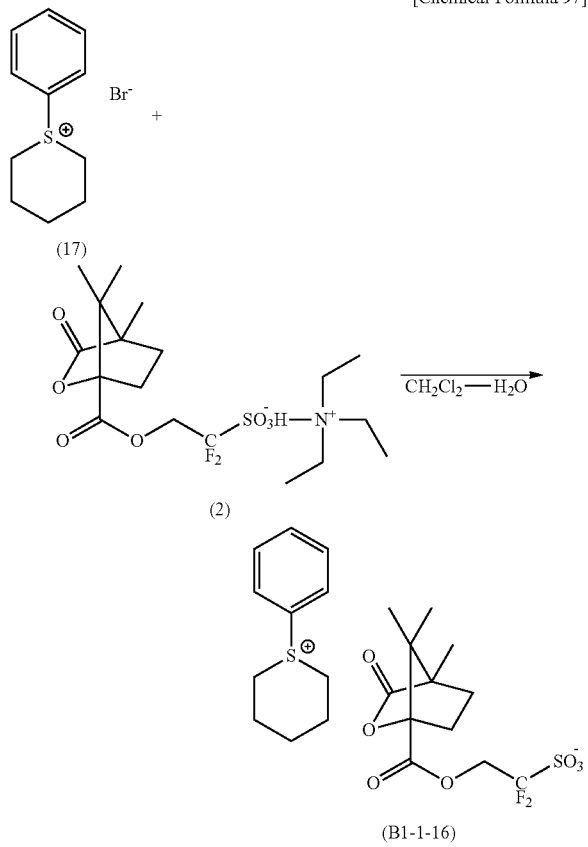

The thus obtained compound (B1-1-16) was analyzed using $^1$H-NMR and $^{19}$F-NMR, and the structure was identified on the basis of the following results.

$^1$H-NMR (400 MHz, DMSO-d6): δ (ppm)=8.02 to 8.05 (m, 2H, phenyl), 7.61 to 7.73 (m, 3H, phenyl), 4.84 (ddd, 1H, CH$_2$O), 4.68 (ddd, 1H, CH$_2$O), 3.76 to 3.86 (m, 4H, SCH$_2$), 2.38 to 2.45 (m, 1H, camphanic), 2.09 to 2.12 (m, 2H, CH$_2$), 1.93 to 2.06 (m, 2H, camphanic), 1.84 to 1.92 (m, 2H, CH$_2$), 1.62 to 1.70 (m, 2H, CH$_2$), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-16) was confirmed as having the structure shown above.

Example 17

Synthesis of Compound (B1-1-17)

With the exception of replacing the 4-methylphenyldiphenylsulfonium bromide with a compound (18), reaction was conducted in the same manner as that described for the synthesis example of ii) in Example 1, thus yielding the compound (B1-1-17).

[Chemical Formula 98]

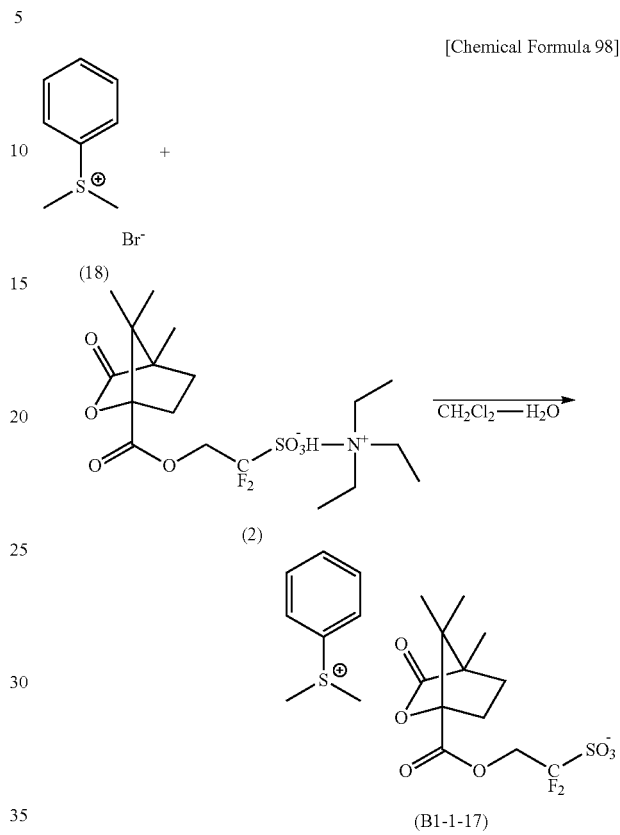

The thus obtained compound (B1-1-17) was analyzed using $^1$H-NMR and $^{19}$F-NMR, and the structure was identified on the basis of the following results.

$^1$H-NMR (400 MHz, DMSO-d6): δ (ppm)=8.04 to 8.09 (m, 2H, phenyl), 7.69 to 7.79 (m, 3H, phenyl), 4.84 (ddd, 1H, CH$_2$O), 4.68 (ddd, 1H, CH$_2$O), 3.29 (s, 6H, CH$_3$), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-17) was confirmed as having the structure shown above.

Example 18

Synthesis of Compound (B1-1-18

With the exception of replacing the 4-methylphenyldiphenylsulfonium bromide with a compound (19), reaction was conducted in the same manner as that described for the synthesis example of ii) in Example 1, thus yielding the compound (B1-1-18).

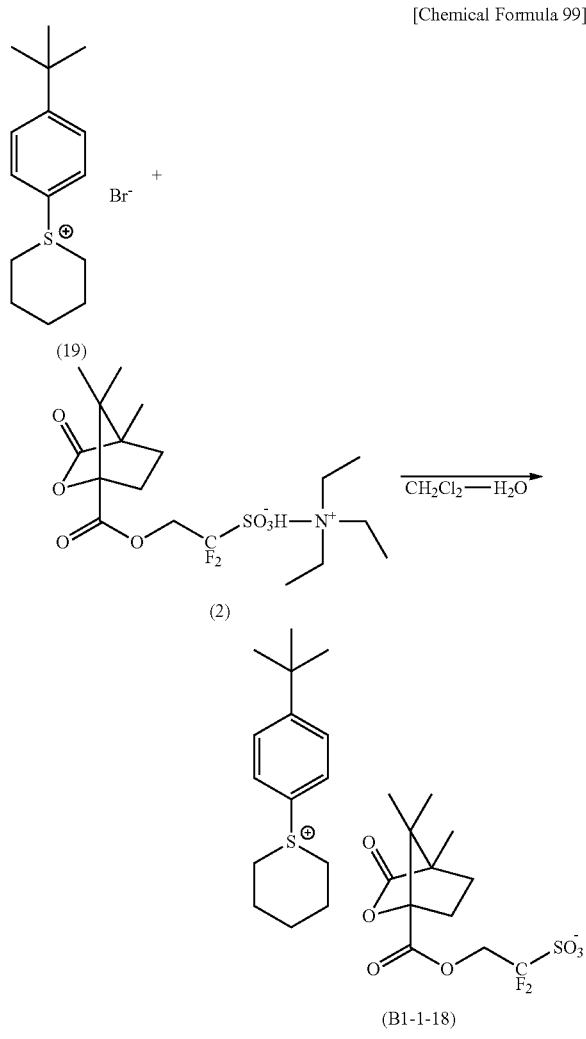

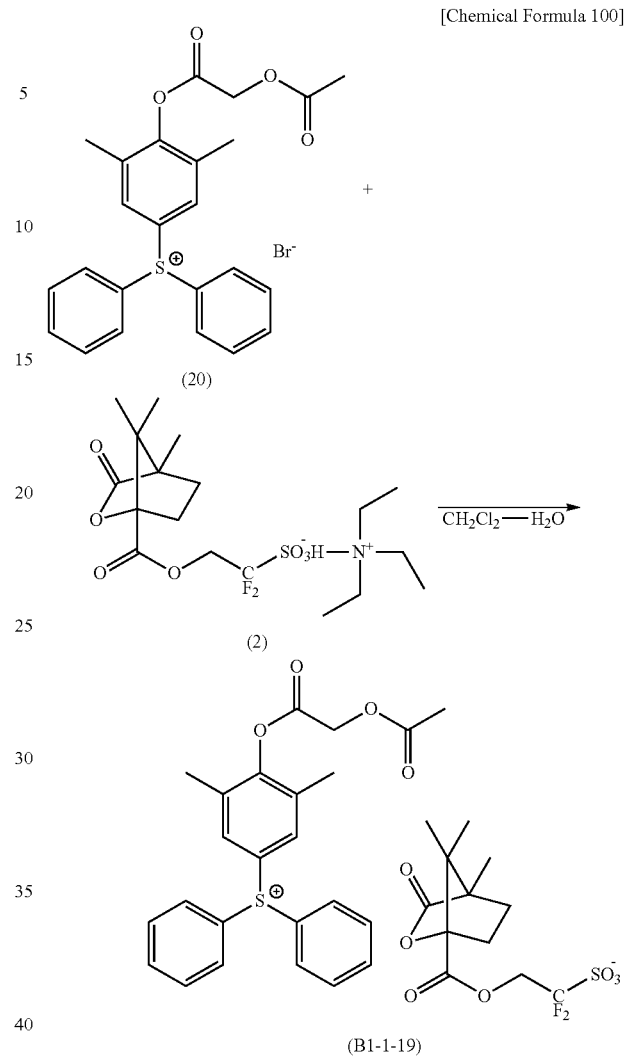

The thus obtained compound (B1-1-18) was analyzed using $^{1}$H-NMR and $^{19}$F-NMR, and the structure was identified on the basis of the following results.

$^{1}$H-NMR (400 MHz, DMSO-d6): δ (ppm)=8.07 (d, 2H, phenyl), 7.81 (d, 2H, phenyl), 4.84 (ddd, 1H, CH$_2$O), 4.68 (ddd, 1H, CH$_2$O), 4.10 (t, 2H, CH$_3$), 3.59 (d, 2H, CH$_2$), 2.38 to 2.45 (m, 1H, camphanic), 2.20 (d, 2H, CH$_2$), 1.71 to 2.19 (m, 6H, CH$_2$+camphanic), 1.55 to 1.61 (m, 1H, camphanic), 1.23 (s, 9H, t-Bu), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-18) was confirmed as having the structure shown above.

Example 19

Synthesis of Compound (B1-1-19)

With the exception of replacing the 4-methylphenyldiphenylsulfonium bromide with a compound (20), reaction was conducted in the same manner as that described for the synthesis example of ii) in Example 1, thus yielding the compound (B1-1-19).

The thus obtained compound (B1-1-19) was analyzed using $^{1}$H-NMR and $^{19}$F-NMR, and the structure was identified on the basis of the following results.

$^{1}$H-NMR (400 MHz, DMSO-d6): δ (ppm)=7.77 to 7.89 (m, 10H, ArH), 7.70 (s, 2H, ArH), 5.10 (s, 2H, OCOCH$_2$O), 4.84 (ddd, 1H, CH$_2$O), 4.68 (ddd, 1H, CH$_2$O), 2.38 to 2.45 (m, 1H, camphanic), 2.07 to 2.19 (m, 9H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-19) was confirmed as having the structure shown above.

Example 20

Synthesis of Compound (B1-1-20)

With the exception of replacing the 4-methylphenyldiphenylsulfonium bromide with a compound (21), reaction was conducted in the same manner as that described for the synthesis example of ii) in Example 1, thus yielding the compound (B1-1-20).

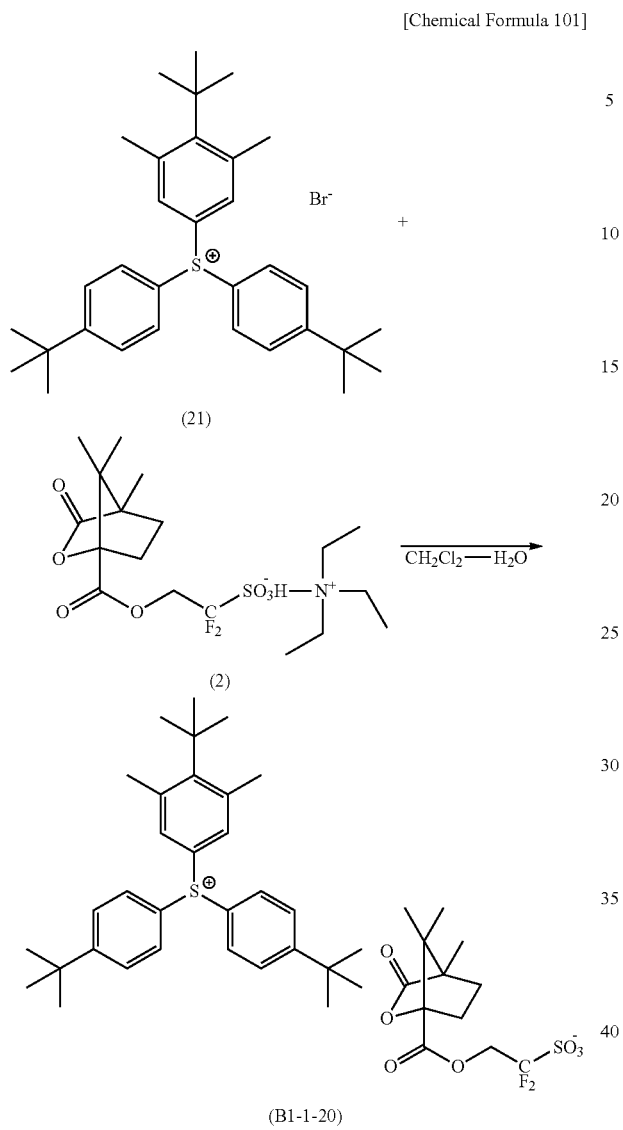

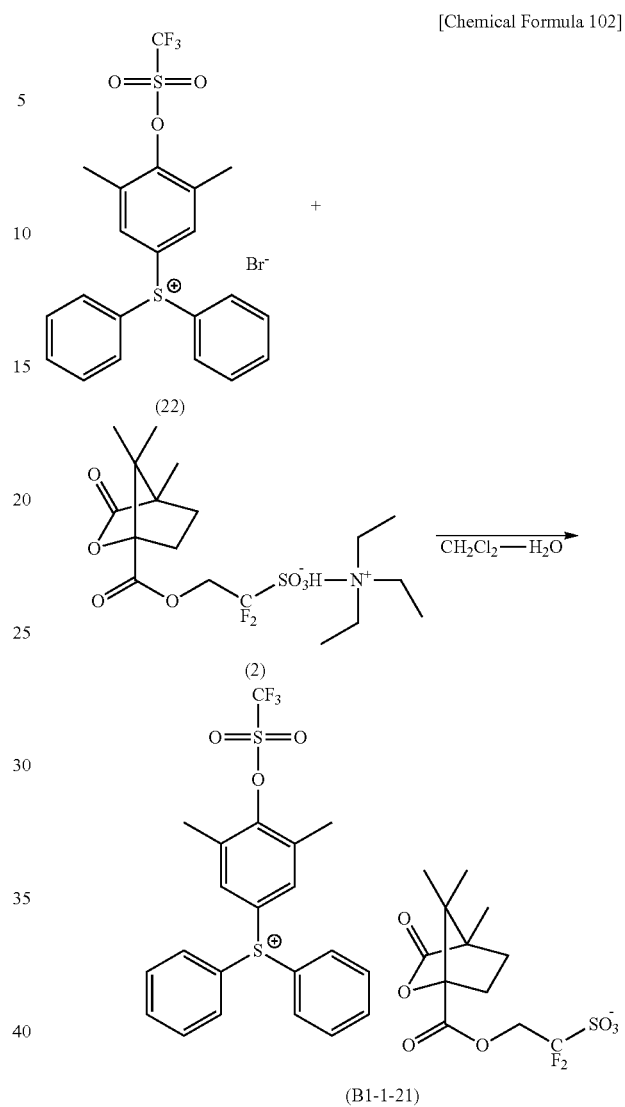

The thus obtained compound (B1-1-20) was analyzed using ¹H-NMR and ¹⁹F-NMR, and the structure was identified on the basis of the following results.

¹H-NMR (400 MHz, DMSO-d6): δ (ppm)=7.84 (d, 6H, ArH), 7.78 (d, 6H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.33 (s, 27H, tBu-CH$_3$), 1.04 (s, 3H, CH$_3$), 1.03 (s, 3H, CH$_3$), 0.85 (s, 3H, CH$_3$)

¹⁹F-NMR (376 MHz, DMSO-d6): δ (ppm)=−111.0

Based on the results of the above NMR analyses, the compound (B1-1-20) was confirmed as having the structure shown above.

Example 21

Synthesis of Compound (B1-1-21)

With the exception of replacing the 4-methylphenyldiphenylsulfonium bromide with a compound (22), reaction was conducted in the same manner as that described for the synthesis example of ii) in Example 1, thus yielding the compound (B1-1-21).

The thus obtained compound (B1-1-21) was analyzed using ¹H-NMR and ¹⁹F-NMR, and the structure was identified on the basis of the following results.

¹H-NMR (400 MHz, DMSO-d6): δ (ppm)=7.73 to 7.89 (m, 12H, ArH), 4.84 (ddd, 1H, CH$_2$O), 4.68 (ddd, 1H, CH$_2$O), 2.38 to 2.45 (m, 1H, camphanic), 2.36 (s, 6H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

¹⁹F-NMR (376 MHz, DMSO-d6): δ (ppm)=−70.2, −111.0

Based on the results of the above NMR analyses, the compound (B1-1-21) was confirmed as having the structure shown above.

Example 22

Synthesis of Compound (B1-1-22)

With the exception of replacing the 4-methylphenyldiphenylsulfonium bromide with a compound (23), reaction was conducted in the same manner as that described for the synthesis example of ii) in Example 1, thus yielding the compound (B1-1-22).

[Chemical Formula 103]

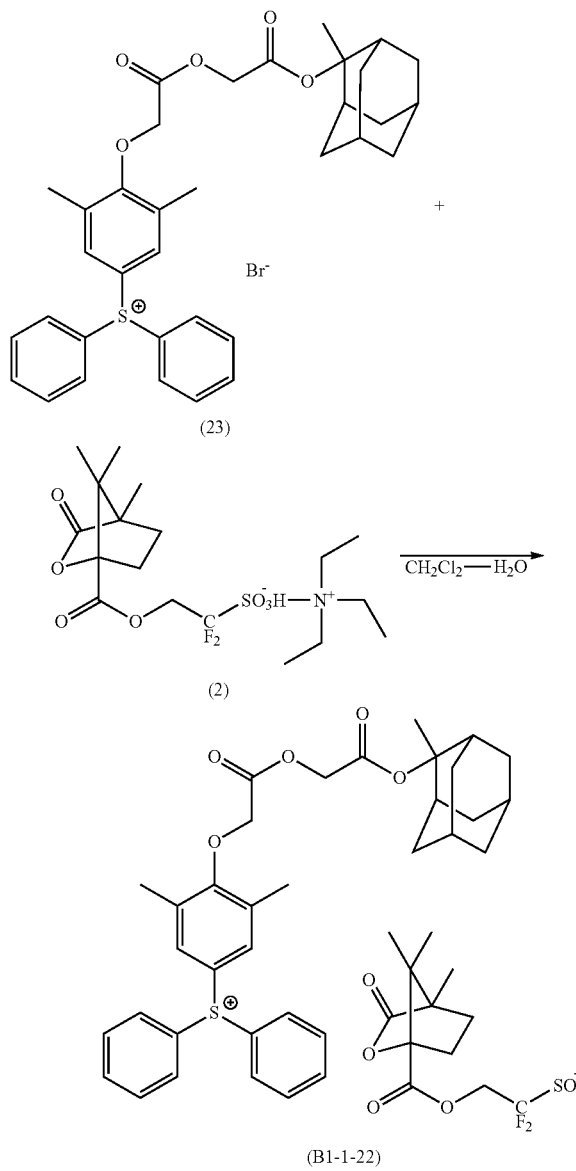

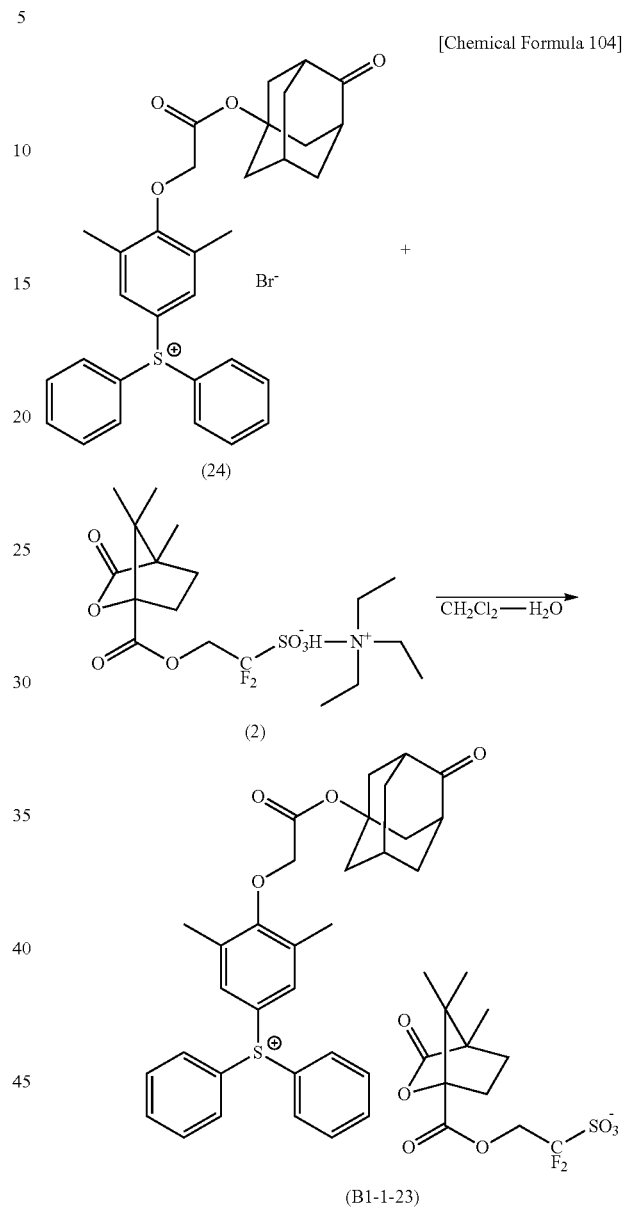

The thus obtained compound (B1-1-22) was analyzed using ¹H-NMR and ¹⁹F-NMR, and the structure was identified on the basis of the following results.

¹H-NMR (400 MHz, DMSO-d6): δ (ppm)=7.69 to 7.85 (m, 10H, ArH), 7.56 (s, 2H, ArH), 4.84 (ddd, 1H, CH$_2$O), 4.75 (s, 4H, CH$_2$), 4.68 (ddd, 1H, CH$_2$O), 2.38 to 2.45 (m, 1H, camphanic), 2.31 (s, 6H, ArCH$_3$), 2.19 (m, 2H, adamantane), 1.47 to 2.06 (m, 18H, camphanic+adamantane), 1.04 (s, 3H, CH$_3$), 1.03 (s, 3H, CH$_3$), 0.85 (s, 3H, CH$_3$)

¹⁹F-NMR (376 MHz, DMSO-d6): δ (ppm)=−111.0

Based on the results of the above NMR analyses, the compound (B1-1-22) was confirmed as having the structure shown above.

Example 23

Synthesis of Compound (B1-1-23)

With the exception of replacing the 4-methylphenyldiphenylsulfonium bromide with a compound (24), reaction was conducted in the same manner as that described for the synthesis example of ii) in Example 1, thus yielding the compound (B1-1-23).

[Chemical Formula 104]

The thus obtained compound (B1-1-23) was analyzed using ¹H-NMR and ¹⁹F-NMR, and the structure was identified on the basis of the following results.

¹H-NMR (400 MHz, DMSO-d6): δ (ppm)=7.72 to 7.84 (m, 10H, ArH), 7.59 (s, 2H, ArH), 4.84 (ddd, 1H, CH$_2$O), 4.68 (ddd, 1H, CH$_2$O), 4.56 (s, 2H, CH$_2$), 2.49 (m, 2H, adamantane), 2.38 to 2.45 (m, 1H, camphanic), 2.27 to 2.34 (m, 13H, CH$_3$+adamantane), 1.93 to 2.06 (m, 4H, camphanic+adamantane), 1.72 to 1.79 (m, 2H, adamantane), 1.55 to 1.61 (m, 1H, camphanic), 1.04 (s, 3H, CH$_3$), 1.03 (s, 3H, CH$_3$), 0.85 (s, 3H, CH$_3$)

¹⁹F-NMR (376 MHz, DMSO-d6): δ (ppm)=−111.0

Based on the results of the above NMR analyses, the compound (B1-1-23) was confirmed as having the structure shown above.

Example 24

Synthesis of Compound (B1-1-24)

With the exception of replacing the 4-methylphenyldiphenylsulfonium bromide with a compound (25), reaction was conducted in the same manner as that described for the synthesis example of ii) in Example 1, thus yielding the compound (B1-1-24).

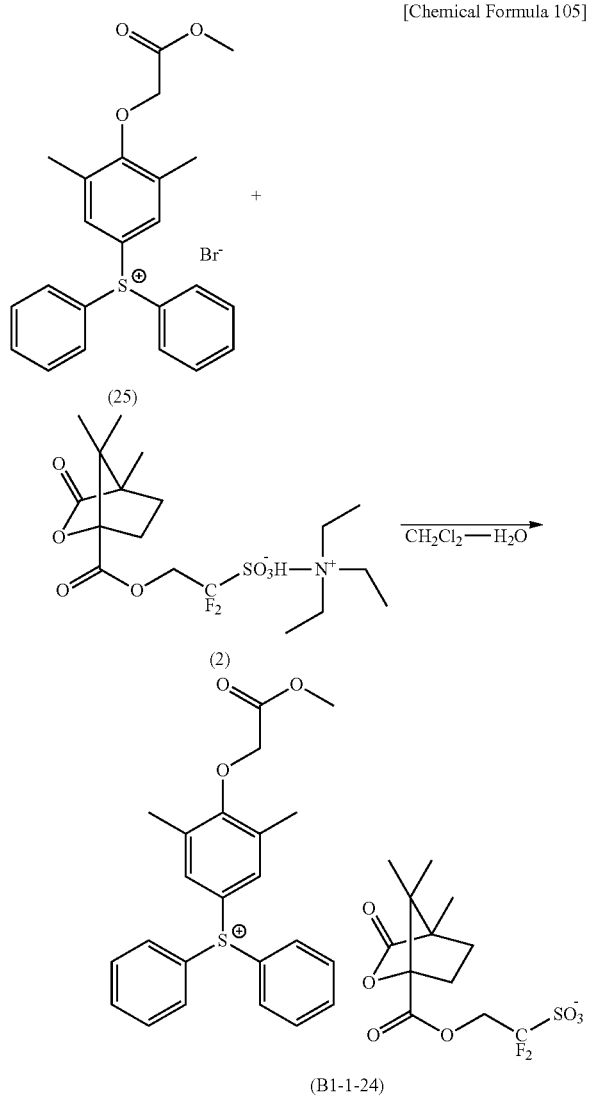

[Chemical Formula 105]

The thus obtained compound (B1-1-24) was analyzed using $^1$H-NMR and $^{19}$F-NMR, and the structure was identified on the basis of the following results.

$^1$H-NMR (400 MHz, DMSO-d6): δ (ppm)=7.72 to 7.84 (m, 10H, ArH), 7.59 (s, 2H, ArH), 4.84 (ddd, 1H, CH$_2$O), 4.68 (ddd, 1H, CH$_2$O), 4.64 (s, 2H, CH$_2$), 3.70 (s, 3H, OCH$_3$), 2.38 to 2.45 (m, 1H, camphanic), 2.29 (s, 6H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-24) was confirmed as having the structure shown above.

Example 25

Synthesis of Compound (B1-1-25)

With the exception of replacing the 4-methylphenyldiphenylsulfonium bromide with a compound (26), reaction was conducted in the same manner as that described for the synthesis example of ii) in Example 1, thus yielding the compound (B1-1-25).

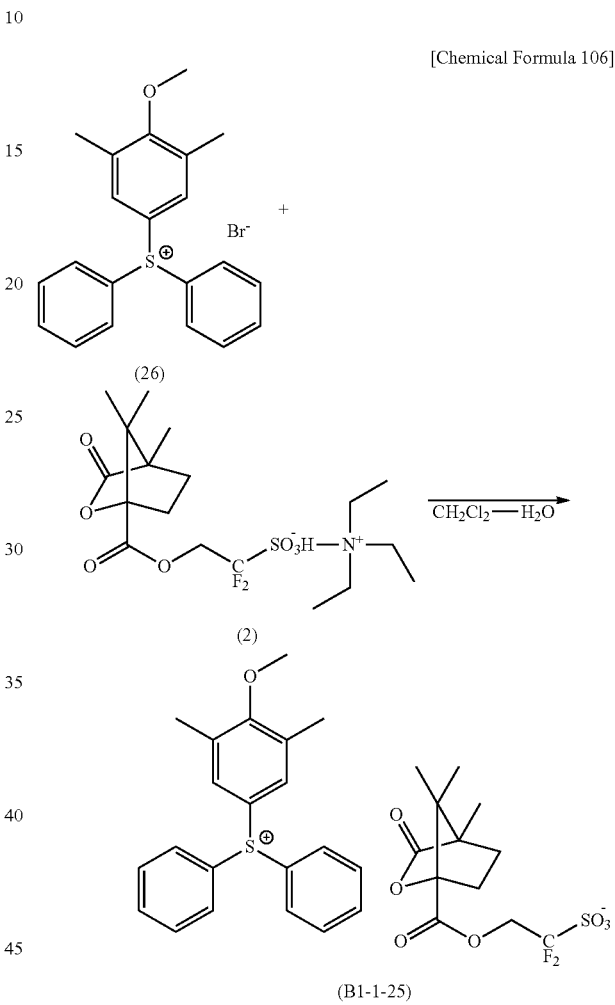

[Chemical Formula 106]

The thus obtained compound (B1-1-25) was analyzed using $^1$H-NMR and $^{19}$F-NMR, and the structure was identified on the basis of the following results.

$^1$H-NMR (400 MHz, DMSO-d6): δ (ppm)=7.78 to 7.89 (m, 10H, ArH), 7.64 (s, 2H, ArH), 4.84 (ddd, 1H, CH$_2$O), 4.68 (ddd, 1H, CH$_2$O), 3.79 (s, 3H, OCH$_3$), 2.38 to 2.45 (m, 1H, camphanic), 2.32 (s, 6H, CH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-25) was confirmed as having the structure shown above.

Example 26

Synthesis of Compound (B1-1-26)

With the exception of replacing the 4-methylphenyldiphenylsulfonium bromide with a compound (27), reaction was conducted in the same manner as that described for the synthesis example of ii) in Example 1, thus yielding the compound (B1-1-26).
The thus obtained compound (B1-1-26) was analyzed using $^1$H-NMR and $^{19}$F-NMR, and the structure was identified on the basis of the following results.
[Chemical Formula 107]
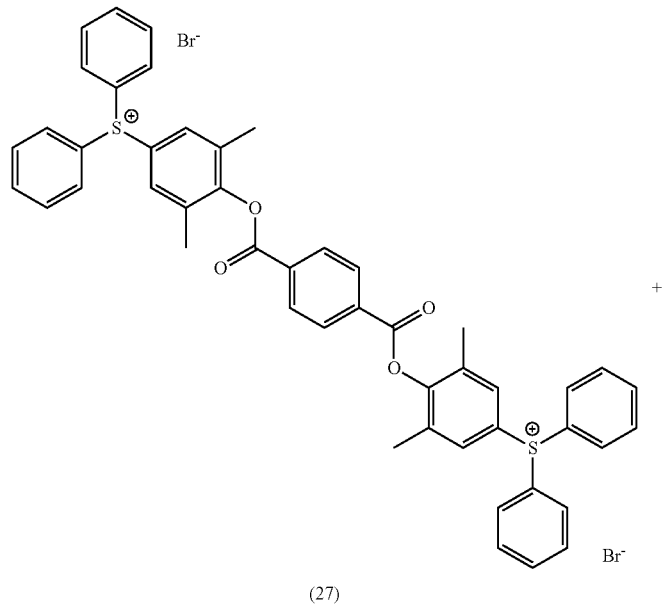
(27)
+
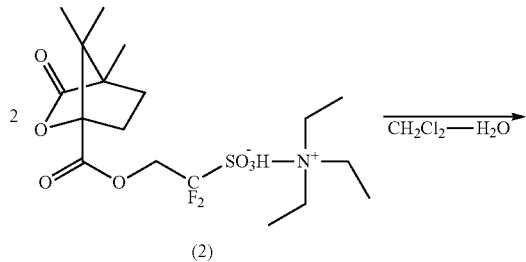
(2)
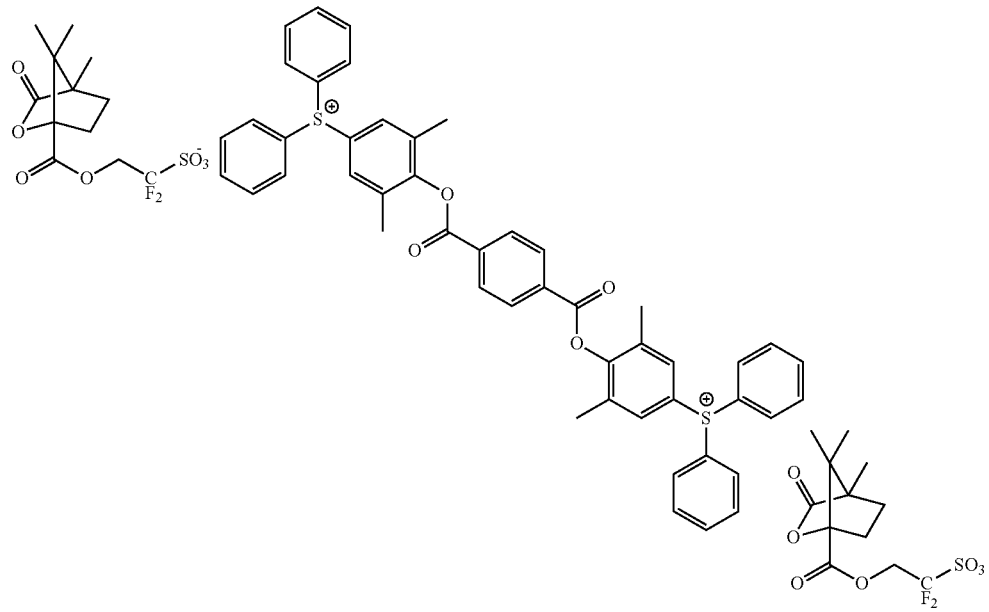
(B1-1-26)

$^1$H-NMR (400 MHz, DMSO-d6): δ (ppm)=8.44 (s, 4H, ArH in ArC=O), 7.78 to 7.90 (m, 24H, ArH), 4.84 (ddd, 2H, $CH_2O$), 4.68 (ddd, 2H, $CH_2O$), 2.38 to 2.45 (m, 2H, camphanic), 2.23 (s, 12H, $CH_3$), 1.93 to 2.06 (m, 4H, camphanic), 1.55 to 1.61 (m, 2H, camphanic), 1.04 (s, 6H, $CH_3$), 1.03 (s, 6H, $CH_3$), 0.85 (s, 6H, $CH_3$)

$^{19}$F-NMR (376 MHz, DMSO-d6): δ (ppm)=−111.0

Based on the results of the above NMR analyses, the compound (B1-1-26) was confirmed as having the structure shown above.

Example 27

Synthesis of Compound (B1-1-27)

With the exception of replacing the 4-methylphenyldiphenylsulfonium bromide with a compound (28), reaction was conducted in the same manner as that described for the synthesis example of ii) in Example 1, thus yielding the compound (B1-1-27).

[Chemical Formula 108]

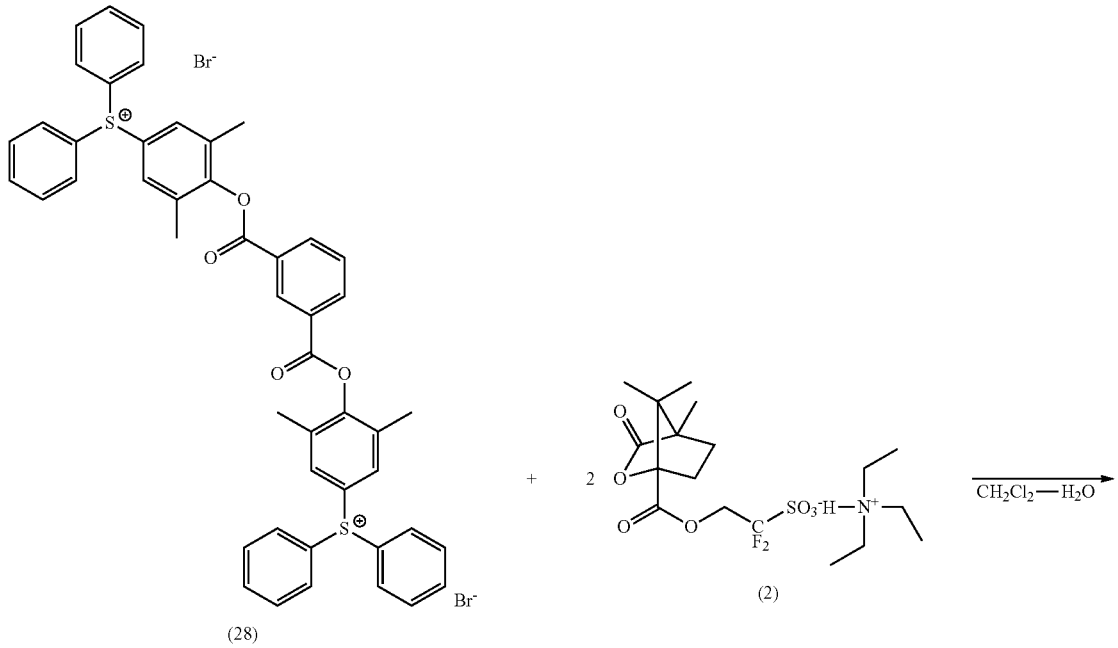

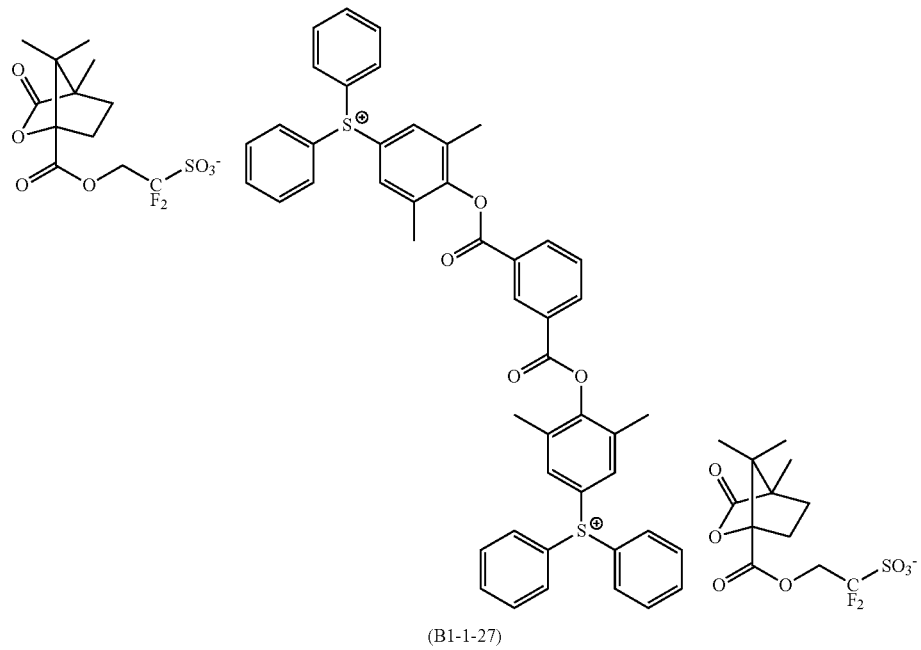

The thus obtained compound (B1-1-27) was analyzed using $^1$H-NMR and $^{19}$F-NMR, and the structure was identified on the basis of the following results.

$^1$H-NMR (400 MHz, DMSO-d6): δ (ppm)=8.90 (s, 1H, ArH in ArC=O), 8.60 (dd, 2H, ArH in ArC=O), 7.77 to 7.96 (m, 25H, ArH in cation+ArH in ArC=O), 4.84 (ddd, 2H, CH$_2$O), 4.68 (ddd, 2H, CH$_2$O), 2.38 to 2.45 (m, 2H, camphanic), 2.24 (s, 12H, CH$_3$), 1.93 to 2.06 (m, 4H, camphanic), 1.55 to 1.61 (m, 2H, camphanic), 1.04 (s, 6H, CH$_3$), 1.03 (s, 6H, CH$_3$), 0.85 (s, 6H, CH$_3$)

$^{19}$F-NMR (376 MHz, DMSO-d6): δ (ppm)=−111.0

Based on the results of the above NMR analyses, the compound (B1-1-27) was confirmed as having the structure shown above.

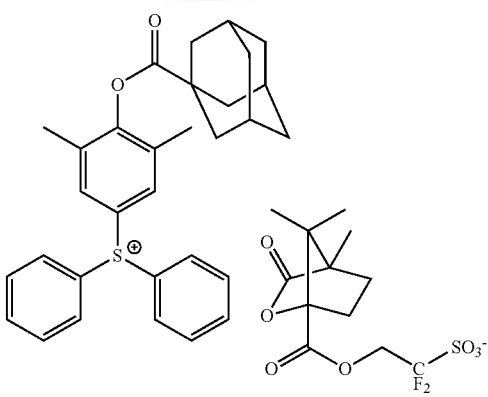

(B1-1-28)

The thus obtained compound (B1-1-28) was analyzed using $^1$H-NMR and $^{19}$F-NMR, and the structure was identified on the basis of the following results.

$^1$H-NMR (400 MHz, DMSO-d6): δ (ppm)=7.76 to 7.87 (m, 10H, ArH), 7.69 (s, 2H, ArH), 4.84 (ddd, 1H, CH$_2$O), 4.68 (ddd, 1H, CH$_2$O), 2.38 to 2.45 (m, 1H, camphanic), 2.13 (s, 6H, CH$_3$), 1.66 to 2.06 (m, 17H, camphanic+adamantane), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-28) was confirmed as having the structure shown above.

Example 28

Synthesis of Compound (B1-1-28)

With the exception of replacing the 4-methylphenyldiphenylsulfonium bromide with a compound (29), reaction was conducted in the same manner as that described for the synthesis example of ii) in Example 1, thus yielding the compound (B1-1-28).

[Chemical Formula 109]

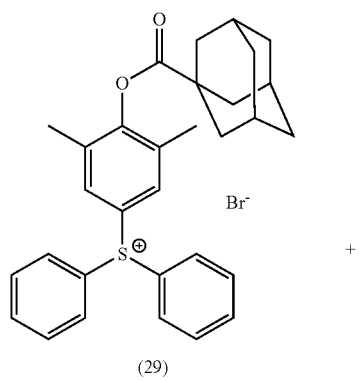

(29)

Example 29

Synthesis of Compound (B1-1-29)

With the exception of replacing the 4-methylphenyldiphenylsulfonium bromide with a compound (30), reaction was conducted in the same manner as that described for the synthesis example of ii) in Example 1, thus yielding the compound (B1-1-29).

[Chemical Formula 110]

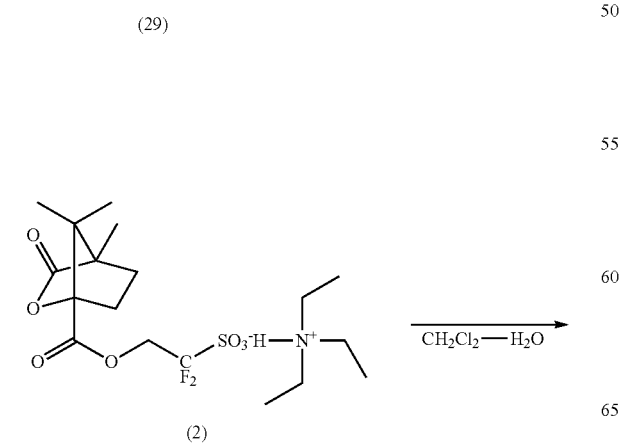

(2)

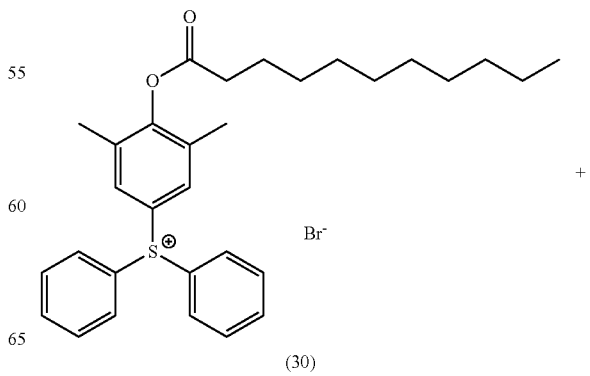

(30)

-continued

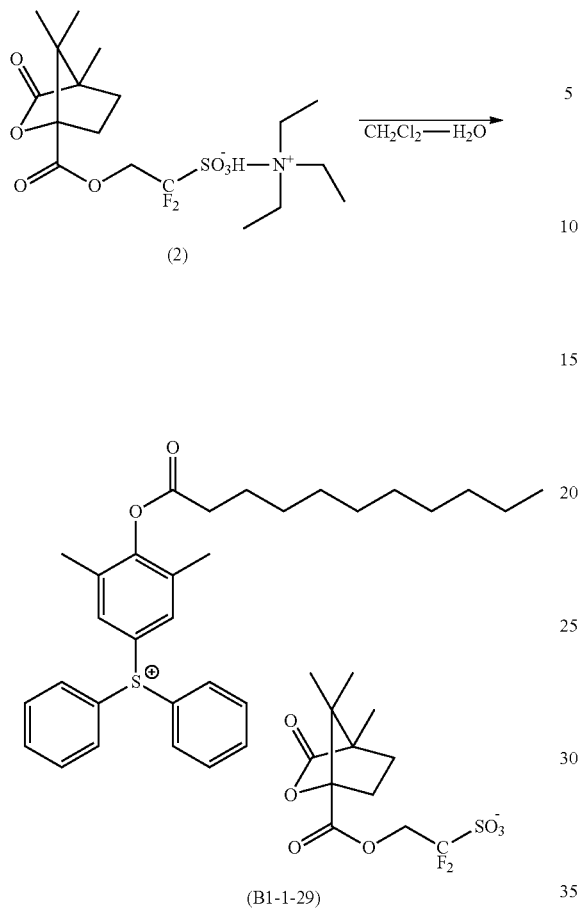

(2)

(B1-1-29)

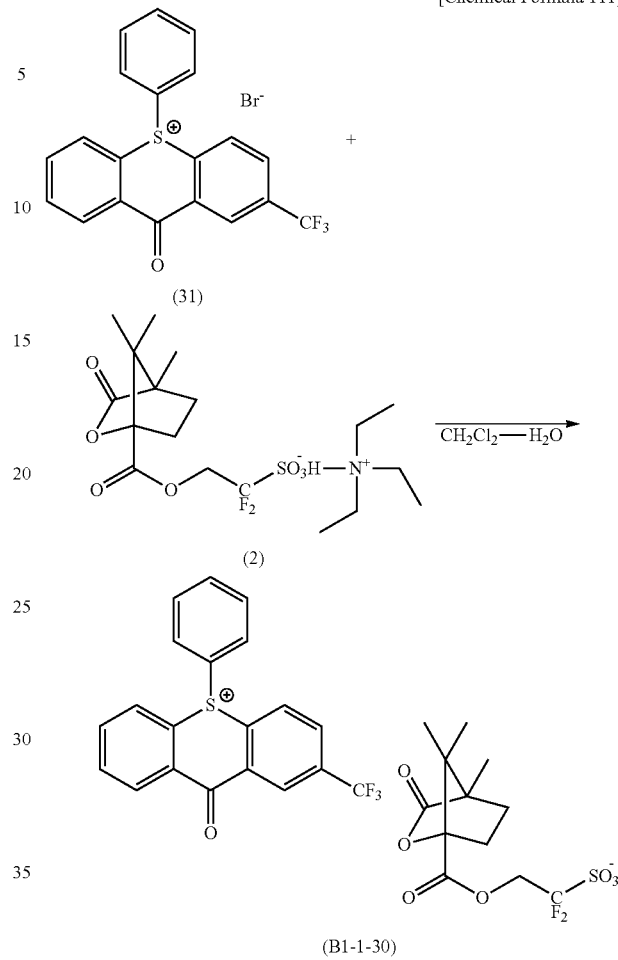

(31)

(2)

(B1-1-30)

The thus obtained compound (B1-1-29) was analyzed using $^1$H-NMR and $^{19}$F-NMR, and the structure was identified on the basis of the following results.

$^1$H-NMR (400 MHz, DMSO-d6): δ (ppm)=7.79 to 7.93 (m, 12H, ArH), 4.84 (ddd, 1H, CH$_2$O), 4.68 (ddd, 1H, CH$_2$O), 2.73 (t, 2H, CO—CH$_2$), 2.38 to 2.45 (m, 1H, camphanic), 2.19 (s, 6H, ArCH$_3$), 1.93 to 2.06 (m, 2H, camphanic), 1.65 to 1.72 (m, 2H, CH$_2$), 1.55 to 1.61 (m, 1H, camphanic), 1.25 to 1.38 (m, 14H, CH$_2$), 1.04 (s, 3H, CH$_3$), 1.03 (s, 3H, CH$_3$), 0.85 (m, 6H, CH$_3$)

$^{19}$F-NMR (376 MHz, DMSO-d6): δ (ppm)=−111.0

Based on the results of the above NMR analyses, the compound (B1-1-29) was confirmed as having the structure shown above.

Example 30

Synthesis of Compound (B1-1-30)

With the exception of replacing the 4-methylphenyldiphenylsulfonium bromide with a compound (31), reaction was conducted in the same manner as that described for the synthesis example of ii) in Example 1, thus yielding the compound (B1-1-30).

The thus obtained compound (B1-1-30) was analyzed using $^1$H-NMR and $^{19}$F-NMR, and the structure was identified on the basis of the following results.

$^1$H-NMR (400 MHz, DMSO-d6): δ (ppm)=8.76 (s, 1H, ArH), 8.59 to 8.64 (m, 1H, ArH), 8.42 (t, 2H, ArH), 8.03 to 8.19 (m, 5H, ArH), 7.81 (t, 1H, ArH), 7.69 (t, 2H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−62.1, −111.0

Based on the results of the above NMR analyses, the compound (B1-1-30) was confirmed as having the structure shown above.

Example 31

Synthesis of Compound (B1-1-31)

With the exception of replacing the 4-methylphenyldiphenylsulfonium bromide with a compound (32), reaction was conducted in the same manner as that described for the synthesis example of ii) in Example 1, thus yielding the compound (B1-1-31).

[Chemical Formula 112]

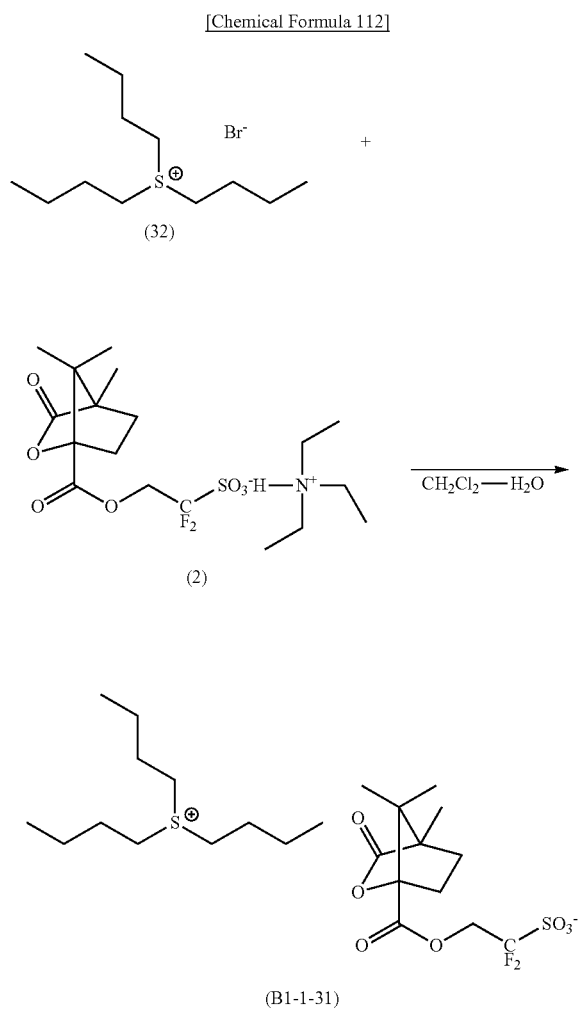

The thus obtained compound (B1-1-31) was analyzed using $^1$H-NMR and $^{19}$F-NMR, and the structure was identified on the basis of the following results.

$^1$H-NMR (400 MHz, DMSO-d6): δ (ppm)=4.84 (ddd, 1H, CH$_2$O), 4.68 (ddd, 1H, CH$_2$O), 3.36 (t, 6H, CH$_2$), 2.38 to 2.45 (m, 1H, camphanic), 1.93 to 2.06 (m, 2H, camphanic), 1.68 (quintet, 6H, CH$_2$), 1.55 to 1.61 (m, 1H, camphanic), 1.35 to 1.44 (m, 6H, CH$_2$), 1.04 (s, 3H, CH$_3$), 1.03 (s, 3H, CH$_3$), 0.81 to 0.93 (m, 12H, CH$_3$)

$^{19}$F-NMR (376 MHz, DMSO-d6): δ (ppm)=−111.0

Based on the results of the above NMR analyses, the compound (B1-1-31) was confirmed as having the structure shown above.

Example 32

Synthesis of Compound (B1-1-32)

With the exception of replacing the 4-methylphenyldiphenylsulfonium bromide with a compound (33), reaction was conducted in the same manner as that described for the synthesis example of ii) in Example 1, thus yielding the compound (B1-1-32).

[Chemical Formula 113]

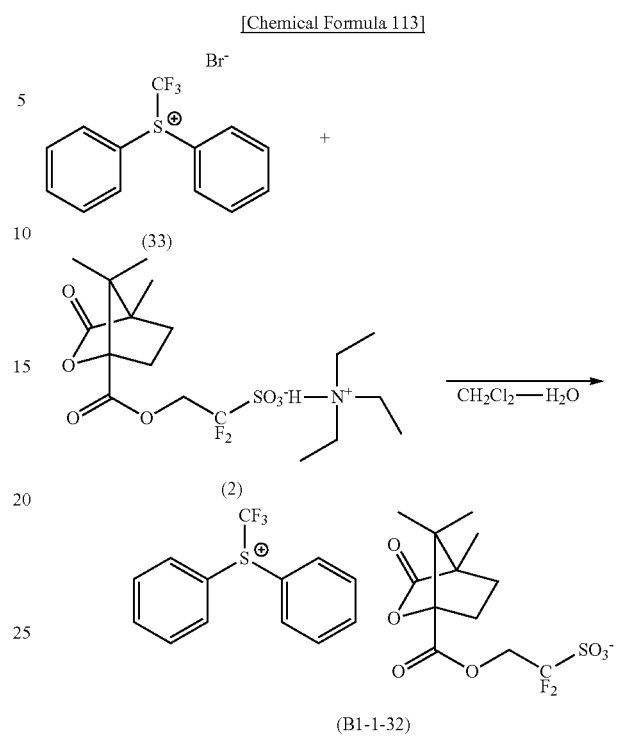

The thus obtained compound (B1-1-32) was analyzed using $^1$H-NMR and $^{19}$F-NMR, and the structure was identified on the basis of the following results.

$^1$H-NMR (400 MHz, DMSO-d6): δ (ppm)=8.29 (d, 4H, ArH), 7.93 to 8.09 (m, 6H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−47.9, −111.0

Based on the results of the above NMR analyses, the compound (B1-1-32) was confirmed as having the structure shown above.

Example 33

Synthesis of Compound (B1-1-33)

With the exception of replacing the 4-methylphenyldiphenylsulfonium bromide with a compound (34), reaction was conducted in the same manner as that described for the synthesis example of ii) in Example 1, thus yielding the compound (B1-1-33).

[Chemical Formula 114]

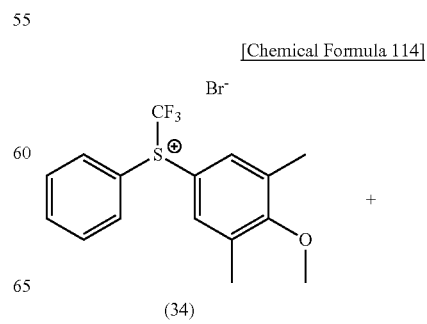

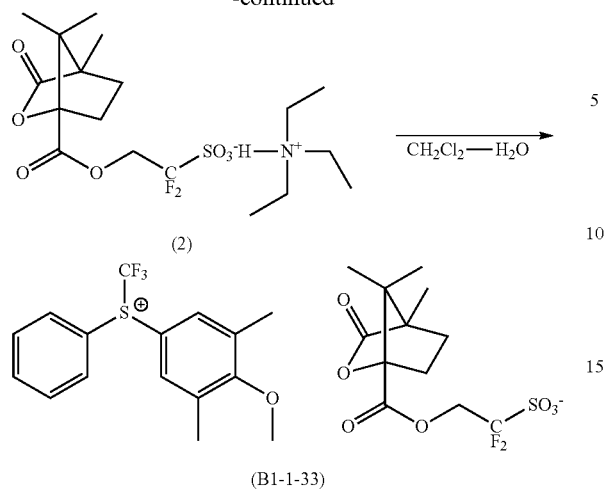

The thus obtained compound (B1-1-33) was analyzed using ¹H-NMR and ¹⁹F-NMR, and the structure was identified on the basis of the following results.

¹H-NMR (400 MHz, DMSO-d6): δ (ppm)=7.90 to 8.24 (m, 7H, ArH), 4.84 (ddd, 1H, $CH_2O$), 4.68 (ddd, 1H, $CH_2O$), 3.85 (s, 3H, $OCH_3$), 2.38 to 2.45 (m, 7H, $ArCH_3$+camphanic), 1.93 to 2.06 (m, 2H, camphanic), 1.55 to 1.61 (m, 1H, camphanic), 1.04 (s, 3H, $CH_3$), 1.03 (s, 3H, $CH_3$), 0.85 (s, 3H, $CH_3$)

¹⁹F-NMR (376 MHz, DMSO-d6): δ (ppm)=−48.8, −111.0

Based on the results of the above NMR analyses, the compound (B1-1-33) was confirmed as having the structure shown above.

Example 34

Synthesis of Compound (B1-1-34)

With the exception of replacing the 4-methylphenyldiphenylsulfonium bromide with a compound (35), reaction was conducted in the same manner as that described for the synthesis example of ii) in Example 1, thus yielding the compound (B1-1-34).

[Chemical Formula 115]

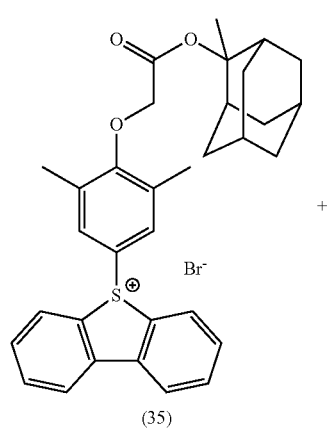

The thus obtained compound (B1-1-34) was analyzed using ¹H-NMR and ¹⁹F-NMR, and the structure was identified on the basis of the following results.

¹H-NMR (400 MHz, DMSO-d6): δ (ppm)=8.49 (d, 2H, ArH), 8.30 (d, 2H, ArH), 7.93 (t, 2H, ArH), 7.73 (t, 2H, ArH), 7.30 (s, 2H, ArH), 4.84 (ddd, 1H, $CH_2O$), 4.68 (ddd, 1H, $CH_2O$), 4.52 (s, 2H, $OCH_2$), 2.38 to 2.45 (m, 1H, camphanic), 2.16 to 2.24 (m, 8H, Ar—$CH_3$+adamantane), 1.93 to 2.06 (m, 2H, camphanic), 1.44 to 1.92 (m, 16H, camphanic+adamantane+$CH_3$), 1.04 (s, 3H, $CH_3$), 1.03 (s, 3H, $CH_3$), 0.85 (s, 3H, $CH_3$)

¹⁹F-NMR (376 MHz, DMSO-d6): δ (ppm)=−111.0

Based on the results of the above NMR analyses, the compound (B1-1-34) was confirmed as having the structure shown above.

Example 35

Synthesis of Compound (B1-1-35)

With the exception of replacing the 4-methylphenyldiphenylsulfonium bromide with a compound (36), reaction was conducted in the same manner as that described for the synthesis example of ii) in Example 1, thus yielding the compound (B1-1-35).

[Chemical Formula 116]

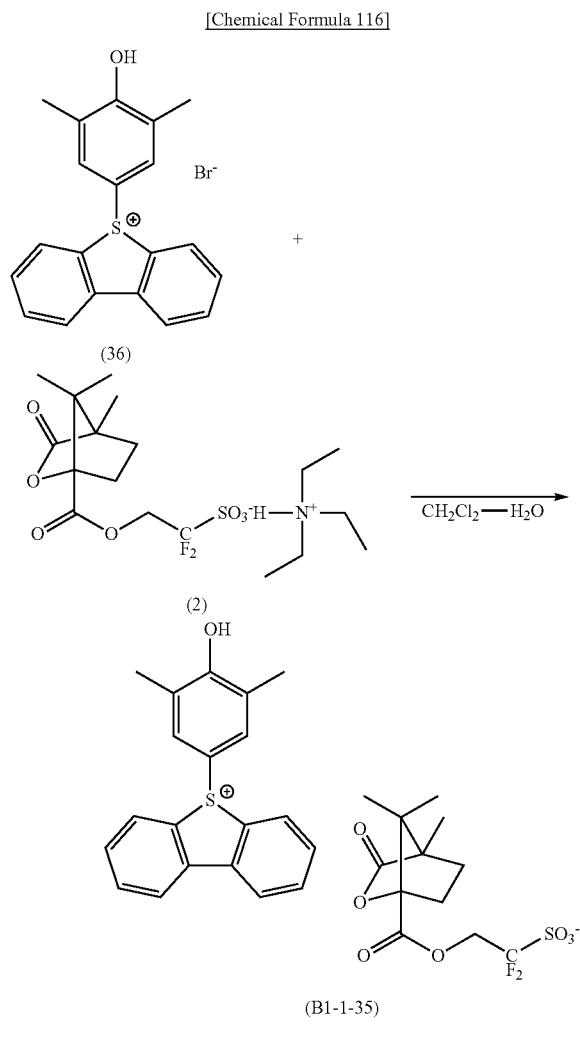

(B1-1-35)

The thus obtained compound (B1-1-35) was analyzed using $^1$H-NMR and $^{19}$F-NMR, and the structure was identified on the basis of the following results.

$^1$H-NMR (400 MHz, DMSO-d6): δ (ppm)=9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.84 (ddd, 1H, CH$_2$O), 4.68 (ddd, 1H, CH$_2$O), 2.38 to 2.45 (m, 1H, camphanic), 2.10 (s, 6H, ArCH$_3$), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-35) was confirmed as having the structure shown above.

Example 36

Synthesis of Compound (B1-1-36)

With the exception of replacing the 4-methylphenyldiphenylsulfonium bromide with a compound (37), reaction was conducted in the same manner as that described for the synthesis example of ii) in Example 1, thus yielding the compound (B1-1-36).

[Chemical Formula 117]

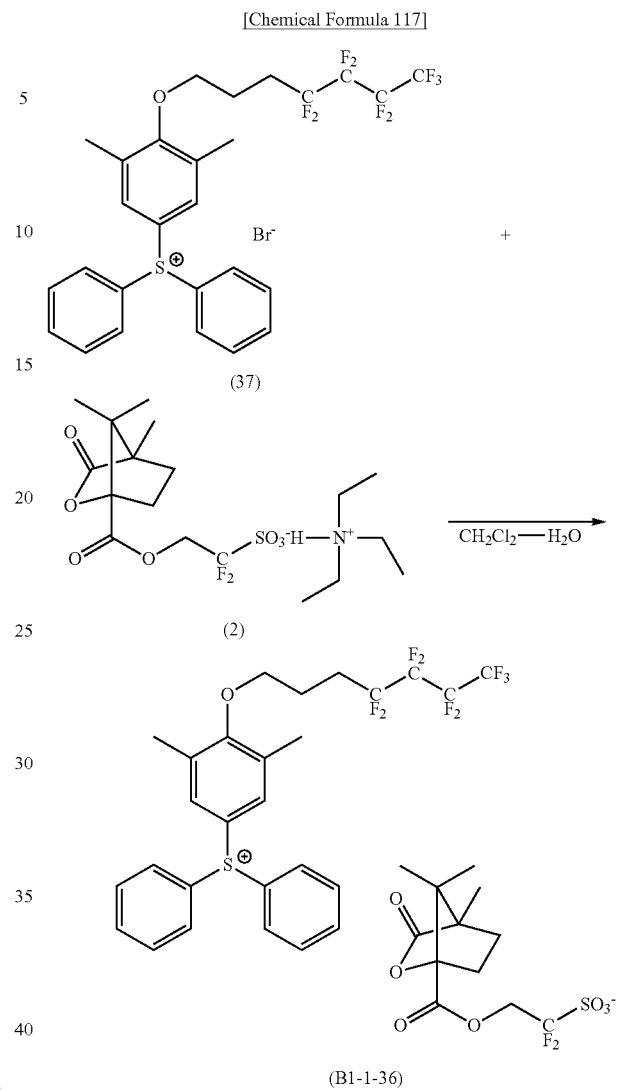

(B1-1-36)

The thus obtained compound (B1-1-36) was analyzed using $^1$H-NMR and $^{19}$F-NMR, and the structure was identified on the basis of the following results.

$^1$H-NMR (400 MHz, DMSO-d6): δ (ppm)=7.75 to 7.87 (m, 10H, ArH), 7.62 (s, 2H, ArH), 4.84 (ddd, 1H, CH$_2$O), 4.68 (ddd, 1H, CH$_2$O), 3.97 (t, 2H, CH$_2$), 1.93 to 2.56 (m, 13H, CH$_2$+CH$_3$+camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−123.5, −121.8, −111.6, −111.0, −78.3

Based on the results of the above NMR analyses, the compound (B1-1-36) was confirmed as having the structure shown above.

Example 37

Synthesis of Compound (B1-1-37)

With the exception of replacing the 4-methylphenyldiphenylsulfonium bromide with a compound (38), reaction was conducted in the same manner as that described for the synthesis example of ii) in Example 1, thus yielding the compound (B1-1-37).

[Chemical Formula 118]

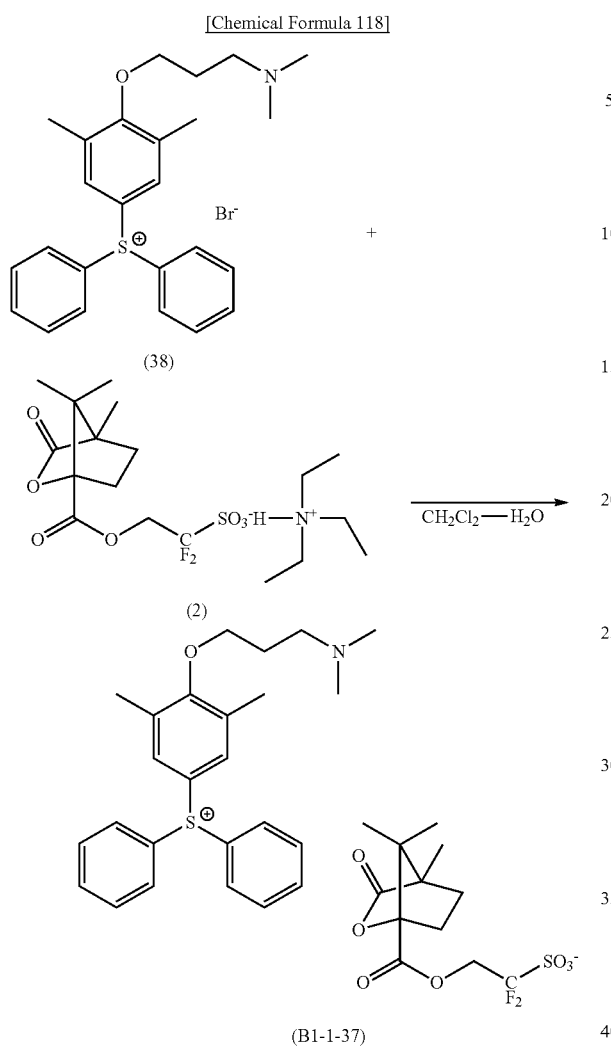

The thus obtained compound (B1-1-37) was analyzed using $^1$H-NMR and $^{19}$F-NMR, and the structure was identified on the basis of the following results.

$^1$H-NMR (400 MHz, DMSO-d6): δ (ppm)=7.75 to 7.86 (m, 10H, ArH), 7.60 (s, 2H, ArH), 4.84 (ddd, 1H, CH$_2$O), 4.68 (ddd, 1H, CH$_2$O), 3.87 (t, 2H, CH$_2$), 2.38 to 2.45 (m, 3H, CH$_2$+camphanic), 2.24 to 2.35 (m, 6H, CH$_2$), 2.12 (m, 6H, N—CH$_3$), 1.93 to 2.06 (m, 2H, camphanic), 1.86 (t, 2H, CH$_2$), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-37) was confirmed as having the structure shown above.

Example 38

Synthesis of Compound (B1-1-38)

With the exception of replacing the 4-methylphenyldiphenylsulfonium bromide with a compound (39), reaction was conducted in the same manner as that described for the synthesis example of ii) in Example 1, thus yielding the compound (B1-1-38).

[Chemical Formula 119]

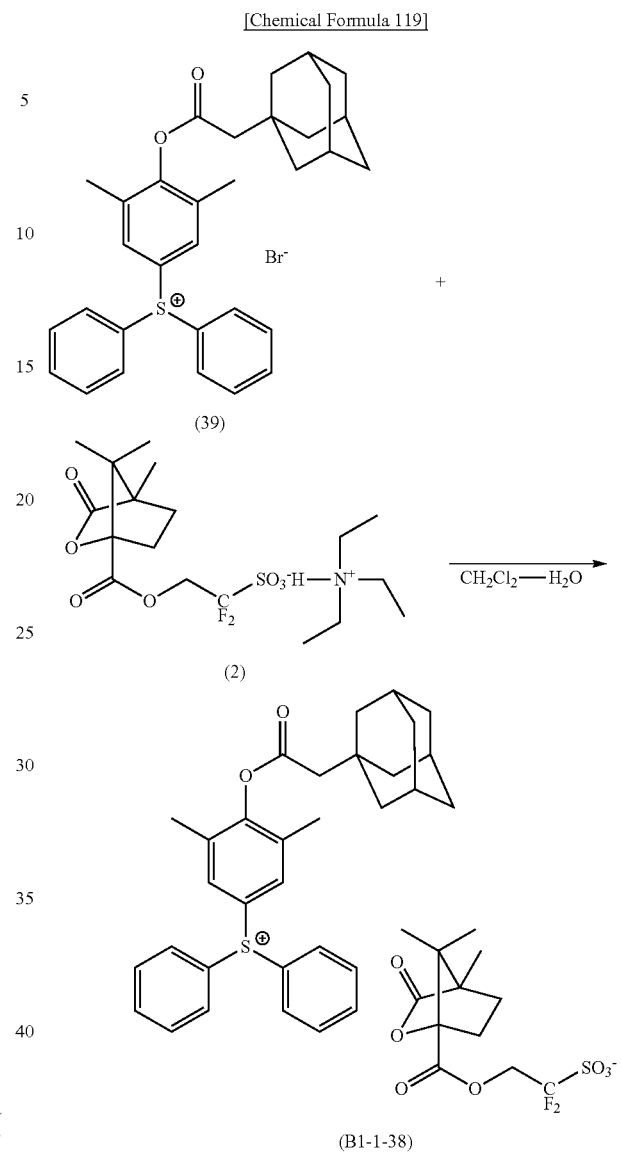

The thus obtained compound (B1-1-38) was analyzed using $^1$H-NMR and $^{19}$F-NMR, and the structure was identified on the basis of the following results.

$^1$H-NMR (400 MHz, DMSO-d6): δ (ppm)=7.77 to 7.89 (m, 10H, ArH), 7.71 (s, 2H, ArH), 4.84 (ddd, 1H, CH$_2$O), 4.68 (ddd, 1H, CH$_2$O), 2.51 (s, 2H, CH$_2$), 2.38 to 2.45 (m, 1H, camphanic), 2.20 (s, 6H, CH$_3$), 1.93 to 2.06 (m, 5H, adamantane+camphanic), 1.62 to 1.73 (m, 12H, adamantane), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-38) was confirmed as having the structure shown above.

Example 39

Synthesis of Compound (B1-1-39)

With the exception of replacing the 4-methylphenyldiphenylsulfonium bromide with a compound (40), reaction was conducted in the same manner as that described for the synthesis example of ii) in Example 1, thus yielding the compound (B1-1-39).

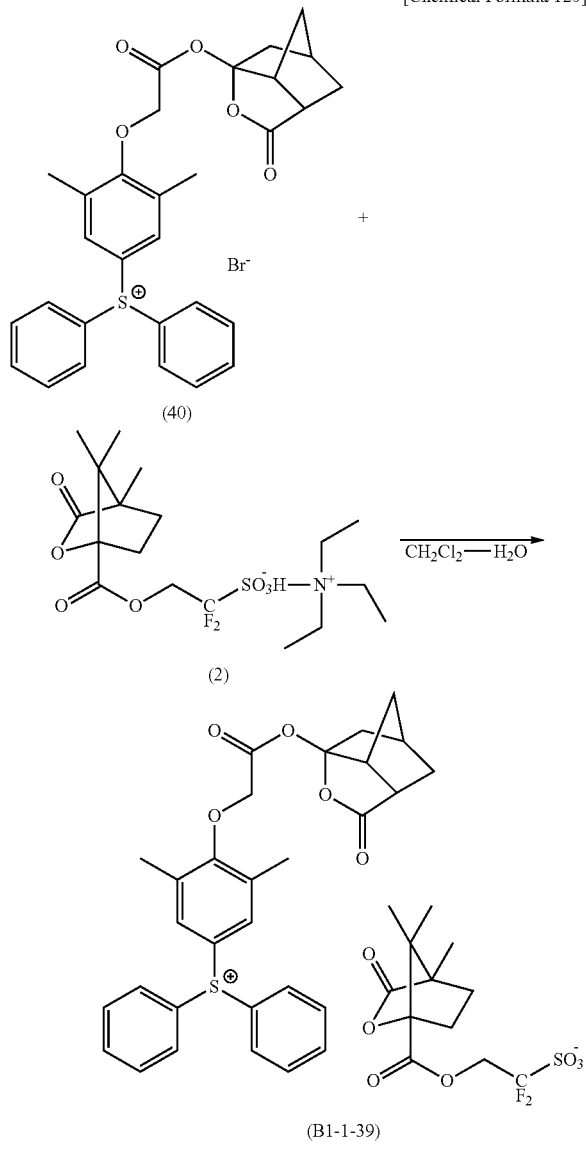

The thus obtained compound (B1-1-39) was analyzed using $^1$H-NMR and $^{19}$F-NMR, and the structure was identified on the basis of the following results.

$^1$H-NMR (400 MHz, DMSO-d6): δ (ppm)=7.74 to 7.84 (m, 10H, ArH), 7.61 (s, 2H, ArH), 4.84 (ddd, 1H, CH$_2$O), 4.68 (ddd, 1H, CH$_2$O), 4.49 to 4.66 (m, 4H, norbornane+OCH$_2$), 3.24 (m, 1H, norbornane), 2.46 to 2.54 (m, 2H, norbornane), 2.38 to 2.45 (m, 1H, camphanic), 2.37 (s, 6H, ArCH$_3$), 1.91 to 2.06 (m, 4H, norbornane+camphanic), 1.55 to 1.67 (m, 3H, norbornane+camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-39) was confirmed as having the structure shown above.

Example 40

Synthesis of Compound (B1-1-40)

With the exception of replacing the 4-methylphenyldiphenylsulfonium bromide with a compound (41), reaction was conducted in the same manner as that described for the synthesis example of ii) in Example 1, thus yielding the compound (B1-1-40).

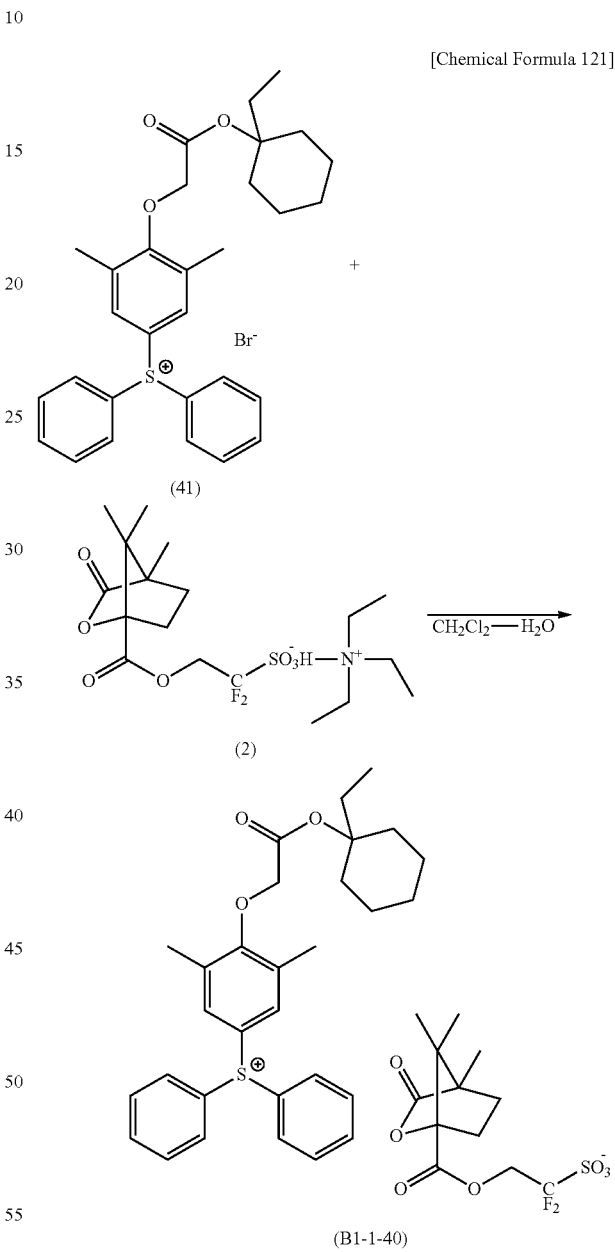

The thus obtained compound (B1-1-40) was analyzed using $^1$H-NMR and $^{19}$F-NMR, and the structure was identified on the basis of the following results.

$^1$H-NMR (400 MHz, DMSO-d6): δ (ppm)=7.80 to 7.92 (m, 10H, ArH), 7.67 (s, 2H, ArH), 4.84 (ddd, 1H, CH$_2$O), 4.68 (ddd, 1H, CH$_2$O), 4.66 (s, 2H, CH$_2$), 2.38 to 2.45 (m, 1H, camphanic), 2.37 (s, 6H, ArCH$_3$), 2.13 to 2.16 (m, 2H, cyclohexyl), 1.93 to 2.06 (m, 2H, camphanic), 1.91 (q, 2H, CH$_2$), 1.14 to 1.61 (m, 9H, cyclohexyl+camphanic), 1.04 (s, 3H, CH$_3$), 1.03 (s, 3H, CH$_3$), 0.85 (m, 6H, CH$_3$)

$^{19}$F-NMR (376 MHz, DMSO-d6): δ (ppm)=−111.0

Based on the results of the above NMR analyses, the compound (B1-1-40) was confirmed as having the structure shown above.

Example 41

Synthesis of Compound (B1-1-41)

With the exception of replacing the 4-methylphenyldiphenylsulfonium bromide with a compound (42), reaction was conducted in the same manner as that described for the synthesis example of ii) in Example 1, thus yielding the compound (B1-1-41).

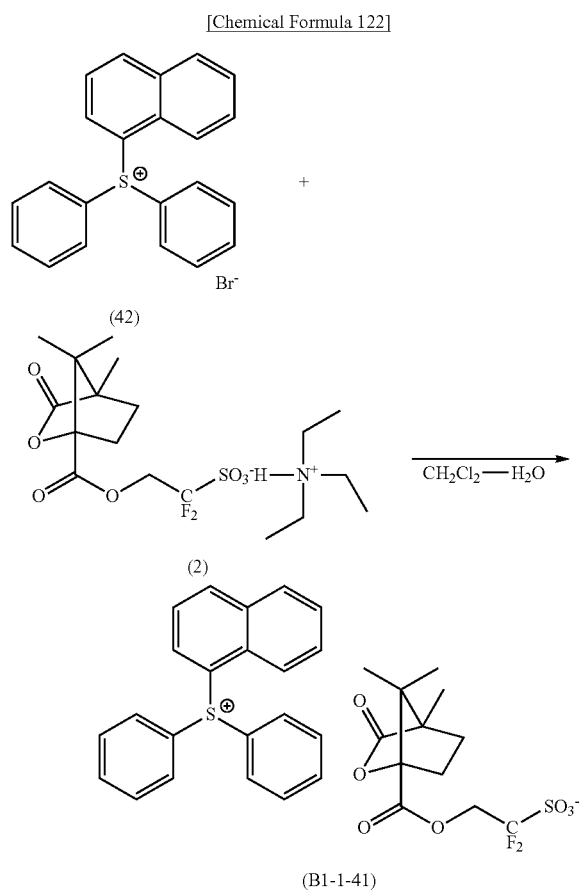

The thus obtained compound (B1-1-41) was analyzed using $^1$H-NMR and $^{19}$F-NMR, and the structure was identified on the basis of the following results.

$^1$H-NMR (400 MHz, DMSO-d6): δ (ppm)=8.44 (d, 1H, ArH), 8.22 (m, 2H, ArH), 7.73 to 7.89 (m, 13H, ArH), 7.50 (d, 1H, ArH), 4.22 (s, 2H, CH$_2$O), 4.05 (t, 2H, CH$_2$CF$_2$), 2.24 (br s, 2H, adamantane), 1.53 to 1.99 (m, 15H, adamantane+CH$_3$ in anion)

$^{19}$F-NMR (376 MHz, DMSO-d6): δ (ppm)=−111.0

Based on the results of the above NMR analyses, the compound (B1-1-41) was confirmed as having the structure shown above.

Example 42

Synthesis of Compound (B1-1-42)

With the exception of replacing the 4-methylphenyldiphenylsulfonium bromide with a compound (43), reaction was conducted in the same manner as that described for the synthesis example of ii) in Example 1, thus yielding the compound (B1-1-42).

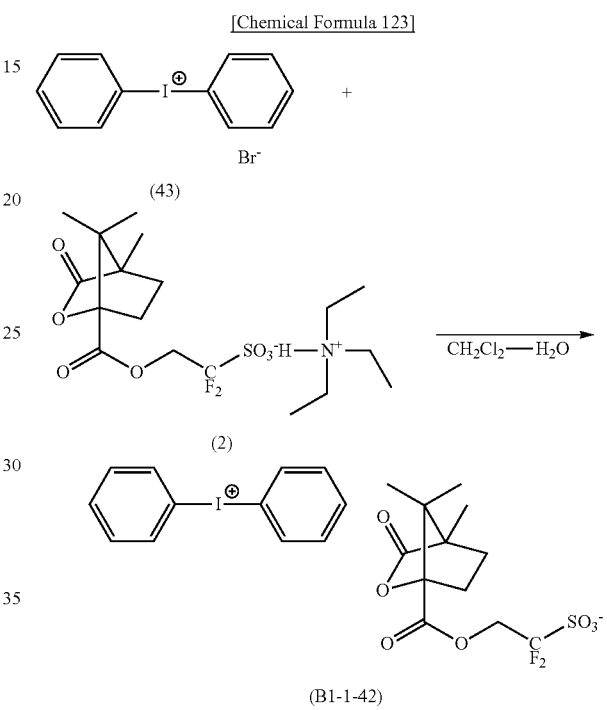

The thus obtained compound (B1-1-42) was analyzed using $^1$H-NMR and $^{19}$F-NMR, and the structure was identified on the basis of the following results.

$^1$H-NMR (400 MHz, DMSO-d6): δ (ppm)=8.24 (d, 4H, ArH), 7.59 (t, 2H, ArH), 7.47 (t, 4H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-42) was confirmed as having the structure shown above.

Example 43

Synthesis of Compound (B1-1-43)

With the exception of replacing the 4-methylphenyldiphenylsulfonium bromide with a compound (44), reaction was conducted in the same manner as that described for the synthesis example of ii) in Example 1, thus yielding the compound (B1-1-43).

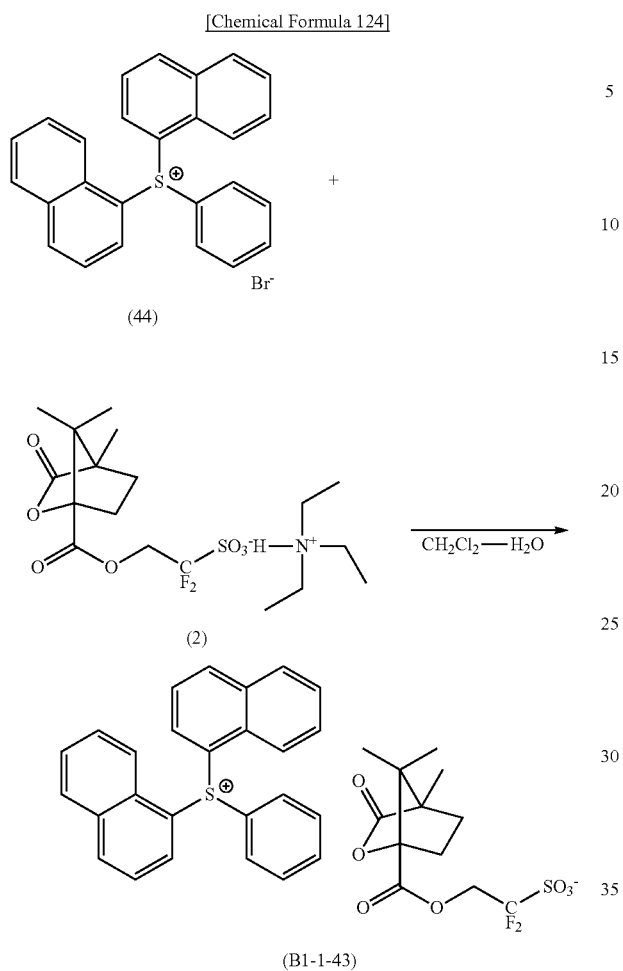

(44)

(2)

(B1-1-43)

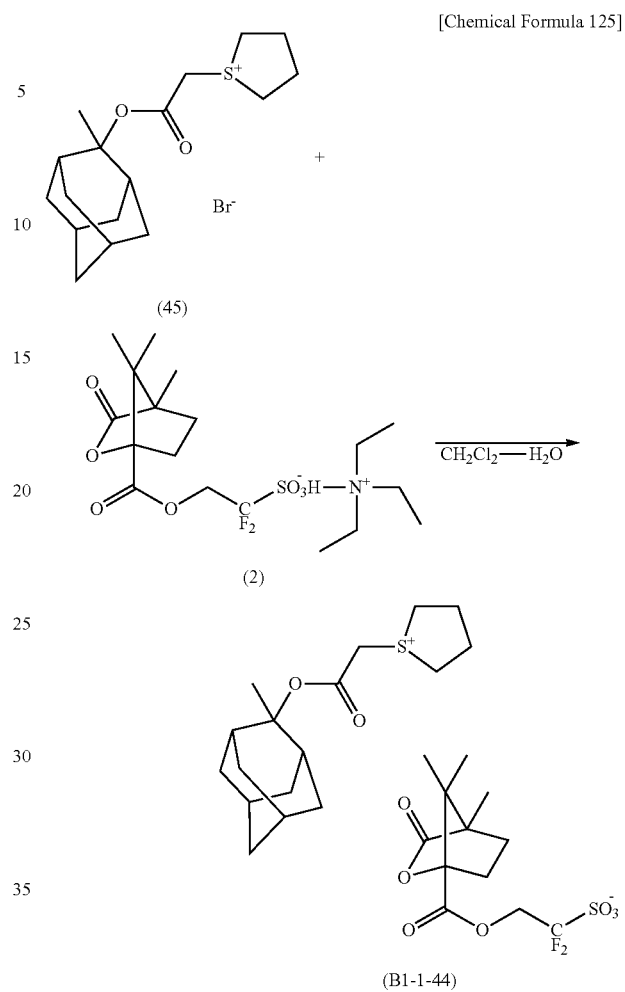

(45)

(2)

(B1-1-44)

The thus obtained compound (B1-1-43) was analyzed using $^1$H-NMR and $^{19}$F-NMR, and the structure was identified on the basis of the following results.

$^1$H-NMR (400 MHz, DMSO-d6): δ (ppm)=8.55 (d, 2H, ArH), 8.38 (d, 2H, ArH), 8.32 (d, 2H, ArH), 8.03 (d, 2H, ArH), 7.93 to 7.97 (m, 1H, ArH), 7.82 to 7.88 (m, 8H, ArH), 7.55 (d, 2H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-43) was confirmed as having the structure shown above.

Example 44

Synthesis of Compound (B1-1-44)

With the exception of replacing the 4-methylphenyldiphenylsulfonium bromide with a compound (45), reaction was conducted in the same manner as that described for the synthesis example of ii) in Example 1, thus yielding the compound (B1-1-44).

The thus obtained compound (B1-1-44) was analyzed using $^1$H-NMR and $^{19}$F-NMR, and the structure was identified on the basis of the following results.

$^1$H-NMR (400 MHz, DMSO-d6): δ (ppm)=4.84 (ddd, 1H, CH$_2$O), 4.68 (ddd, 1H, CH$_2$O), 4.46 (s, 2H, CH$_2$(C=O)), 3.38 to 3.58 (m, 4H, CH$_2$SCH$_2$), 2.38 to 2.45 (m, 1H, camphanic), 1.55 to 2.33 (m, 24H, camphanic+adamantane+CH$_2$CH$_2$), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-44) was confirmed as having the structure shown above.

Example 45

Synthesis of Compound (B1-1-45)

With the exception of replacing the 4-methylphenyldiphenylsulfonium bromide with a compound (46), reaction was conducted in the same manner as that described for the synthesis example of ii) in Example 1, thus yielding the compound (B1-1-45).

[Chemical Formula 126]

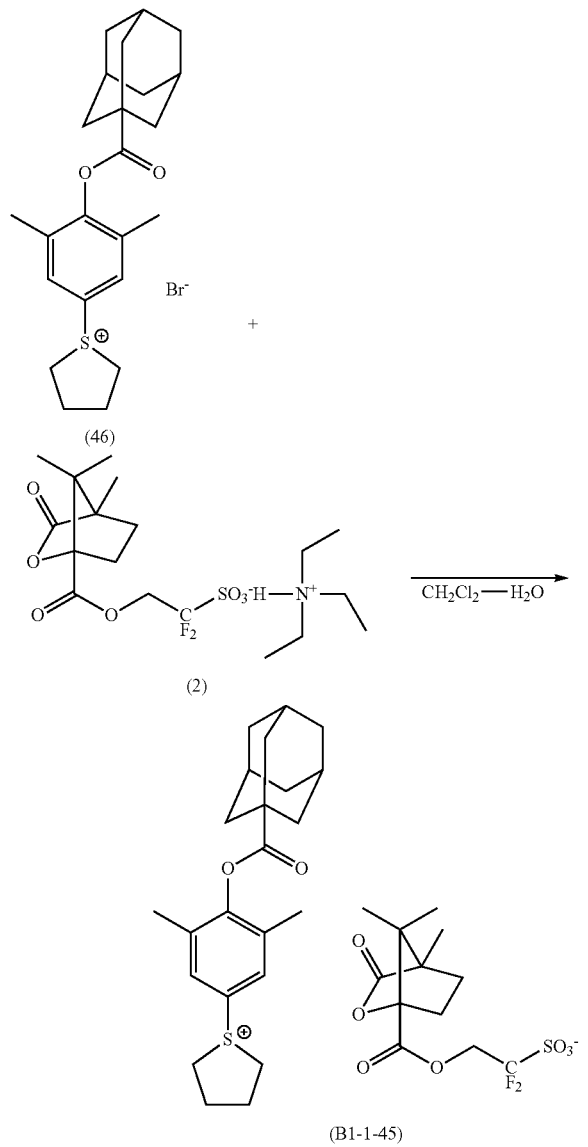

The thus obtained compound (B1-1-45) was analyzed using ¹H-NMR and ¹⁹F-NMR, and the structure was identified on the basis of the following results.

$^1$H-NMR (400 MHz, DMSO-d6): δ (ppm)=7.75 (s, 2H, Ar), 4.84 (ddd, 1H, CH₂O), 4.68 (ddd, 1H, CH₂O), 3.91 to 3.96 (m, 2H, CH₂), 3.72 to 3.79 (m, 2H, CH₂), 2.29 to 2.45 (m, 5H, CH₂+camphanic), 1.75 to 2.19 (m, 23H, Ar—CH₃+ adamantane+camphanic), 1.55 to 1.61 (m, 1H, camphanic), 1.04 (s, 3H, CH₃), 1.03 (s, 3H, CH₃), 0.85 (s, 3H, CH₃)

$^{19}$F-NMR (376 MHz, DMSO-d6): δ (ppm)=−111.0

Based on the results of the above NMR analyses, the compound (B1-1-45) was confirmed as having the structure shown above.

Example 46

Synthesis of Compound (B1-1-46)

With the exception of replacing the 4-methylphenyldiphenylsulfonium bromide with a compound (47), reaction was conducted in the same manner as that described for the synthesis example of ii) in Example 1, thus yielding the compound (B1-1-46).

[Chemical Formula 127]

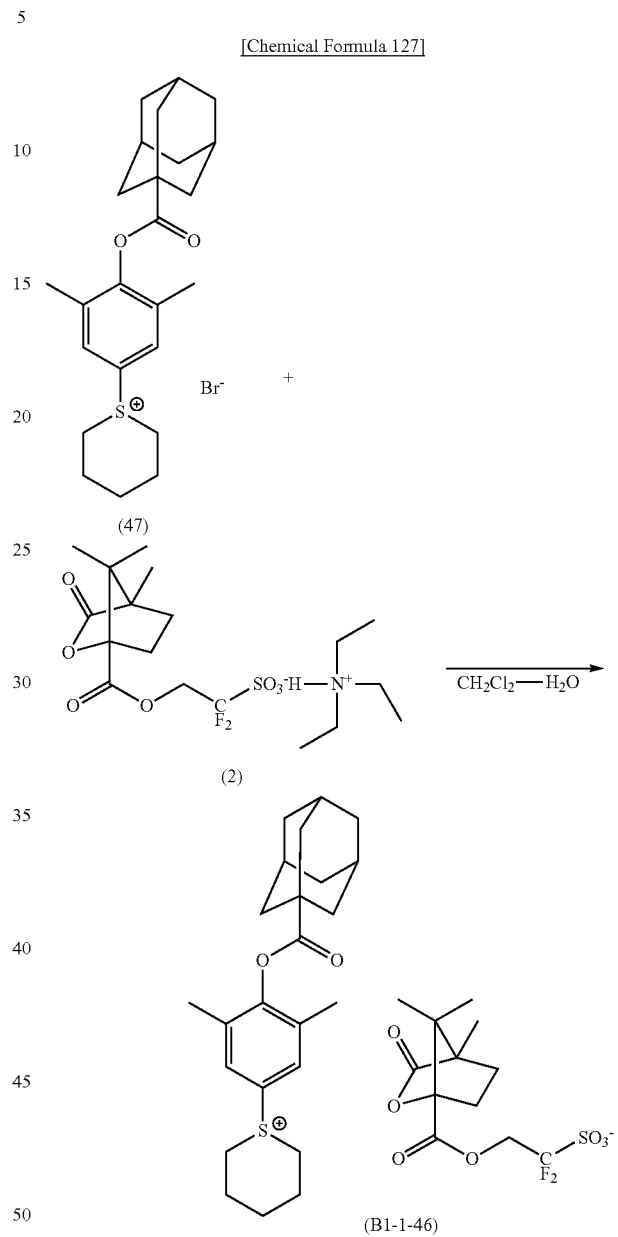

The thus obtained compound (B1-1-46) was analyzed using ¹H-NMR and ¹⁹F-NMR, and the structure was identified on the basis of the following results.

$^1$H-NMR (400 MHz, DMSO-d6): δ (ppm)=7.82 (m, 2H, Ar), 4.84 (ddd, 1H, CH₂O), 4.68 (ddd, 1H, CH₂O), 3.73 to 3.91 (m, 4H, CH₂), 1.55 to 2.45 (m, 31H, Ar—CH₃+CH₂+ adamantane+camphanic), 1.04 (s, 3H, CH₃), 1.03 (s, 3H, CH₃), 0.85 (s, 3H, CH₃)

$^{19}$F-NMR (376 MHz, DMSO-d6): δ (ppm)=−111.0

Based on the results of the above NMR analyses, the compound (B1-1-46) was confirmed as having the structure shown above.

Example 47

Synthesis of Compound (B1-1-47)

With the exception of replacing the 4-methylphenyldiphenylsulfonium bromide with a compound (48), reaction was conducted in the same manner as that described for the synthesis example of ii) in Example 1, thus yielding the compound (B1-1-47).

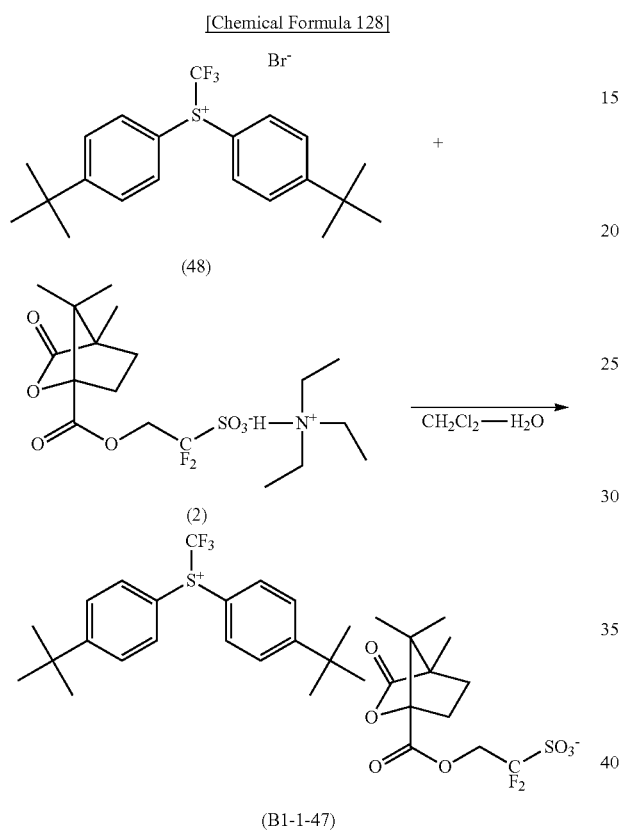

[Chemical Formula 128]

The thus obtained compound (B1-1-47) was analyzed using $^1$H-NMR and $^{19}$F-NMR, and the structure was identified on the basis of the following results.

$^1$H-NMR (400 MHz, DMSO-d6): δ (ppm)=8.23 (d, 4H, ArH), 7.98 (d, 4H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.37 (s, 18H, CH$_3$ of tert-butyl), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−48.5, −111.0

Based on the results of the above NMR analyses, the compound (B1-1-47) was confirmed as having the structure shown above.

Example 48

Synthesis of Compound (B1-1-48)

With the exception of replacing the 4-methylphenyldiphenylsulfonium bromide with a compound (49), reaction was conducted in the same manner as that described for the synthesis example of ii) in Example 1, thus yielding the compound (B1-1-48).

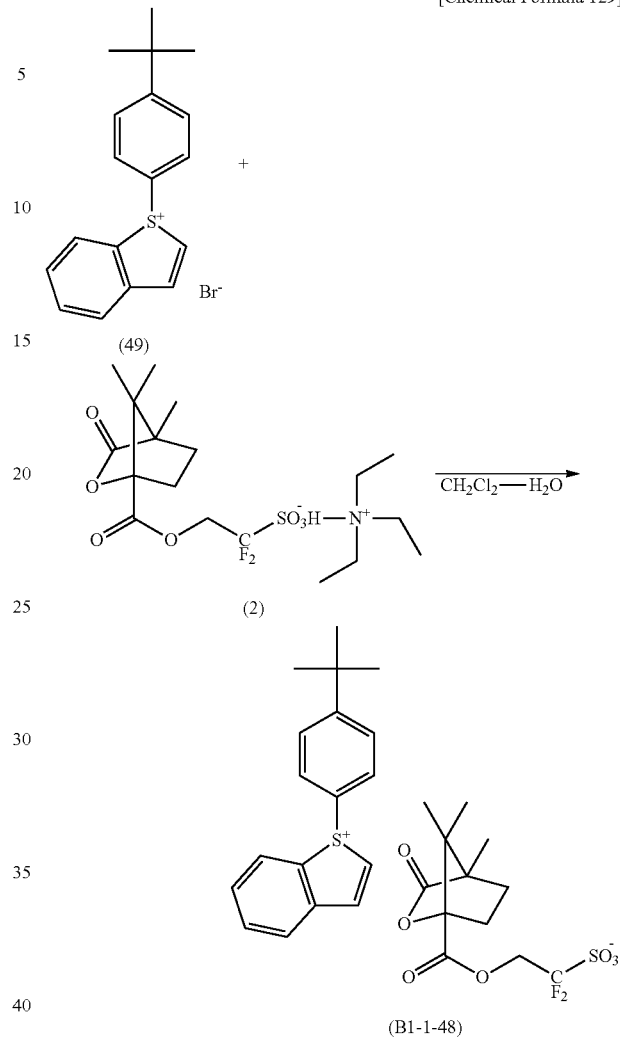

[Chemical Formula 129]

The thus obtained compound (B1-1-48) was analyzed using $^1$H-NMR and $^{19}$F-NMR, and the structure was identified on the basis of the following results.

$^1$H-NMR (400 MHz, DMSO-d6): δ (ppm)=8.28 (d, 2H, ArH), 8.12 (d, 1H, ArH), 7.88 (t, 1H, ArH), 7.80 (d, 1H, ArH), 7.62 to 7.74 (m, 5H, ArH), 4.84 (ddd, 1H, CH$_2$O), 4.68 (ddd, 1H, CH$_2$O), 2.38 to 2.45 (m, 1H, camphanic), 1.93 to 2.06 (m, 2H, camphanic), 1.55 to 1.61 (m, 1H, camphanic), 1.27 (s, 9H, tBu), 1.04 (s, 3H, CH$_3$), 1.03 (s, 3H, CH$_3$), 0.85 (s, 3H, CH$_3$)

$^{19}$F-NMR (376 MHz, DMSO-d6): δ (ppm)=−111.0

Based on the results of the above NMR analyses, the compound (B1-1-48) was confirmed as having the structure shown above.

Resist Composition Preparation (1)

Examples 49 to 57, Comparative Examples 1 to 8

The components shown in Table 1 were mixed together and dissolved to prepare a series of positive resist compositions.

TABLE 1

| | Component (A) | Component (B) | Component (D) | Component (E) | Component (S) | |
|---|---|---|---|---|---|---|
| Comparative Example 1 | (A)-1 [100] | (B)-11 [8.00] | (D)-1 [1.20] | (E)-1 [1.32] | (S)-1 [10] | (S)-2 [2400] |
| Comparative Example 2 | (A)-1 [100] | (B)-12 [7.81] | (D)-1 [1.20] | (E)-1 [1.32] | (S)-1 [10] | (S)-2 [2400] |
| Comparative Example 3 | (A)-1 [100] | (B)-13 [8.34] | (D)-1 [1.20] | (E)-1 [1.32] | (S)-1 [10] | (S)-2 [2400] |
| Comparative Example 4 | (A)-1 [100] | (B)-14 [8.75] | (D)-1 [1.20] | (E)-1 [1.32] | (S)-1 [10] | (S)-2 [2400] |
| Comparative Example 5 | (A)-2 [100] | (B)-11 [8.00] | (D)-1 [1.20] | (E)-1 [1.32] | (S)-1 [10] | (S)-2 [2400] |
| Comparative Example 6 | (A)-2 [100] | (B)-12 [7.81] | (D)-1 [1.20] | (E)-1 [1.32] | (S)-1 [10] | (S)-2 [2400] |
| Comparative Example 7 | (A)-2 [100] | (B)-13 [8.34] | (D)-1 [1.20] | (E)-1 [1.32] | (S)-1 [10] | (S)-2 [2400] |
| Comparative Example 8 | (A)-2 [100] | (B)-14 [8.75] | (D)-1 [1.20] | (E)-1 [1.32] | (S)-1 [10] | (S)-2 [2400] |
| Example 49 | (A)-1 [100] | (B)-1 [8.59] | (D)-1 [1.20] | (E)-1 [1.32] | (S)-1 [10] | (S)-2 [2400] |
| Example 50 | (A)-1 [100] | (B)-2 [8.39] | (D)-1 [1.20] | (E)-1 [1.32] | (S)-1 [10] | (S)-2 [2400] |
| Example 51 | (A)-2 [100] | (B)-1 [8.59] | (D)-1 [1.20] | (E)-1 [1.32] | (S)-1 [10] | (S)-2 [2400] |
| Example 52 | (A)-2 [100] | (B)-2 [8.39] | (D)-1 [1.20] | (E)-1 [1.32] | (S)-1 [10] | (S)-2 [2400] |
| Example 53 | (A)-2 [100] | (B)-3 [11.64] | (D)-1 [1.20] | (E)-1 [1.32] | (S)-1 [10] | (S)-2 [2400] |
| Example 54 | (A)-2 [100] | (B)-4 [10.92] | (D)-1 [1.20] | (E)-1 [1.32] | (S)-1 [10] | (S)-2 [2400] |
| Example 55 | (A)-2 [100] | (B)-5 [11.97] | (D)-1 [1.20] | (E)-1 [1.32] | (S)-1 [10] | (S)-2 [2400] |
| Example 56 | (A)-2 [100] | (B)-6 [11.03] | (D)-1 [1.20] | (E)-1 [1.32] | (S)-1 [10] | (S)-2 [2400] |
| Example 57 | (A)-2 [100] | (B)-7 [12.34] | (D)-1 [1.20] | (E)-1 [1.32] | (S)-1 [10] | (S)-2 [2400] |

In Table 1, the reference symbols have the meanings shown below. Further, the numerical values in brackets [ ] indicate the amount (in parts by weight) of the component added.

(A)-1: a copolymer (A1-11-1) represented by the chemical formula shown below, having Mw of 7,000 and Mw/Mn of 1.70. In the chemical formula shown below, the numbers at the bottom-right of the parentheses indicate the percentages (molar ratio) of the respective structural units within the copolymer.

[Chemical Formula 130]

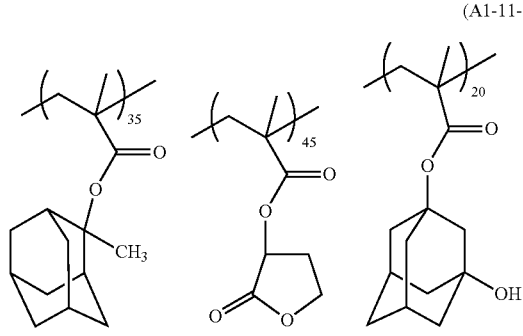

(A1-11-1)

(A)-2: a copolymer (A1-13-1) represented by the chemical formula shown below, having Mw of 7,900 and Mw/Mn of 1.56. In the chemical formula shown below, the numbers at the bottom-right of the parentheses indicate the percentages (molar ratio) of the respective structural units within the copolymer.

[Chemical Formula 131]

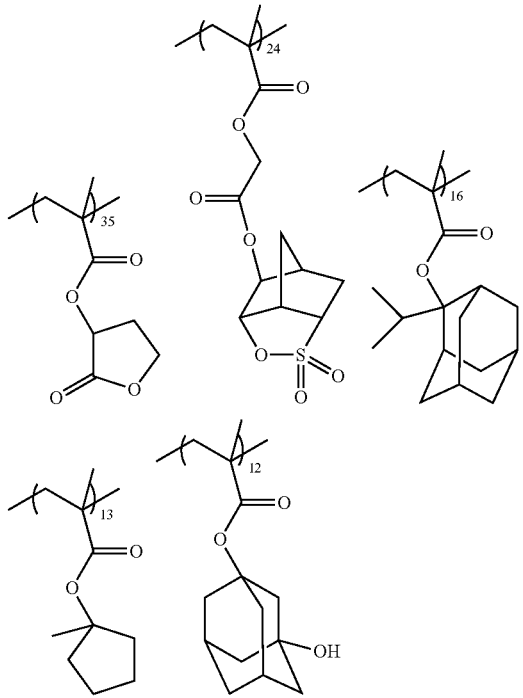

(A1-13-1)

(B)-1: the compound (B1-1-1) described above.
(B)-2: the compound (B1-1-2) described above.
(B)-3: the compound (B1-1-4) described above.
(B)-4: the compound (B1-1-5) described above.
(B)-5: the compound (B1-1-11) described above.
(B)-6: the compound (B1-1-28) described above.
(B)-7: the compound (B1-1-48) described above.
(B)-11: a compound (B2-1) represented by a chemical formula shown below.
(B)-12: a compound (B2-2) represented by a chemical formula shown below.
(B)-13: a compound (B2-3) represented by a chemical formula shown below.
(B)-14: a compound (B2-4) represented by a chemical formula shown below.

[Chemical Formula 132]

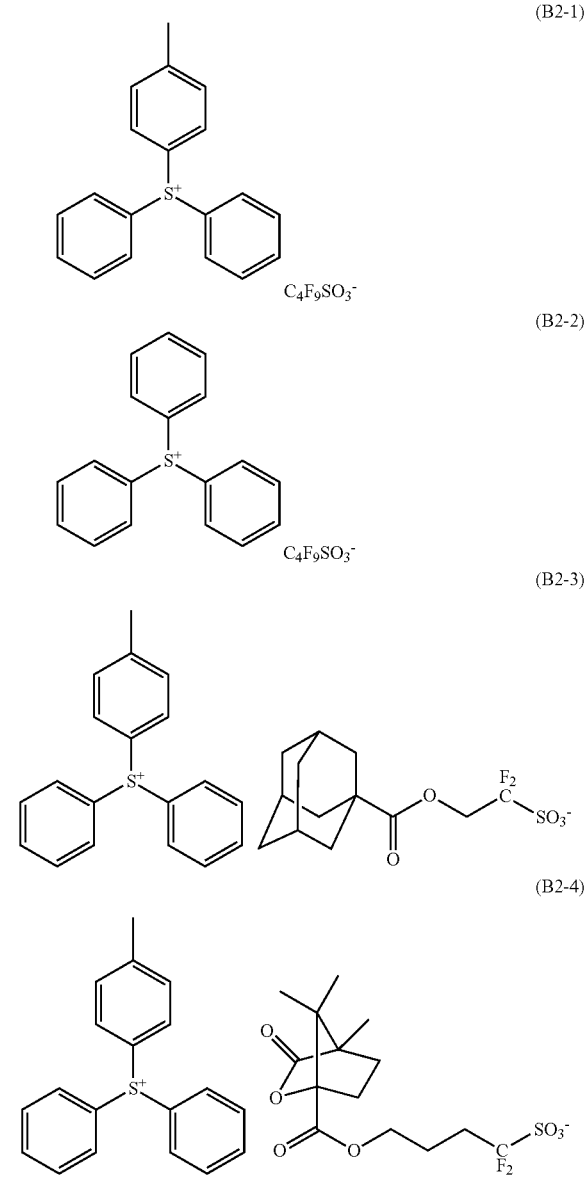

(D)-1: tri-n-pentylamine
(E)-1: salicylic acid (S)-1: γ-butyrolactone
(S)-2: a mixed solvent of PGMEA/PGME=6/4 (weight ratio)

<Evaluation of Lithography Properties and Resist Pattern Shape>

Using the obtained positive resist compositions, resist patterns were formed using the procedure described below, and each of the resist patterns was then evaluated in the manner described below.

[Formation of Resist Pattern]

An organic anti-reflection film composition ARC29A (a product name, manufactured by Brewer Science Ltd.) was applied to an 8-inch silicon wafer using a spinner, and the composition was then baked and dried on a hot plate at 205° C. for 60 seconds, thereby forming an organic anti-reflection film having a thickness of 82 nm.

Each of the positive resist compositions obtained above was applied onto this type of anti-reflection film using a spinner, and was then prebaked (PAB) on a hot plate at a PAB temperature indicated in Table 2 for 60 seconds and dried, thereby forming a resist film having a thickness of 150 nm.

Subsequently, the resist film was selectively irradiated with an ArF excimer laser (193 nm) through a mask (6% halftone), using an ArF exposure apparatus NSR-S302 (manufactured by Nikon Corporation, NA (numerical aperture)=0.60, ⅔ annular illumination).

Thereafter, a post exposure bake (PEB) treatment was conducted at a PEB temperature indicated in Table 2 for 60 seconds, and the resist film was then developed for 30 seconds at 23° C. in a 2.38% by weight aqueous solution of tetramethylammonium hydroxide (TMAH) NMD-3 (manufactured by Tokyo Ohka Kogyo Co., Ltd.). The resist film was then rinsed for 30 seconds with pure water, and shaken dry.

As a result, in each of the examples, a space and line resist pattern (hereinafter referred to as an "SL pattern") having spaces of width 120 nm arranged at equal intervals (pitch: 240 nm) was formed in the resist film.

The optimum exposure dose Eop (mJ/cm$^2$) for formation of the SL pattern, namely the sensitivity, was determined. The results are shown in Table 2.

[Evaluation of LWR (Line Width Roughness)]

Using the same procedure as that described above for the formation of a resist pattern, SL patterns having a space width of 120 nm and a pitch of 240 nm were formed at the above-mentioned Eop value, and the space width was measured at 400 points along the lengthwise direction of the space using a measuring scanning electron microscope (SEM) (scanning electron microscope, accelerating voltage: 800 V, product name: S-9220, manufactured by Hitachi, Ltd.). Based on these results, the value of 3 times the standard deviation (s) (namely, 3s) was determined. The average value of 3s across 5 locations was calculated as an indicator of the LWR. The results are shown in Table 2.

The smaller the value of 3s, the lower the level of roughness in the line width, indicating an SL pattern of more uniform width.

[Evaluation of Mask Error Factor (MEF)]

Using the same procedure as that described above for the formation of a resist pattern, and at the above-mentioned Eop, SL patterns were formed using a mask pattern targeting an SL pattern having a space width of 120 nm and a pitch of 260 nm and a mask pattern targeting an SL pattern having a space width of 130 nm and a pitch of 260 nm. The value of the MEF was then determined using the formula shown below. The results are shown in Table 2.

$$MEF=|CD_{130}-CD_{120}|/|MD_{130}-MD_{120}|$$

In this formula, $CD_{130}$ and $CD_{120}$ represent the respective space widths (nm) of the actual SL patterns formed using the mask pattern targeting a space width of 130 nm and the mask pattern targeting a line width of 120 nm respectively, and $MD_{130}$ and $MD_{120}$ represent the respective target space widths (nm) of the mask patterns, meaning $MD_{130}$=130 and $MD_{120}$=120.

The closer the MEF value is to 1, the more faithful the formed resist pattern is to the mask pattern.

[Evaluation of Exposure Margin (EL Margin)]

The exposure dose at which an SL pattern having a space width within a range specified by: [targeted dimension (space width of 120 nm)±5%] (namely, within a range from 114 nm to 126 nm) was formed was determined, and the EL margin (unit: %) was determined using the formula shown below. The results are shown in Table 2.

EL margin(%)=($|E1-E2|$/Eop)×100

E1: the exposure dose (mJ/cm$^2$) for forming an SL pattern with a space width of 114 nm E2: the exposure dose (mJ/cm$^2$) for forming an SL pattern with a space width of 126 nm.

The larger the value for the EL margin, the smaller the variation in the pattern size caused by fluctuation in the exposure dose.

[Evaluation of Resist Pattern Shape]

An SL pattern with a space width of 120 nm and a pitch of 240 nm formed at the above-mentioned Eop was inspected using a scanning electron microscope, and the cross-sectional shape of the SL pattern was evaluated. The results are shown in Table 2.

TABLE 2

|  | PAB temperature (°C.) | PEB temperature (°C.) | Sensitivity (mJ/cm$^2$) | LWR (nm) | MEF | EL margin (%) | Resist pattern shape |
| --- | --- | --- | --- | --- | --- | --- | --- |
| Comparative Example 1 | 110 | 110 | 31 | 13.8 | 2.98 | 6.32 | round top |
| Comparative Example 2 | 110 | 110 | 28 | 12.7 | 3.08 | 6.60 | round top |
| Comparative Example 3 | 110 | 110 | 41 | 11.8 | 2.46 | 6.75 | T-top |
| Comparative Example 4 | 110 | 110 | 35 | 12.1 | 2.40 | 6.71 | round top |
| Comparative Example 5 | 90 | 90 | 34 | 13.3 | 2.75 | 6.10 | round top |
| Comparative Example 6 | 90 | 90 | 29 | 12.0 | 3.05 | 6.20 | round top |
| Comparative Example 7 | 90 | 90 | 40 | 11.3 | 2.30 | 6.83 | T-top |
| Comparative Example 8 | 90 | 90 | 45 | 11.7 | 2.38 | 6.51 | round top |
| Example 49 | 110 | 110 | 39 | 11.0 | 2.25 | 7.07 | rectangular |
| Example 50 | 110 | 110 | 36 | 10.6 | 2.19 | 7.18 | rectangular |
| Example 51 | 90 | 90 | 51 | 10.3 | 2.07 | 7.33 | rectangular |
| Example 52 | 90 | 90 | 44 | 10.2 | 2.04 | 7.41 | rectangular |
| Example 53 | 90 | 90 | 61 | 9.9 | 2.11 | 7.85 | rectangular |
| Example 54 | 90 | 90 | 58 | 9.9 | 2.03 | 7.99 | rectangular |
| Example 55 | 90 | 90 | 57 | 10.4 | 2.01 | 7.51 | rectangular |
| Example 56 | 90 | 90 | 54 | 10.0 | 1.97 | 8.05 | rectangular |
| Example 57 | 90 | 90 | 53 | 9.5 | 2.10 | 8.34 | rectangular |

The above results in Table 2 confirmed that, compared with the resist patterns formed using the resist compositions of Comparative Examples 1 to 8, the resist patterns formed using the resist compositions of Examples 49 to 57 exhibited superior lithography properties, with favorable levels of LWR, MEF and EL margin, and were also of a more favorable shape, with a high degree of rectangularity.

In particular, comparison of Example 49 with Comparative Examples 3 and 4, and comparison of Example 51 with Comparative Examples 7 and 8 confirmed that the compound of the present invention represented by general formula (b1-1) was very useful as an acid generator for resist compositions.

While preferred embodiments of the invention have been described, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

The invention claimed is:

1. A resist composition, comprising a base component (A) which exhibits changed solubility in an alkali developing-solution under action of acid, and an acid-generator component (B) which generates acid upon exposure, wherein
the acid-generator component (B) comprises an acid generator (B1) containing a compound represented by general formula (b1-1) shown below:

[Chemical Formula 1]

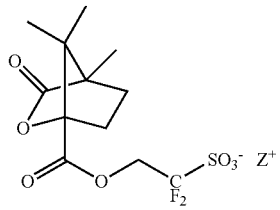

(b1-1)

wherein $Z^+$ represents an organic cation.

2. The resist composition according to claim 1, wherein $Z^+$ in the general formula (b1-1) is an organic cation represented by general formula (b1-c1) or general formula (b1-c2) shown below:

[Chemical Formula 2]

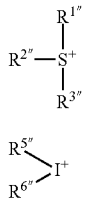

(b1-c1)

(b1-c2)

wherein each of $R^{1\prime\prime}$ to $R^{3\prime\prime}$ and $R^{5\prime\prime}$ to $R^{6\prime\prime}$ independently represents an aryl group which may have a substituent, an alkyl group or an alkenyl group, and two of $R^{1\prime\prime}$ to $R^{3\prime\prime}$ in the formula (b1-c1) may be bonded to each other to form a ring together with a sulfur atom in the formula.

3. The resist composition according to claim 1, wherein an amount of the acid generator (B1) is within a range from 1 to 60 parts by weight per 100 parts by weight of the base component (A).

4. The resist composition according to claim 1, wherein the base component (A) is a base component that exhibits increased solubility in an alkali developing solution under action of acid.

5. The resist composition according to claim 4, wherein the base component (A) comprises a resin component (A1) having a structural unit (a1), which is derived from an acrylate ester that may have an atom other than a hydrogen atom or a substituent bonded to a carbon atom on an α-position, and contains an acid-dissociable, dissolution-inhibiting group.

6. A method of forming a resist pattern, the method comprising: forming a resist film on a substrate using the resist composition according to claim 1, subjecting the resist film to exposure, and subjecting the resist film to alkali developing to form a resist pattern.

7. A compound represented by general formula (b1-1) shown below:

[Chemical Formula 3]

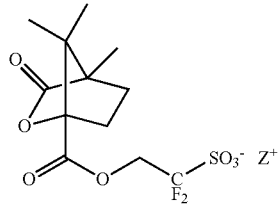

(b1-1)

wherein $Z^+$ represents an organic cation.

8. The compound according to claim 7, wherein $Z^+$ in the general formula (b1-1) is an organic cation represented by general formula (b1-c1) or general formula (b1-c2) shown below:

[Chemical Formula 2]

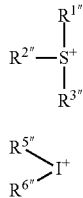

(b1-c1)

(b1-c2)

wherein each of $R^{1\prime\prime}$ to $R^{3\prime\prime}$ and $R^{5\prime\prime}$ to $R^{6\prime\prime}$ independently represents an aryl group which may have a substituent, an alkyl group or an alkenyl group, and two of $R^{1\prime\prime}$ to $R^{3\prime\prime}$ in the formula (b1-c1) may be bonded to each other to form a ring together with a sulfur atom in the formula.

9. An acid generator comprising the compound according to claim 7.

* * * * *